(12) United States Patent
Jespersen et al.

(10) Patent No.: US 10,792,000 B2
(45) Date of Patent: Oct. 6, 2020

(54) SYSTEM FOR ASSESSING TISSUE SUBSTANCE EXTRACTION

(75) Inventors: Sune Nørhøj Jespersen, Hadsten (DK); Kim Mouridsen, Hjortshøj (DK); Leif Østergaard, Risskov (DK)

(73) Assignees: AARHUS UNIVERSITET, Aarhus C. (DK); REGION MIDTJYLLAND, Viborg (DE)

( * ) Notice: Subject to any disclaimer, the term of this patent is extended or adjusted under 35 U.S.C. 154(b) by 0 days.

(21) Appl. No.: 14/008,487

(22) PCT Filed: Mar. 30, 2012

(86) PCT No.: PCT/DK2012/050102
§ 371 (c)(1),
(2), (4) Date: Sep. 27, 2013

(87) PCT Pub. No.: WO2012/130249
PCT Pub. Date: Oct. 4, 2012

(65) Prior Publication Data
US 2014/0018649 A1    Jan. 16, 2014

Related U.S. Application Data

(60) Provisional application No. 61/470,154, filed on Mar. 31, 2011.

(30) Foreign Application Priority Data

Mar. 31, 2011    (DK) ................................ 2011 70155

(51) Int. Cl.
*A61B 6/03*    (2006.01)
*A61B 3/12*    (2006.01)
(Continued)

(52) U.S. Cl.
CPC ............ *A61B 6/037* (2013.01); *A61B 3/1233* (2013.01); *A61B 5/026* (2013.01);
(Continued)

(58) Field of Classification Search
CPC ......... A61B 6/037; A61B 6/508; A61B 8/481; A61B 8/06; A61B 6/507; A61B 5/145;
(Continued)

(56) References Cited

U.S. PATENT DOCUMENTS 7,069,068 B1    6/2006    Østergaard
2006/0083687 A1    4/2006    Yang
2006/0161062 A1    7/2006    Arditi et al.

FOREIGN PATENT DOCUMENTS

WO    WO 2004/110279 A1    12/2004
WO    WO 2006/067201 A2    6/2006

OTHER PUBLICATIONS

Miyauchi et al., "Diffusion and Back-Flow Models for Two-Phase Axial Dispersion", Ind. Eng. Chem. Fundamen., 1963, 2 (4), pp. 304-310.*
(Continued)

*Primary Examiner* — Hien N Nguyen
(74) *Attorney, Agent, or Firm* — Woodard, Emhardt, Henry, Reeves & Wagner, LLP

(57) ABSTRACT

The present invention relates to a system for measuring a micro-vascular flow distribution of a tissue portion of a mammal comprising means (101) for measuring a first indicator (MTT) for the blood flow through a capillary bed, means (102) for measuring a second indicator (CTTH) of heterogeneity of the blood flow in said capillary bed, and a first processor (110) arranged for using the first and the second indicator to estimate an extraction capacity (EC) of a substance from the blood in said capillary bed.

9 Claims, 36 Drawing Sheets

(51) Int. Cl.

| | |
|---|---|
| *A61B 5/026* | (2006.01) |
| *A61B 5/055* | (2006.01) |
| *A61B 5/00* | (2006.01) |
| *A61B 6/00* | (2006.01) |
| *A61B 5/145* | (2006.01) |
| *A61B 8/06* | (2006.01) |
| *A61B 8/08* | (2006.01) |
| *A61B 5/02* | (2006.01) |
| *A61B 5/1455* | (2006.01) |
| *A61B 8/00* | (2006.01) |
| *A61B 18/00* | (2006.01) |
| *G16H 50/50* | (2018.01) |

(52) U.S. Cl.
CPC .......... *A61B 5/02007* (2013.01); *A61B 5/055* (2013.01); *A61B 5/145* (2013.01); *A61B 5/14551* (2013.01); *A61B 5/4064* (2013.01); *A61B 5/4848* (2013.01); *A61B 5/7282* (2013.01); *A61B 6/032* (2013.01); *A61B 6/481* (2013.01); *A61B 6/501* (2013.01); *A61B 6/504* (2013.01); *A61B 6/507* (2013.01); *A61B 6/508* (2013.01); *A61B 8/00* (2013.01); *A61B 8/06* (2013.01); *A61B 8/481* (2013.01); *A61B 5/14532* (2013.01); *A61B 5/14542* (2013.01); *A61B 5/4082* (2013.01); *A61B 5/4088* (2013.01); *A61B 8/0816* (2013.01); *A61B 2018/00446* (2013.01); *A61B 2576/026* (2013.01); *G06T 2207/30016* (2013.01); *G06T 2207/30104* (2013.01); *G16H 50/50* (2018.01)

(58) Field of Classification Search
CPC ....... A61B 6/481; A61B 5/4064; A61B 6/504; A61B 6/501; A61B 8/00; A61B 6/032; A61B 5/7282; A61B 5/14551; A61B 5/02007; A61B 5/4848; A61B 5/055; A61B 5/026; A61B 3/1233; A61B 8/0816; A61B 5/4088; A61B 2576/026; A61B 5/14542; A61B 5/14532; A61B 5/4082; A61B 2018/00446; G16H 50/50; G06T 2207/30104; G06T 2207/30016

See application file for complete search history.

(56) References Cited

OTHER PUBLICATIONS

Tsoukias et al., "A computational model of oxygen delivery by hemoglobin-based oxygen carriers in three-dimensional microvascular networks", Journal of Theor Biol. Oct. 21, 2007; 248(4): 657-674.*

Groner et al., "Orthogonal polarization spectral imaging: A news method for study of the microcirculation", Nature Medicine, vol. 5, No. 10, Oct. 1999, pp. 1209-1213.*

Attwell, David et al., "Glial and neuronal control of brain blood flow" Nature, Nov. 11, 2010, pp. 232-243, vol. 468, No. 7321.

King, Richard B. et al., "Modeling Blood Flow Heterogeneity" Annals of Biomedical Engineering, 1996, pp. 352-372, vol. 24.

Koh, T.S. et al., "A distributed parameter model of cerebral blood-tissue exchange with account of capillary transit time distribution" Neuroimage, 2006, pp. 426-435, vol. 30.

Zheng, Ying et al., "A Model of the Hemodynamic Response and Oxygen Delivery to Brain." NeuroImage 16, 617-637 (2002). 21 pages.

European Patent Application No. 12 712 915.3 Search Report dated Feb. 5, 2020. 7 pages.

Nielsen, RB et al. "Impaired Perfusion and Capillary Dysfunction in Prodromal Alzhemer's Disease". Alzheimer's & Dementia: Diagnosis, Assessment & Disease Monitoring Feb. 2, 2020. 37 pages.

* cited by examiner

Fig. 3

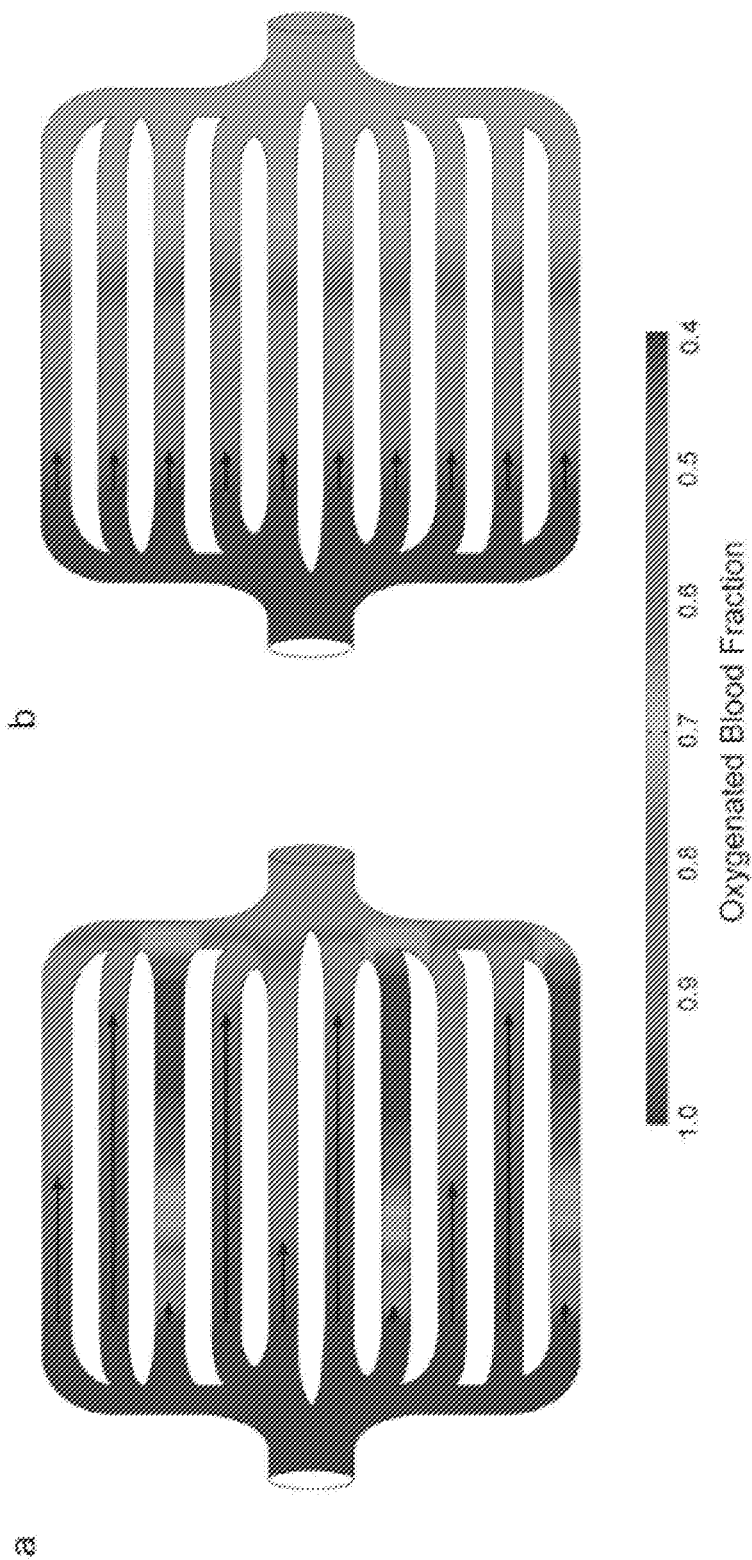
Fig. 4.a-b

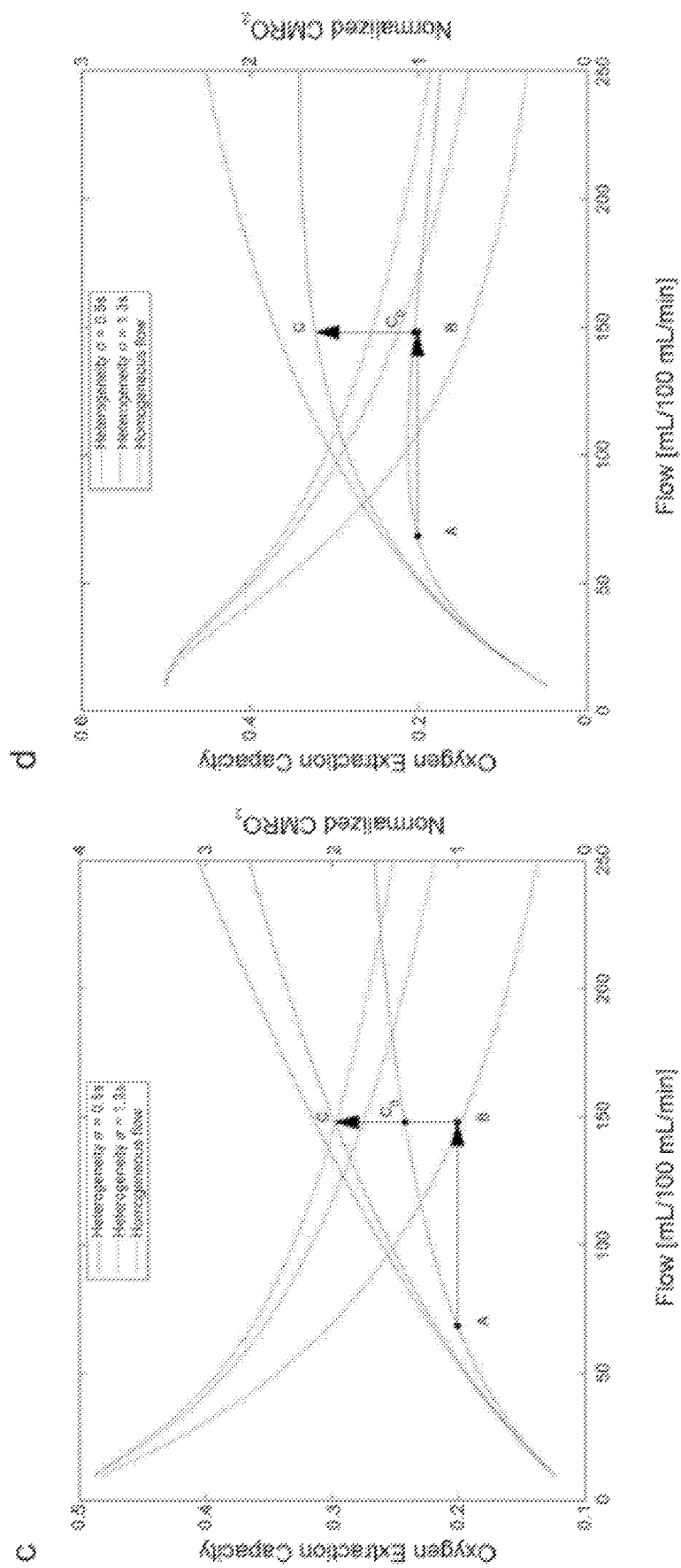
Fig. 4.c-d

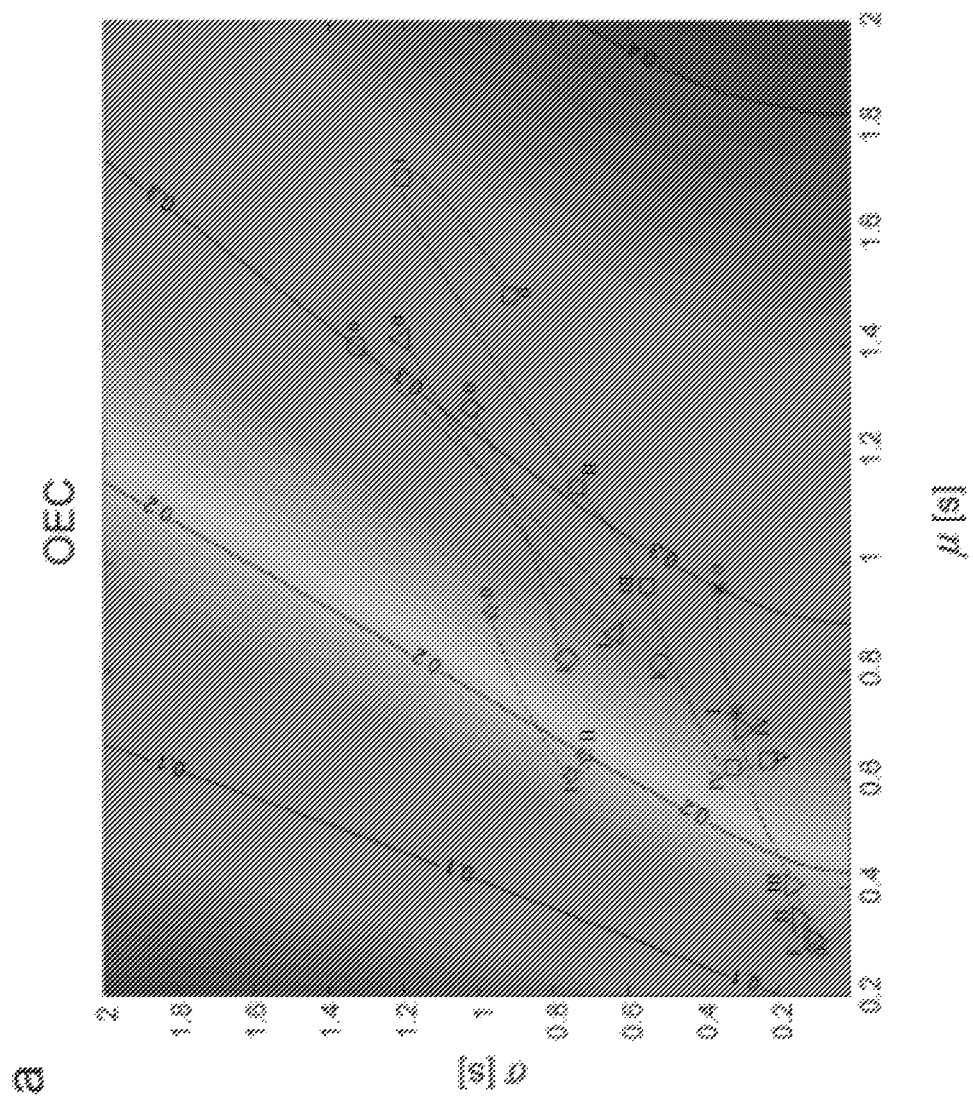
Fig. 6.a

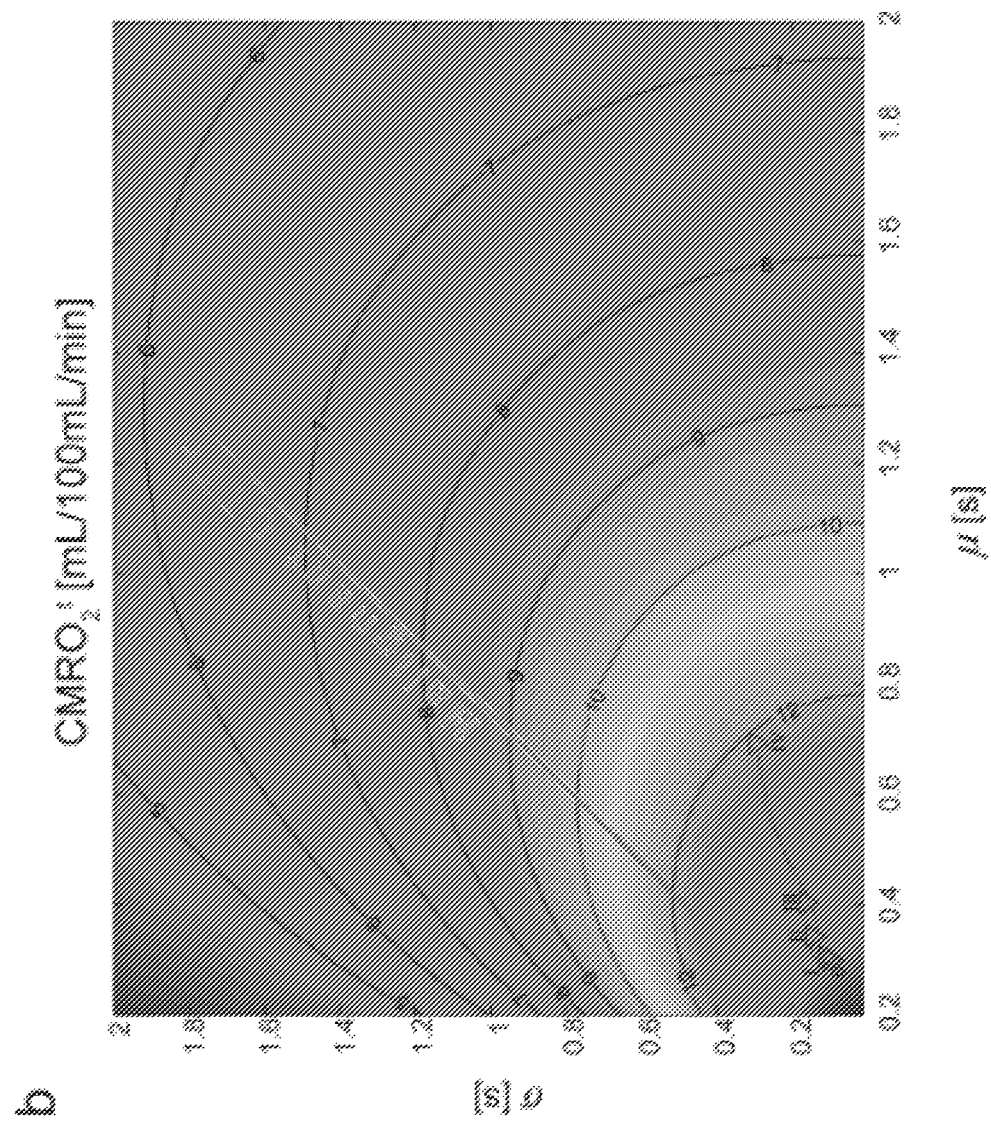
Fig. 6.b

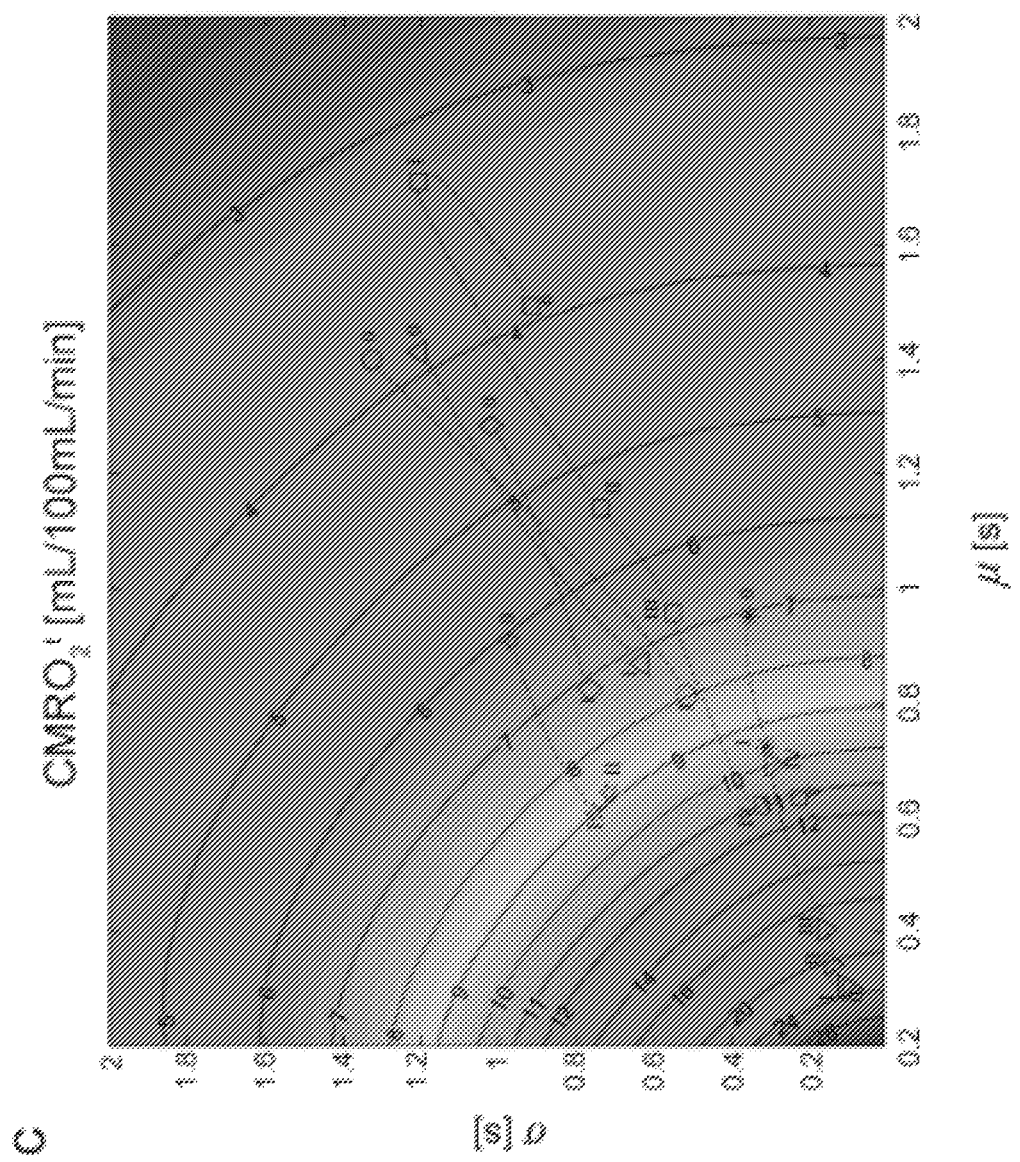
Fig. 6.c

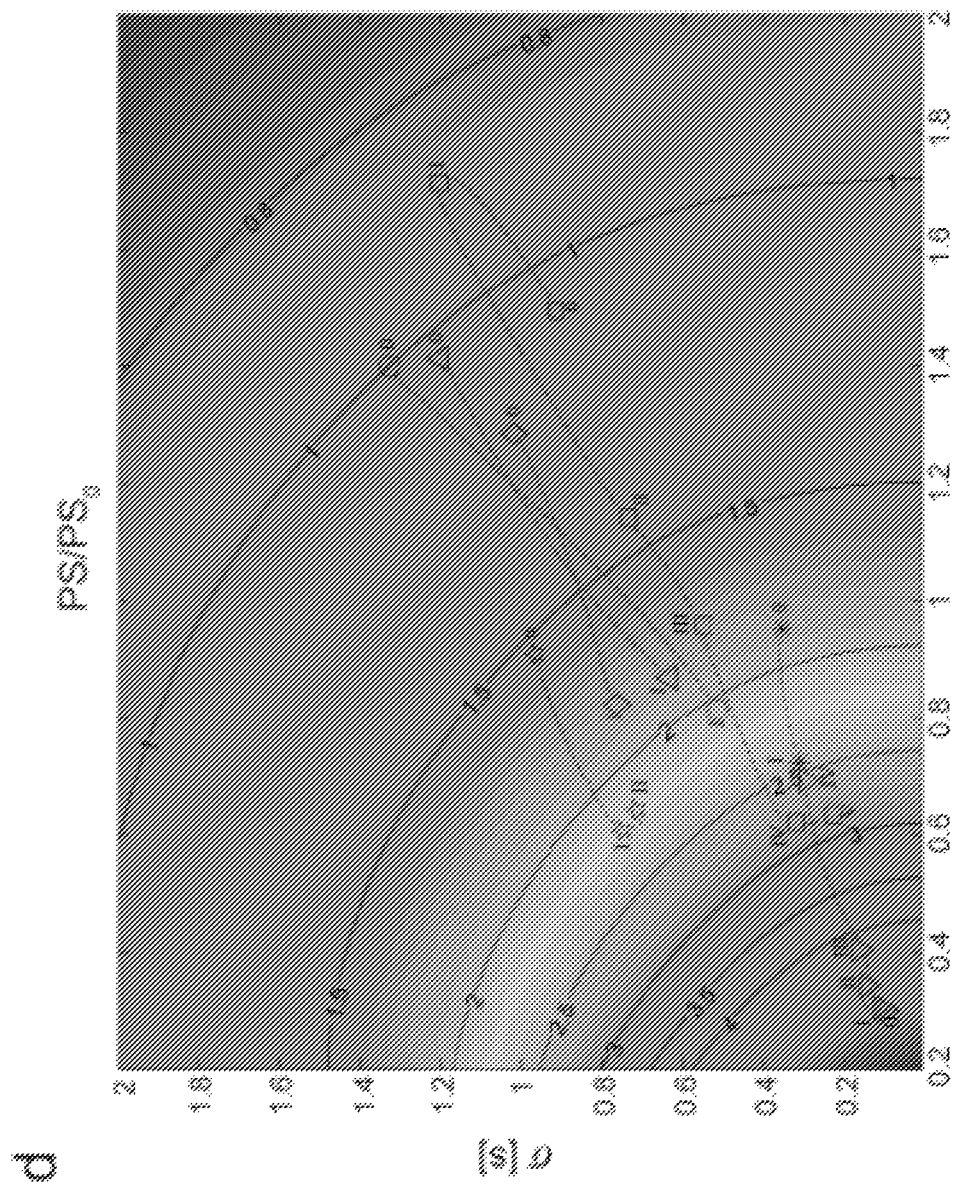
Fig. 6.d

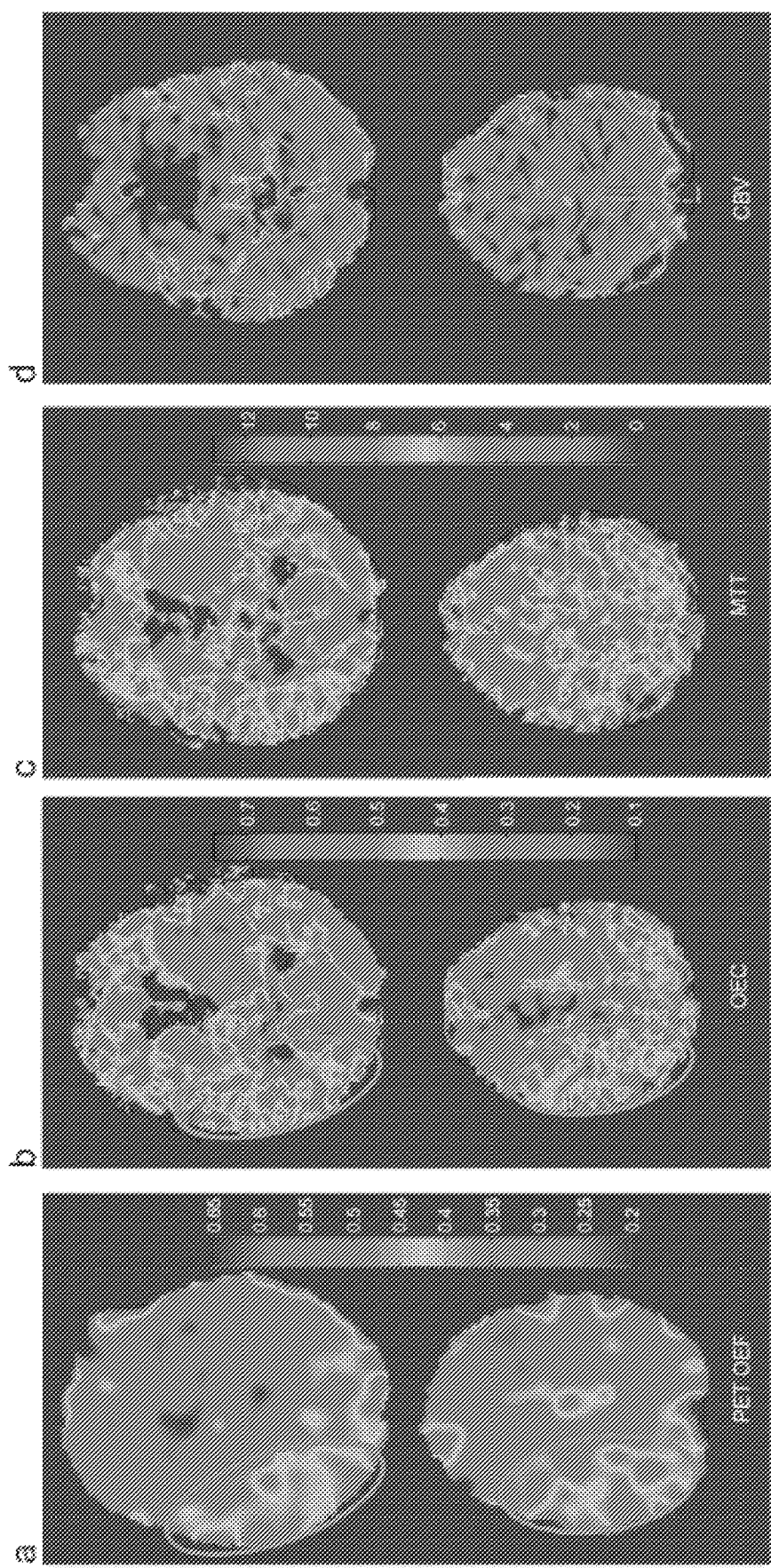
Fig. 7.a-d

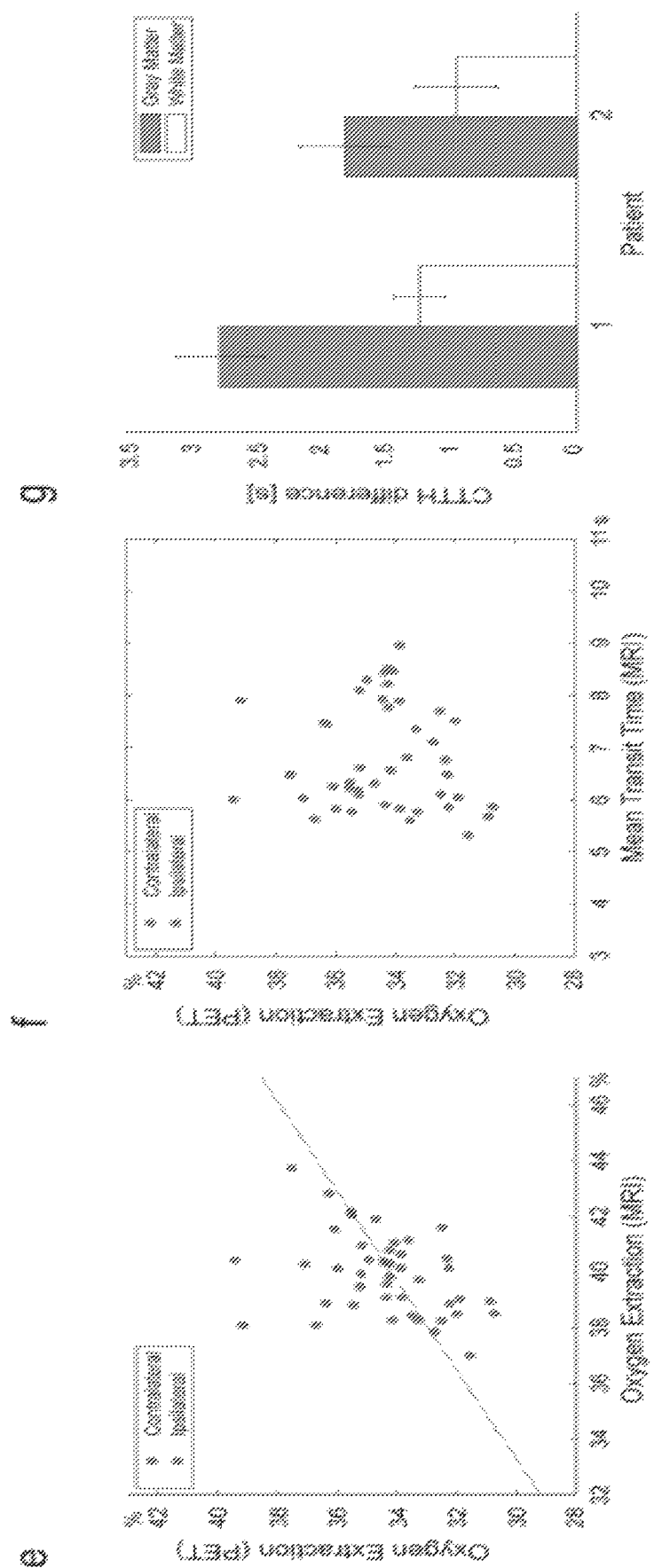
Fig. 7.e-f

Fig. 13

|  | AD | Control |
|---|---|---|
| Mean age (SD) in years | 72.9 (5.1) | 67.1 (6.4) |
| Females | 13 | 9 |
| Mean MMSE (SD) | 24.5 (2.7), n=13 | 29.4 (0.7), n=16 |

Table 1. demographic characteristics and MMSE score for study groups.

| Lobes | | PT Mean (SD) | CT Mean (SD) | PT vs. CT t-statistics |
|---|---|---|---|---|
| Frontal | OEC | 0.85 (0.07) | 0.79 (0.08) | 2.45* |
|  | FH | 0.89 (0.26) | 0.75 (0.11) | 2.11* |
| Parietal | OEC | 0.86 (0.06) | 0.79 (0.08) | 3.11* |
|  | FH | 0.84 (0.1) | 0.75 (0.11) | 2.71* |
| Temporal | OEC | 0.76 (0.06) | 0.79 (0.08) | -1.44 |
|  | FH | 0.73 (0.10) | 0.75 (0.1) | -0.39 |

Table 2. Summary of ROI analysis. $p < 0.05$

SYSTEM FOR ASSESSING TISSUE SUBSTANCE EXTRACTION

CROSS REFERENCE TO RELATED APPLICATIONS

This application is a U.S. National Phase Application of PCT International Application Number PCT/DK2012/050102, filed on Mar. 30, 2012, designating the United States of America and published in the English language, which is an International Application of and claims the benefit of priority to Danish Patent Application No. PA 2011 70155, filed on Mar. 31, 2011, and U.S. Provisional Application No. 61/470,154, filed on Mar. 31, 2011. The disclosures of the above-referenced applications are hereby expressly incorporated by reference in their entireties.

TECHNICAL FIELD OF THE INVENTION

The present invention relates to measurement techniques for assessing the extraction of a substance transported by the blood, such as oxygen, drugs and nutrients into the tissue. In particular the present invention relates to a system for assessing such extraction.

BACKGROUND OF THE INVENTION

The process of blood passing through the tissues is called perfusion, and is one of the most fundamental physiological quantifiables. Disorders of perfusion is a process leading to mammal disability and mortality.

Angiopathy is the generic term for a disease of the blood vessels and is further categorized in macroangiopathy and microangiopathy. In macroangiopathy, the walls of major vessels undergo changes, and ultimately hinder sufficient blood flow. In microangiopathy, the walls of the smaller blood vessels become so thick and weak that they bleed, leak protein, and slow the flow of blood through the smallest blood vessels, resulting in an impairment of the flow of oxygen and nutrients to the tissues.

Hence, the consequences of angiopathy are of direct diagnostic value, and a system for such measurements would be advantageous.

SUMMARY OF THE INVENTION

Thus, one aspect of the present invention relates to a system for measuring a micro-vascular flow distribution of a tissue portion of a mammal, the system comprises:
  means for measuring a first indicator for the blood flow through a capillary bed;
  means for measuring a second indicator of heterogeneity of the blood flow in said capillary bed; and
  a first processor arranged for using the first and the second indicator to estimate an extraction capacity (EC) of a substance from the blood in said capillary bed;
wherein the first processor applies a model connecting the first and the second indicator to the extraction capacity (EC) of a substance from the blood in said capillary bed, the model comprising the transfer rate of total substance concentration ($C_T$) across the capillaries being linearly dependent on the plasma concentration of the substance ($C_P$), the model further having a non-vanishing back flow of the substance from the tissue into the capillaries.

Another aspect of the present invention relates to a database comprising references levels of one, or more, of the first indicator, the second indicator and the extraction capacity for one or more subjects with:
  shock, including circulatory and septic shock;
  stroke;
  hypoxia;
  ischemia, including myocardial and renal ischemia, and reperfusion injury in any organ;
  hypoperfusional states;
  Sickle cell disease;
  hypotension, including hemorrhagic hypotension;
  cancer, including malignant tumors;
  diabetes and obesity;
  hypertension;
  systemic autoimmunes diseases including systemic sclerosis
  virus related encephalopathy
  psychiatric disorders associated with chronic inflammation, such as depression, schizophrenia, ADHD and autism, aging; or
  neurodegenerative diseases, including Alzheimer's disease and other dementias, Parkinson's disease, Huntington's Disease and multiple sclerosis.

BRIEF DESCRIPTION OF THE FIGURES

FIG. 3 shows a table with data from all available in vivo recordings, in which transit time characteristics were reported in such a manner that the inventors model could be applied with limited assumptions. These were all performed in rat brain.

FIG. 4 shows the effects of CTTH on oxygen extraction,

FIG. 6 shows a general model of the effects of vasodilation (x-axis) and CTTH (y-axis) on oxygen extraction capacity. Contour plot of OEC (6.a) for a given mean transit time (μ) and capillary flow heterogeneity (σ). The corresponding maximum oxygen delivery is shown in FIG. 6.b assuming fixed CBV=1.6%, and Grubb's relation in FIG. 6.c. In FIG. 6.d, the effective permeability surface area normalized to the control state is given as a function of μ and σ (Stefanovic et al., 2008). Resting state values assumed are CBF=60 mL/100 mL/min and $C_{aO2}$=19 mL/100 mL. Legends: ○=Functional Activation (Stefanovic et al., 2008); □=Cortical electrical stimulation (Schulte et al., 2003); ∇=hypotension (Hudetz et al., 1995); *=mild hypoxia (Hudetz et al., 1997); Δ=severe hypoxia (Krolo and Hudetz, 2000); ◇=mild hypocapnia (Villringer et al., 1994); ☆=severe hypercapnia (Hudetz et al., 1997), FIG. 7 shows comparison of gold-standard PET OEF and MRI OEC maps, FIG. 13 shows to tables; Table 1 gives Mini-Mental-State Examination (MMSE) scores for the test persons (AD and control group); Table 2 gives the summary of the ROI (Region Of Interest) analysis, FIG. 24.c. shows net oxygenation as a function of tissue oxygen tension and CTTH for fixed CBF (such as in neurovascular dysfunction). In this figure, CBF and CBV were kept constant (CBF=60 mL/100 mL/min; CBV 1.6%; mean transit time 1.4 s) to illustrate how tissue oxygen tension and CTTH contribute to the metabolic needs of tissue during rest and as metabolic needs are increased with blocked CBF and CTTH (owing to capillary dysfunction). Note that an oxygen tension decrease of 5 mmHg supports a CMRO2 increase of roughly 20%, which correspond to the energy requirements of neuronal firing.

Figure 1:
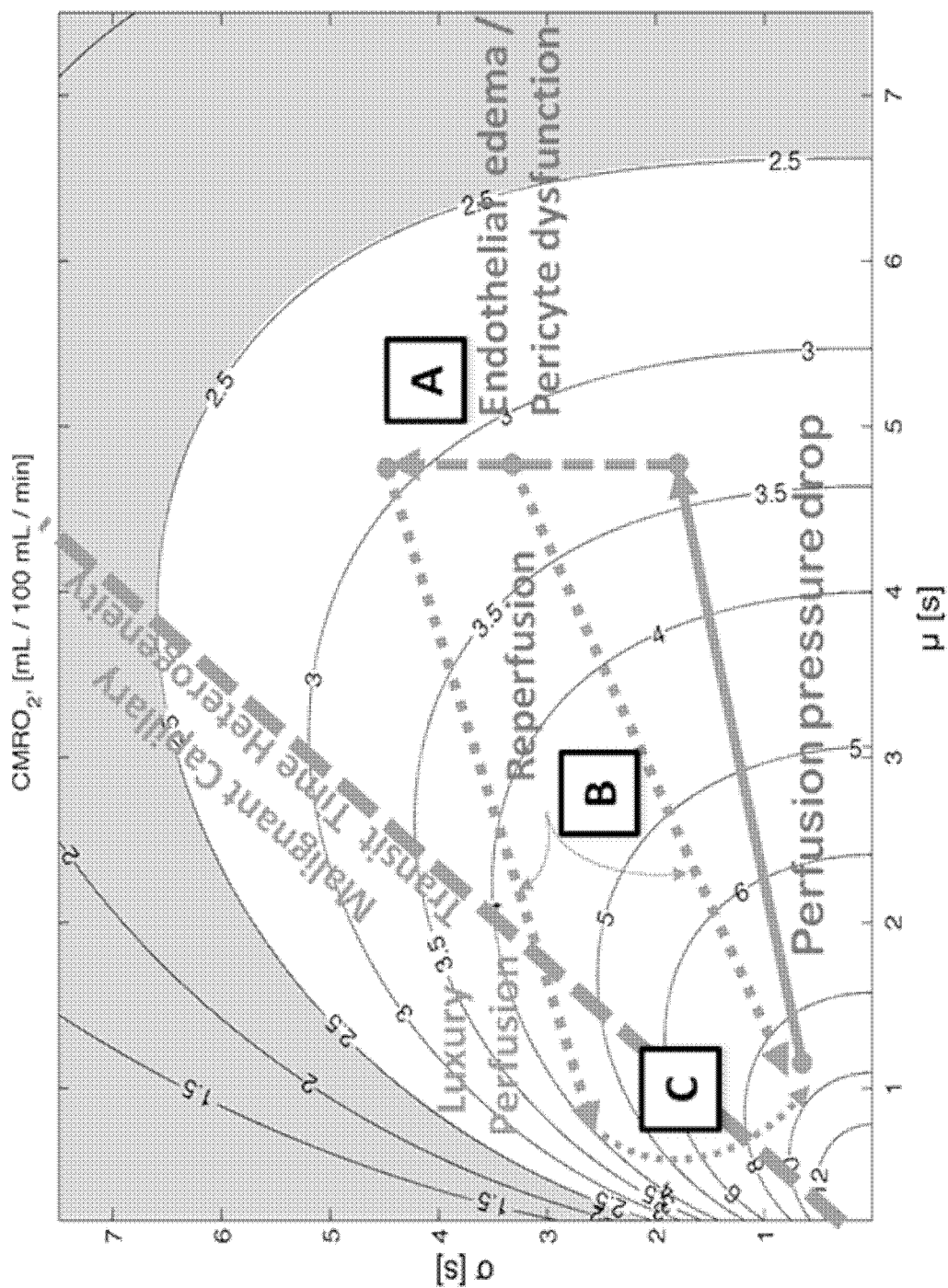
FIG. 1 shows the metabolic effects of tissue reperfusion in case of reversible and irreversible capillary flow disturbances.

The present invention will now be described in more detail in the following.

DETAILED DESCRIPTION OF THE INVENTION

The function and survival of most tissues depend critically on moment-to-moment regulation of oxygen supply by the blood-stream to meet changing metabolic needs. While a range of mechanisms adjust local blood flow by altering arteriolar tone, the capillary bed is not believed to participate actively in regulation of tissue oxygenation, except in muscle. This paradigm fails to explain oxygen extraction values during increased metabolic demands in heart and brain, and evidence of hypoxia in a range of diseases with normal blood flow.

The inventors of the present invention have found that the flow heterogeneity through the capillary bed has a significant influence on the extraction of a substance transported by the blood, such as oxygen, drugs and nutrients. Furthermore, the inventors have developed a system for predicting such extraction.

The inventors have found that there may be hypoxia in tissue despite normal blood flow, and that an indicator for the blood flow through a capillary bed and an indicator of heterogeneity of the blood flow in said capillary bed are needed to say for sure.

Furthermore, the inventors have proven that the blood flow through a capillary bed and the heterogeneity of the blood flow in said capillary bed in a range of pre-clinical and clinical diseases are disturbed. This may explain why tissue looses its normal function, degenerates or dies in these diseases, despite normal blood flow.

Hence, one aspect relates to a system for measuring a micro-vascular flow distribution of a tissue portion of a mammal, the system comprises:
  means for measuring a first indicator for the blood flow through a capillary bed;
  means for measuring a second indicator of heterogeneity of the blood flow in said capillary bed;
  a first processor arranged for using the first and the second indicator to estimate an extraction capacity (EC) of a substance from the blood in said capillary bed;
wherein the first processor applies a model connecting the first and the second indicator to the extraction capacity (EC) of a substance from the blood in said capillary bed, the model comprising the transfer rate of total substance concentration ($C_T$) across the capillaries being linearly dependent on the plasma concentration of the substance ($C_P$).

In the present context, said means for measuring the first indicator, said means for measuring the second indicator, and/or said processor may—in an individual embodiment of the invention—be physically, functionally and logically implemented in any suitable way such as in a single unit, in a plurality of units or as part of separate functional units. The invention may be implemented in a single unit, or be both physically and functionally distributed between different units and processors as will be readily understood by a person skilled in the art. Thus, the invention can be implemented by means of hardware, software, firmware or any combination of these. The invention, or some of the features thereof, can also be implemented as software running on one or more data processors and/or digital signal processors.

In another aspect, the present invention also relates to a computer program product being adapted to enable a computer system comprising at least one computer having data storage means in connection therewith to control said system according to an aspect of the invention.

In the present context, it is to be understood that the linear dependence on the plasma concentration of the substance ($C_P$) of the model may deviate to some extent from the exact linear dependency, e.g. the linear dependency may an initial approximation to a more advanced model having non-linear terms.

It is also contemplated that the invention may be implemented in another variant with a more complex behaviour than linear. Thus, in another aspect the present invention relates to a system for measuring a micro-vascular flow distribution of a tissue portion of a mammal, the system comprises:
  means for measuring a first indicator for the blood flow through a capillary bed;
  means for measuring a second indicator of heterogeneity of the blood flow in said capillary bed; and
  a first processor arranged for using the first and the second indicator to estimate an extraction capacity (EC) of a substance from the blood in said capillary bed;
wherein the first processor applies a model connecting the first and the second indicator to the extraction capacity (EC) of a substance from the blood in said capillary bed.

In the present context, the term "plasma concentration" refers to the amount of a substance present in the portion of the blood called the plasma.

In the present context, the term "extraction capacity" refers to the maximal fraction of a substance that can be extracted from arterial blood during a passage of the capillary bed, according to the biophysical model described. The extraction capacity may be affected by physiological states and pre-clinical and clinical disease states.

In the present context, the term "extraction fraction" refers to the fraction of a substance that the cells or the tissue is actually extracting from arterial blood during a passage of the capillary bed, according to the biophysical model described. Hence, the extraction fraction will always be lower than or equal to the extraction capacity.

EC (e.g. OEC) and EF (e.g. OEF) may be used interchangeably in the formulas in the present context.

In one aspect of the present invention, the first processor (110) is arranged for using the first and the second indicator to estimate an extraction fraction (EF) of a substance from the blood in said capillary bed.

In another aspect of the present invention, the first processor (110) is arranged for using the first and the second indicator to estimate an extraction fraction (EF) and/or extraction capacity of a substance from the blood in said capillary bed.

In the present context, the term "capillary bed" refers to an interweaving network of capillaries supplying a specified part of an organ or a tissue. The capillary bed may, in the context of present invention, have various spatial extensions depending of the nature of the means applied for measuring the first indicator for the blood flow through the capillary bed; and/or the nature of the means for measuring a second indicator of heterogeneity of the blood flow in said capillary bed, and/or on the tissue being measured upon. The capillary bed or structure consists of a network of capillaries having a basic dimension in the micro-meter range, typical brain capillary has for instance a length of 120 micrometer and 8 micrometer in diameter. The extension of the capillary bed will therefore be limited from below by the need for measuring on a plurality of capillaries to derive a meaningful measure of the heterogeneity (CTTH). Similarly, the extension of the capillary bed will typically be limited by the available spatial resolution of the measurement means applied for measuring the said first and second indicator as will readily be appreciated by the skilled person working with medical imaging techniques. Working for example with magnetic resonance imaging (MRI) will currently yield a spatial resolution in the order of sub-millimetres, whereas some optical detection techniques, e.g. two-photon microscopy imaging, are strictly speaking only limited by the diffraction limit (~λ/2), this limit being typically smaller than the spatial extension of a single capillary and thus measuring or averaging over more capillaries may be necessary.

Depending on the measurement technique applied for implementing the present invention, the flow of blood, and the heterogeneity thereof in the capillary bed, may therefore be derived from flows measured on various spatial dimensions. Thus, for some measurement techniques, the scale will be close to a single particle within the blood in a vessel (and hence average flow and heterogeneity requires more than one measurement), whereas other measurement techniques will essentially be measured on a spatial scale of many capillaries. As it will be appreciated by the skilled person in medical imaging, every imaging modality has an effective voxel size that should be adapted and/or compensated for when implementing the present invention in practise. Notice, in particular that medical imaging applying contrast agents (e.g. isotopes in MRI, radioisotopes in SPECT and PET or microbubbles in ultrasonic imaging) requires specific consideration with respect to the effective voxel size. Thus, depending on the tissue being examined and/or the imaging technique, the physical extension of capillary bed may be in the range of 50-2000 micrometer, preferably 100-1000 micrometers, more preferably 200-500 micrometers.

In the present context, the term "extraction capacity (EC)" refers to the fraction of a substance that can be extracted from arterial blood.

In the present context, the term "total substance concentration ($C_T$ or C in brief)" refers to the total concentration of the substance of interest in all of its forms present in the blood; e.g. the sum of non-bound substance in the plasma+ substance bound to serum protein+substance contained in the blood cells.

In one embodiment of the present invention, the model further includes a non-vanishing back flow of the substance from the tissue into the capillaries. Thus, the back flow may be non-negligible, or significantly above zero.

In another embodiment of the present invention, the first indicator is related to a mean transit time (MTT) of the blood flow through a capillary bed, and the second indicator is related to the standard deviation ($\sigma$) of the mean transit time of the blood flow.

In yet another embodiment of the present invention, the first indicator is related to a mean velocity of particles, and the second indicator is related to the standard deviation ($\sigma$) of particle velocities in the blood flow.

In the present context, the term "particle" refers to any molecule or amount of molecules (such as a gas bubble) being transported by the blood, or any blood cell, such as a red blood cell.

In another embodiment of the present invention, the first indicator is related to a mean transit time (MTT) of the blood flow, and the second indicator is related to the standard deviation ($\sigma$) of the mean transit time of the blood flow.

In yet another embodiment of the present invention, the model is based on at least one rate constant, k, related to the permeability of the capillary wall to the substance. The rate constant, k, may describe two directions, i.e., from the capillaries to the tissue and from the tissue to the capillaries.

In the present context, the term "capillary wall" refers to the capillary wall comprising endothelial cells, a basement membrane, and surrounding cells called pericytes. The capillary wall may have undergone structural changes or deposits (amyloid etc).

Blood is a specialized bodily fluid that delivers necessary substances to the tissues cells, such as nutrients and oxygen, and transports waste products, excess nutrients and excess oxygen away from e.g. those same cells. In mammals, blood is composed of blood cells suspended in a liquid called blood plasma. Blood plasma is blood minus the blood cells. It comprises water, dissipated proteins (serum proteins), glucose, mineral ions, hormones and carbon dioxide. The blood cells present in blood are mainly red blood cells (also called RBCs or erythrocytes), white blood cells and platelets. The most abundant cells in mammal blood is the red blood cell. These contain haemoglobin, an iron-containing protein, which facilitates transportation of oxygen by reversibly binding to this respiratory gas and greatly increasing its solubility in blood. In contrast, carbon dioxide is almost entirely transported extracellularly dissolved in plasma as bicarbonate ions.

In the present context, the term "substance" refers to any molecule being transported by the blood, such as oxygen, lactate, insulin, nutrients (e.g. glucose), drugs, and signal molecules (e.g. NO, and various hormones).

Figure 9:
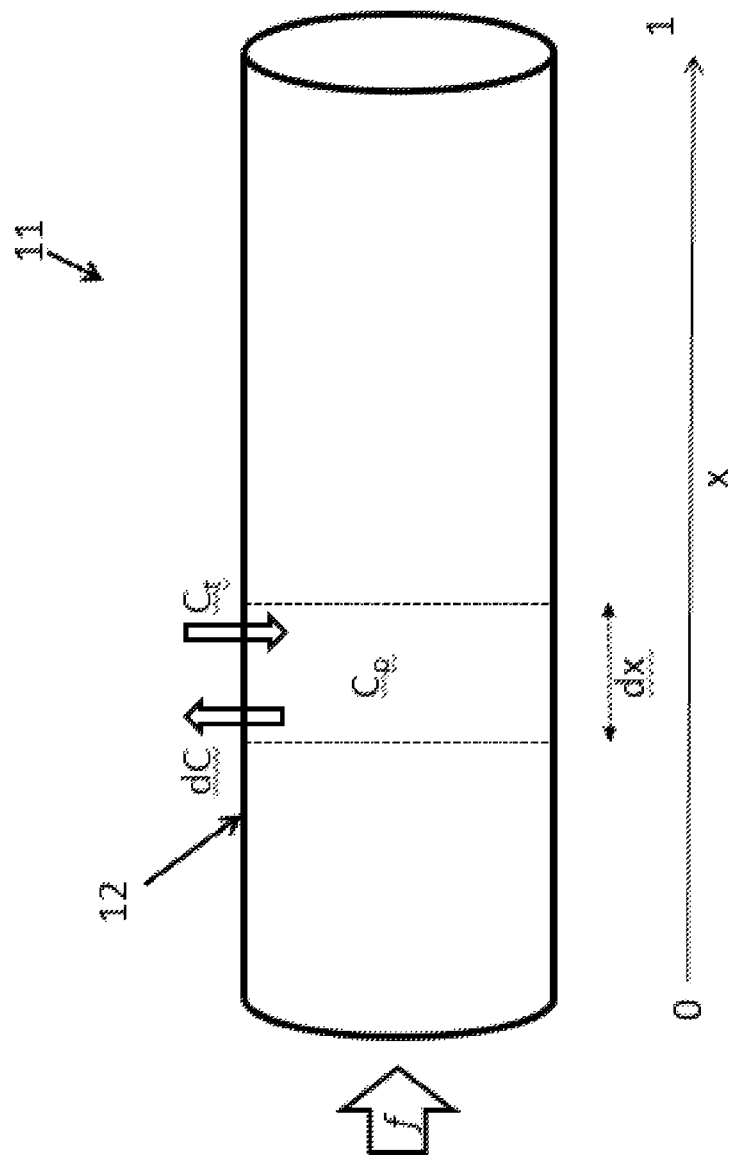
FIG. 9 is a schematic drawing of a capillary showing various elements in the modelling of the extraction capacity.

For a general substance, the inventors of the present invention consider first a single capillary (11) of length L and volume V (FIG. 9), assuming that the substance inside the capillary is well stirred along the radial direction, and that the current of substance across the capillary wall is proportional to the difference between plasma concentration of the substance ($C_P$) and tissue concentration of the substance ($C_t$). The differential equation for total substance concentration C as a function of the fractional distance $x \in [0,1]$ along a capillary with flow f and volume V then reads $$\frac{dC}{dx} = -\frac{kV}{f}(C_p - C_t).$$

Here, the inventors are assuming equal forward and reverse rate constants k of the substance across the capillary barrier (12) for simplicity. However, the model applied in the present invention may readily be extended to the situation where the forward and reverse rate constants are different from each other. Note that the capillary transit time $\tau$ is identical to V/f.

In one embodiment of the present invention, the model applies a variable shift to $k\tau$ x-domain enabling averaging over a transit time distribution to be performed from one capillary, k being the rate constant for diffusion of the substance across the capillary, $\tau$ being the mean transit time, and x being the fractional distance of the capillary.

In a single capillary with transit time $\tau$ and transfer constant k, the oxygen concentration C as a function of fractional distance x along the capillary may be described by the differential equation $$\frac{dC}{dx} = -k\tau\left(\alpha_H P_{50}\left(\frac{C}{B-C}\right)^{1/h} - C_t\right).$$

Note that oxygen concentration then depends on three variables: $C=C(x; k,\tau)$. The oxygen extraction fraction $OEC_1$ for a single capillary with arterial concentration $C_A=C(0; k, \tau)$ is defined by:

$$OEF_1 = 1 - C(1;k,\tau)/C_A.$$

To compute the extraction fraction OEC for a collection of capillaries with a distribution $h(\tau)$ of transit times, we need to average this equation over many capillaries, and this will involves the integral $$\int d\tau h(\tau) C(1;k,\tau).$$

This is time consuming, since the differential equation will need to be solved for a large number of transit times in order to compute the integral above. This is assuming k is already known: to calibrate for k, we need to repeat the entire process for a range of k values and match OEC to PET-OEF.

However, by noticing the structure of the differential equation, one realizes that the concentration does not depend on the three variables individually, only on their product $C(x; k, \tau) = f(kx\tau)$. Here f is a function obeying $$\frac{df}{dy} = -\left(\alpha_H P_{50}\left(\frac{f}{B-f}\right)^{1/h} - C_t\right)$$

Now this differential equation does not depend on k or $\tau$ and thus needs to be solved numerically only once, giving $f$ as a function of $kx\tau$. Therefore we can make a change of variables in the integral, from $\tau$ to $y = kx\tau$ (with $x=1$) to obtain $$\int_0^\infty d\tau h(\tau) C(1;k,\tau) = \int_0^\infty dy f(y) h(y/k) \frac{1}{k}$$

When h is gamma-variate with parameters $\alpha$ and $\beta$, $h(y/k)/k$ corresponds to a gamma-variate with parameters $\alpha$ and $k\beta$. For suitable parameterizations of $f$, the integral can be carried out analytically, and it is thus easy to compute OEC for any given value of k given a significant advantage upon implementation.

In general one have $$C_T = C_P + C_B,$$

where $C_B$ is the concentration of substance in blood not freely dissolved in plasma, e.g. bound to a plasma protein. One needs to have a relation for $C_B$ for solving, analytically or numerically, the differential equation applied in the present invention.

In a first variant of the present invention, the substance is oxygen ($O_2$):

Oxygen exists as bound to haemoglobin (cooperative binding or non-linearly binding) and as freely dissolved in plasma. For oxygen one may then approximate the plasma concentration of oxygen by:

$$C_P \cong \alpha_H P_{50}(C_T/(B-C_T))^{1/h}$$

using the Hill-equation. This is described in more detail in the examples section below.

In another embodiment of the present invention, the model further includes substance cooperativity due to a non-linear binding of the substance with a protein in the blood.

In yet another embodiment of the present invention, the substance is oxygen and the model includes oxygen cooperativity due to the non-linear binding of oxygen with haemoglobin.

In still another embodiment of the present invention, the substance is oxygen and the extraction capacity is oxygen extraction capacity (OEC).

In still another embodiment of the present invention, the substance is glucose and the extraction capacity is glucose extraction capacity.

In still another embodiment of the present invention, the substance is insulin and the extraction capacity is insulin extraction capacity.

In a second variant of the present invention, the substance is a drug (A):

The drug A is freely dissolved in plasma or bound to a plasma protein P as described by the biochemical equilibrium:

$$A + P \leftrightarrow AP$$

Where AP denotes the configuration where the drug A is bound to the protein P. Using square brackets for concentrations, one has the following relations:

$$C_P = [A]$$

$$C_T = [A] + [AP]$$

Assuming Langmuir binding kinetics, one has $$([P] + [AP])\frac{K[A]}{1 + K[A]} = [AP], \text{ and } [AP] = C - C_p$$

where K is the binding constant. Thus, $C_p$ can be expressed in terms of the total concentration C and the protein content given by $[P] + [AP]$.

A drug's binds to the proteins within blood plasma (plasma proteins). Common blood proteins that drugs bind to are human serum albumin, lipoprotein, glycoprotein, $\alpha$, $\beta$, and $\gamma$ globulins. This means that there are two populations of molecules, where only the free pool can directly cross the capillary wall. In the creation for the extraction faction, one would thus need a relation between total substance concentration and free substance concentration. This could involve e.g. the Langmuir equation.

In a third variant of the present invention, the substance is a drug (A) binding to a protein with multiple binding sites, each with a corresponding binding constant, $K_i$, for $i=1$ to the maximum number of binding sites n:

$$A_1 + P \leftrightarrow PA_1; K_1$$
$$A_2 + P \leftrightarrow PA_2; K_2$$
$$\ldots$$
$$A_n + P \leftrightarrow PA_n; K_n$$

Using the binding polynomial $$Q = \Sigma_{i=0}^n K_i x^i = \Sigma_{i=0}^n K_i [A]^i, \text{ with } [A] = x$$

The average number of molecules bound per protein, v, is then given by:

$$v = \frac{d\ln Q}{d\ln x} = \frac{X}{Q}\frac{dQ}{dx}$$

resulting in the so-called binding curve.

If the protein concentration is known as $C_{prot}$, the concentration of bound drug A is $v \cdot C_{prot}$. This can be expressed in terms of $C_p$ and C since one has:

$$C - C_p = v C_{prot}$$

Binding curves, i.e. relating v to x also include other cases readily available to the skilled person, for example the Hasher and von Hippel model where ligands 'crowd' each other out as expressed by $$\frac{v}{x} = K(1-nv)\left[\frac{1-nv}{1-(n-1)v}\right]^{(n-1)}$$

where n is the number of sites occupied by one ligand.

Returning to the case where the substance is oxygen, the Hill equation can be considered a special case where $$Q = 1 + Kx^h.$$

The Adair equation can then be considered a refined model of oxygen binding with $$Q = 1 + 4K_1 x + 6K_2 x^2 + 4K_3 x^3 + K_4 x^4$$

Similarly, the familiar Pauli model may be applied within the context of the present invention with $$Q = 1 + 4Kx + 6(Kx)^2 f + 4(Kx)^3 f^3 + (Kx)^4 f^6$$

where $f = \exp(-\epsilon_0/k_B T)$.

Alternatively, in the MWC Allosteric Model the binding polynomial can be expressed as $$Q = \frac{1}{1+L}((1+K_R x)^4 + L(1+K_T x)^4)$$

where L, and $K_R/K_T$ are equilibrium constants.

In one embodiment of the present invention, the means for measuring the first indicator (MTT) for the blood flow through a capillary bed and/or for measuring the second indicator of heterogeneity (σ) of the blood flow in said capillary bed are measurement means based on direct in-vivo measurement of the distribution of particle velocities, particle flux, and/or particle transit times.

In one variant, the means for measuring the first indicator (MTT) for the blood flow through a capillary bed and/or for measuring the second indicator of heterogeneity (σ) of the blood flow in said capillary bed are measurement means may be based on direct in-vivo measurement of the distribution of particle velocities, particle flux, and/or particle transit times. The concept of direct measurement is primarily related to the measurement techniques having a spatially resolution that enables direct observation of individual particles, or small groups of particles, these techniques are mainly based on optical principles. The concept of optical may include detecting of radiation in the visible light range, but also in the infrared (IR) and in the ultraviolet (UV) ranges, possible even further.

The direct measurement means may, for example, be multiple-photon spectroscopic methods, including two-photon spectroscopy, cf. Chaigneau et al. (2003). Alternatively, it may be based on confocal imaging methods, cf. Villringer et al., 1994 for further details. Laser Doppler measurements, e.g. laser flowmetry, may also provide a suitable platform for implementing the present invention.

Direct measurement may also include laser scanning optometry of retina, cf. international patent application, WO 2008/117338. The area of retinal angiography may further be beneficially be applied in the context of the present invention, including sub-techniques like:
scanning laser ophthalmoscopy,
laser Doppler flow metry,
adaptive optics retinal scanning, and image (or video) recordings that enable the measurement of vascular diameters.

Retina measurements provide an advantageous and direct way of measuring the first and second indicators according to the present invention, including the effect of a possible drug, or a level of drug.

In still another embodiment of the present invention, the direct measurement means is chosen from the group consisting of: multiple-photon spectroscopic methods, including two-photon imaging, confocal imaging, laser Doppler measurements, and laser scanning optometry of retina, light microscopy, Orthogonal Polarization Spectral (OPS) imaging, Sidestream dark-field (SDF) imaging and any combinations thereof.

In another variant, the invention may relate to means for measuring the first indicator (MTT) for the blood flow through a capillary bed and/or for measuring the second indicator of heterogeneity (σ) of the blood flow in said capillary bed are measurement means based on in-direct in-vivo measurement of the distribution of particle velocities, particle flux, and/or particle transit times. Such means are typically based on one or more measurements having a spatial dimensions larger than a typical capillary dimension. The in-direct means may also apply contrast agents so that the performed measurement is dependent on contrast agents, and its interaction with the tissue being measured upon.

The in-direct measurement means may, for example, be nuclear magnetic resonance imaging (MRI) and positron emission tomography (PET), for further details on the experimental techniques relevant for the present invention cf. also U.S. Pat. No. 7,069,068 (owned by one of the present inventors, Leif Østergaard) and references cited therein. Alternatively, the in-direct means may include single photon emission computed tomography (SPECT) and. computed tomography (CT).

A particular advantageous measurement means include ultrasonic methods (also called medical soniography) using sound waves above 20 kHz for imaging, in particular perfusion measurements. Various ways of performing this include contrast-enhanced ultrasonic (CEU) techniques and Doppler based techniques. For more details on implementing the present invention using ultrasonic means, the skilled reader is referred for example to Digital techniques in echocardiography by Joe Rolandt, Springer, 1987, for more details about perfusion measurement using ultrasonic methods.

Needles to say, the present invention may possibly be implemented in any combinations of the above-mentioned techniques.

In yet another embodiment of the present invention, the means for measuring the first indicator (MTT) for the blood flow through a capillary bed and/or for measuring the second indicator of heterogeneity (σ) of the blood flow in said capillary bed are measurement means based on in-direct in-vivo measurement of the distribution of particle velocities, particle flux, and/or particle transit times.

In another embodiment of the present invention, the indirect measurement means is chosen from the group consisting of: nuclear magnetic resonance imaging (MRI), positron emission tomography (PET), single photon emission computed tomography (SPECT), computed tomography (CT), ultrasonic methods, and any combinations thereof.

Two main categories of magnetic resonance imaging (MRI) techniques may be used to measure tissue perfusion in vivo. The first is based on the use of injected contrast agent that changes the magnetic susceptibility of blood and thereby the MR signal which is repeatedly measured during bolus passage. The other category is based on arterial spin labelling (ASL), where arterial blood is magnetically tagged before it enters into the tissue of interest and the amount of labelling is measured and compared to a control recording obtained without spin labelling.

The inventors have derived a general expression for oxygen transport into tissue as a function of capillary transit time heterogeneity (CTTH), and show that biophysically, CTTH profoundly affects the oxygen extraction capacity (OEC; the fraction of oxygen that can be extracted from arterial blood) for a given blood flow and blood volume. In vivo measurements of transit time characteristics, available from studies in rat brain, show that CTTH homogenization account for at least 50% of the change in available oxygen, and thus seem crucial to brain normal function across a range of physiological challenges. The model predicts devastating effects of capillary flow disturbances that increase CTTH relative to the blood transit time. This phenomenon will be discussed below in relation to observations of endothelial swelling and morphological changes in the basement membranes and pericytes in a range of diseases.

Figure 2:
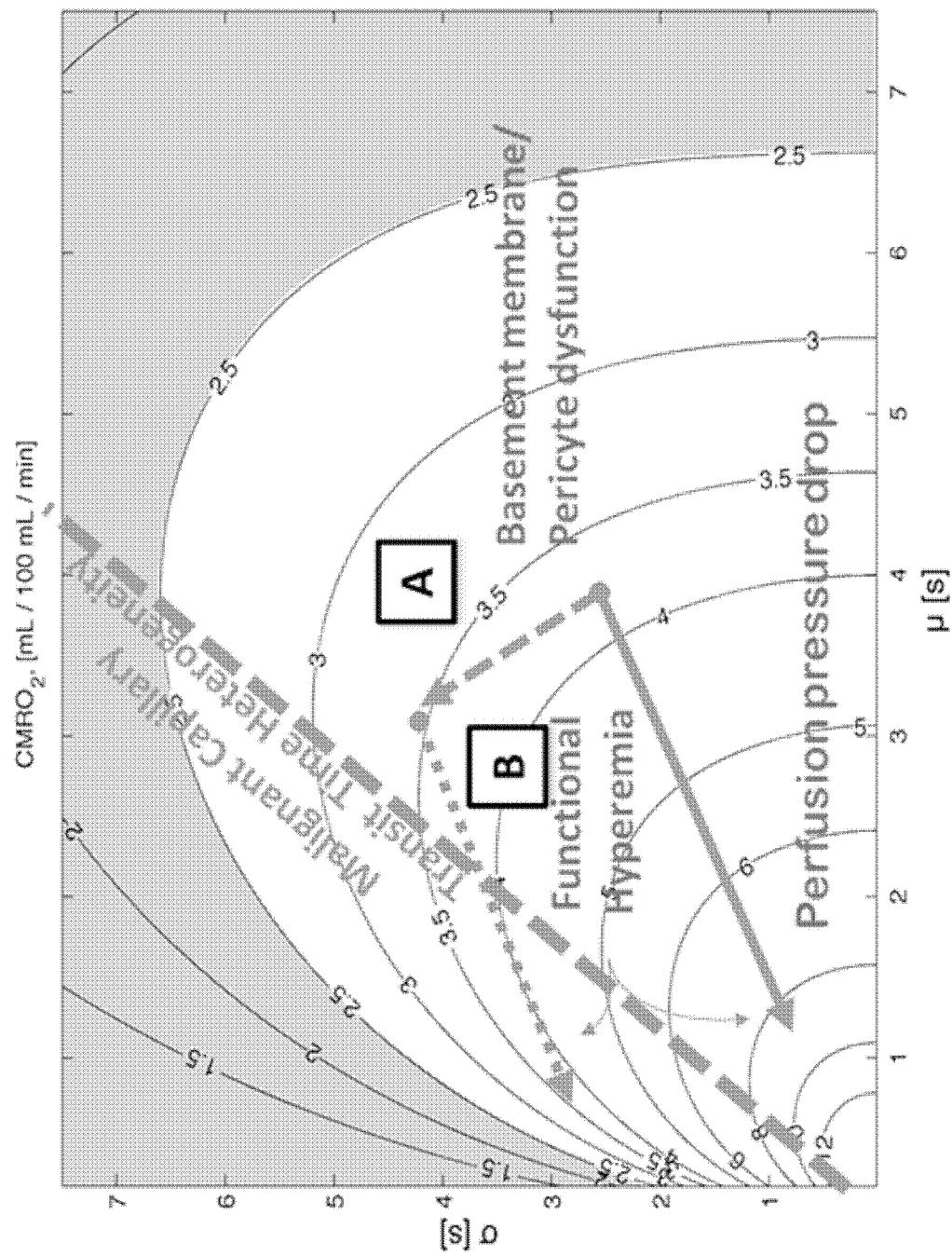
FIG. 2 shows the metabolic effects of functional or active hyperemia in case of microvascular flow disturbances owing to basement membrane thickening, endothelial or pericapillary edema or changes in pericyte morphology, all of which may disturb capillary patency and therefore capillary flow dynamics.

As an example, the inventors propose (in a non-limiting manner) the following links between microvascular hemodynamic derangement, and metabolic impairment and death of cells; here exemplified in FIGS. 1 and 2:

FIG. 1 shows the metabolic effects of tissue reperfusion in case of reversible and irreversible capillary flow disturbances. FIG. 1 has been modified such that the $CMRO_2$ threshold (less than 2.5 mL/100 mL/min) for irreversible tissue damage is highlighted in grey. In acute ischemia, the perfusion pressure drop cause acute increase in the CBV/CBF ratio.

A: During ischemia, endothelial edema and chronic constriction of pericytes develop (Yemisci et al., 2009), seemingly paralleled by an increase in CTTH heterogeneity (Tomita et al., 2002).

B: As tissue is reperfused, the patency of capillaries may be restored (lower arrow), or, as demonstrated by Yemisci, remain disturbed (upper arrow). In the latter case, the microcirculation may enter a state of malignant CTTH, in which tissue oxygenation is not restored despite normal CBF. Instead, tissue hypoxia/acidosis will tend to stimulate upstream vasodilation, which further impairs oxygenation—explaining the luxury perfusion syndrome (Lassen, 1966).

C: According to the model, oxygenation levels do not become critically low during luxury perfusion. Theoretically, the pharmacological normalization of capillary patency reported by Yemisci could hence normalize tissue oxygenation. Of note, the notion that post-ischemic hyperperfusion represents tissue that may be salvageable by such 'microciculatory recanalization' applies for all tissue types. Note that this theory explains the poor outcome of tissue ischemia in patients with degenerative diseases, and therefore microangiopathies with 'chronic' high CTTH (diabetes, hypertension and other cardiovascular risk factors. The same principle applies to patients with critical illness (septic shock), in which micovascular failure develops. This results in increasing hypoxia, and adverse effects of resuscitation (e.g. CardioPulmonary Resuscitation, CPR). The success of hypervolemic therapy likely owes to maintaining capillary patency by plasma 'overload'.

FIG. 2 show the metabolic effects of functional or active hyperemia in case of microvascular flow disturbances owing to basement membrane thickening, endothelial or pericapillary edema or changes in pericyte morphology (cf. microangiopathies in hypertension, diabetes, Alzheimer's Diseases, and in angiogenesis and Moya-moya-disease).

A: Degenerative diseases such as diabetes, chronic hypertension and Alzheimer's Disease cause profound changes in capillary basement membrane thickness, pericyte morphology (Diaz-Flores et al., 2009; Hamilton et al., 2010) and capillary patency (Bell et al., 2010), leading to increase, resting CTTH. Likewise, angiogenesis cause 'chaotic' capillary paths with wide CTTH distributions (Observed so far in Alzheimer's Disease and diabetes).

B: During 'normal' tissue activation, functional/active hyperemia and CTTH reduction support additional oxygen metabolism (lower arrow. If local disturbances of capillary flows are irreversible, functional/active hyperemia (upper arrow) no longer leads to increased tissue oxygenation, possibly affecting neuronal cell and/or tissue function, and—if CTTH increase to such extent that normal perfusion or functional hyperemia is associated with hypoxia—neuronal survival.

Functional hyperemia, or active hyperemia, is the increased blood flow that occurs when tissue is active.

Reactive hyperemia is the transient increase in organ blood flow that occurs following a brief period of ischemia.

Moyamoya syndrome is a disease in which certain arteries in the brain are constricted. Blood flow is blocked by the constriction, and also by blood clots (thrombosis).

In the present context, the term "ischemia" refers to a restriction in blood supply, generally due to factors in the blood vessels, with resultant damage or dysfunction of tissue (e.g. myocardial ischemia).

In the present context, the term "circulatory shock (also known as "shock")", refers to perfusion of tissues which is insufficient to meet cellular metabolic needs. As the blood carries oxygen and nutrients around the body, reduced flow hinders the delivery of these components to the tissues, and can stop the tissues from functioning properly. The process of blood entering the tissues is called perfusion, so when perfusion is not occurring properly this is called a hypoperfusional state or hypoperfusion.

In the present context, the term "hypoxia" refers to a condition in which the body as a whole (generalized hypoxia) or a region of the body (tissue hypoxia, e.g. cerebral hypoxia or hypoxia in the heart) is deprived of adequate oxygen supply.

Prolonged hypoxia induces cell death via apoptosis resulting in a hypoxic injury.

Cerebral hypoxia refers to reduced brain oxygen, and can be classified as follows:

1. Hypoxic hypoxia is a situation where limited oxygen in the environment causes reduced brain function. The term also includes oxygen deprivation due to obstructions in the lungs. Choking, strangulation, the crushing of the windpipe all cause this sort of hypoxia. Severe asthmatics may also experience symptoms of hypoxic hypoxia.

2. Hypemic hypoxia is a situation where reduced brain function is caused by inadequate oxygen in the blood despite adequate environmental oxygen. Anemia and carbon monoxide poisoning are common causes of hypemic hypoxia.

3. Ischemic hypoxia (also known as stagnant hypoxia) is a situation where reduced brain oxygen is caused by inadequate blood flow to the brain. Stroke, shock, and heart attacks are common causes of ischemic hypoxia. Ischemic hypoxia can also be created by pressure on the brain. Cerebral edema, brain hemorrhages and hydrocephalus exert pressure on brain tissue and impede their absorption of oxygen.

4. Histotoxic hypoxia. Oxygen is present in brain tissue but cannot be metabolized. Cyanide poisoning is a well-known example.

In the present context, the term "stroke" refers to the rapidly developing loss of brain function(s) due to disturbance in the blood supply to the brain. This can be due to ischemia (lack of blood flow) caused by blockage (thrombosis, arterial embolism), or a hemorrhage (leakage of blood). As a result, the affected area of the brain is unable to function.

Silent stroke is a stroke (infarct) which does not have any outward symptoms (asymptomatic), and the patient is typically unaware they have suffered a stroke. Despite not causing identifiable symptoms a silent stroke still causes damage to the brain, and places the patient at increased risk for a major stroke in the future. Silent strokes typically cause lesions which are detected via the use of neuroimaging such as MRI.

In the present context, the term "reperfusion injury" refers to tissue damage caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signalling to turn on apoptosis. Leukocytes may also build up in small capillaries, obstructing them and leading to more ischemia.

Perhaps the most central paradigm in physiology states that organs and tissues secure their supply of nutrients by adjusting arterial and arteriolar tone, and thereby local blood flow. Capillaries, in turn, bring blood in intimate contact with tissue, allowing diffusion to nearby cells. Having demonstrated this diffusive transport, Danish physiologist August Krogh argued that capillaries may themselves regulate the total supply of nutrients to tissue by capillary recruitment: Opening of previously closes capillaries, thereby increasing the organ's total capillary surface area available for diffusion, and hence oxygen extraction. While capillary recruitment is believed to occur in muscle tissue, it has been ruled out in most other organs. Instead, direct observation of red blood cell (RBC) transits through the capillary bed show extreme spatiotemporal heterogeneity, with characteristic changes during physiological challenges such as neural activity, decreased perfusion pressure and hypoxia, and in diseases such as ischemia and critical illness. The physiological role of this capillary transit time heterogeneity (CTTH) and of the contractile capillary pericyte, the cell type found by Krogh and colleagues to adjust capillary flows, however, remains unknown.

In the present context, the term "hypotension" refers to abnormally low blood pressure, i.e. a mean arterial blood pressure (MABP) below 80 mmHg for an adult human, and below 100 mmHg for an adult rat. Hypotension may be associated with shock. In the present context, the term "Hemorrhagic hypotension" refers to hypotension as a result from blood loss.

In the present context the term "neurodegenerative" refers to the progressive loss of structure or function of neurons, including death of neurons. Neurodegenerative diseases including Parkinson's, Dementia, Alzheimer's, multiple sclerosis, and Huntington's occur as a result of neurodegenerative processes.

In the present context, the term "Parkinson's disease" refers to a degenerative disorder (neurodegenerative disease) of the central nervous system that impairs motor skills, cognitive processes, and other functions. The most obvious symptoms are motor-related, including tremor, rigidity, slowness of movement, and postural instability. Among non-motor symptoms are autonomic dysfunction and sensory and sleep difficulties. Cognitive and neurobehavioral problems, including dementia, are common in the advanced stages of the disease. PD usually appears around the age of 60, although there are young-onset cases.

In the present context the term "early detection of Parkinson's disease" refers to detection before the onset of clinical symptoms (bradykinesia, tremor, postural instability and rigidity). At this stage 50-80 percent of the dopamine-producing neurons have degenerated. If it were possible to detect the disease earlier, neuron-protective strategies could be exploited to delay the onset of PD. Thus, "early detection of Parkinson's disease" is also to be understood as detection before 50%, such as before 60%, such as before 70%, or such as before 80% of the dopamine-producing neurons have degenerated.

Dementia is a non-specific illness syndrome (set of signs and symptoms) in which affected areas of cognition may be memory, attention, language, and problem solving. It is normally required to be present for at least 6 months to be diagnosed. Cognitive dysfunction that has been seen only over shorter times, in particular less than weeks, must be termed delirium. In all types of general cognitive dysfunction, higher mental functions are affected first in the process.

Various types of brain injury, occurring as a single event, may cause irreversible but fixed cognitive impairment. Traumatic brain injury may cause generalized damage to the white matter of the brain (diffuse axonal injury), or more localized damage (as also may neurosurgery). A temporary reduction in the brain's supply of blood or oxygen may lead to hypoxic-ischemic injury. Strokes (ischemic stroke, or intracerebral, subarachnoid, subdural or extradural hemorrhage) or infections (meningitis and/or encephalitis) affecting the brain, prolonged epileptic seizures and acute hydrocephalus may also have long-term effects on cognition. Excessive alcohol use may cause alcohol dementia, Wernicke's encephalopathy and/or Korsakoff's psychosis, and certain other recreational drugs may cause substance-induced persisting dementia; once overuse ceases, the cognitive impairment is persistent but not progressive.

In the present context, the term "multiple sclerosis" refers to an inflammatory disease in which the fatty myelin sheaths around the axons of the brain and spinal cord are damaged, leading to demyelination and scarring as well as a broad spectrum of signs and symptoms.

In the present context, the term "neoplasm" is an abnormal mass of tissue as a result of neoplasia. Neoplasia is the abnormal proliferation of cells. The growth of neoplastic cells exceeds and is not coordinated with that of the normal tissues around it. The growth persists in the same excessive manner even after cessation of the stimuli. It usually causes a lump or tumor. Neoplasms may be benign, pre-malignant (carcinoma in situ) or malignant (cancer). In the present context, the term "malignant tumor" refers to "malignant neoplasm".

In the present context, the term "carcinoma" refers to an invasive malignant tumor consisting of transformed epithelial cells. Alternatively, it refers to a malignant tumor composed of transformed cells of unknown histogenesis, but which possess specific molecular or histological characteristics that are associated with epithelial cells, such as the production of cytokeratins or intercellular bridges.

In the present context, the term "sarcoma" refers to a cancer that arises from transformed connective tissue cells. These cells originate from embryonic mesoderm, or middle layer, which forms the bone, cartilage, and fat tissues. For example, osteosarcoma arises from bone, chondrosarcoma arises from cartilage, and leiomyosarcoma arises from smooth muscle, and soft tissue sarcoma refers to tumors of soft tissue.

Malignant tumors of the male reproductive organs include, but are not limited to prostate and testicular cancer. Malignant tumors of the female reproductive organs include, but are not limited to endometrial, cervical, ovarian, vaginal, and vulvar cancer, as well as sarcoma of the uterus.

Malignant tumors of the digestive tract include, but are not limited to anal, colon, colorectal, esophageal, gallbladder, gastric, pancreatic, rectal, small-intestine, and salivary gland cancers.

Malignant tumors of the urinary tract include, but are not limited to bladder, penile, kidney, renal pelvis, ureter, and urethral cancers.

The predetermined reference value(s) or levels of the extraction capacity may be determined by any suitable statistical method. Receiver operating characteristic (ROC) curve analysis is a classification model for a mapping of instances into a certain class/group. Receiver operating characteristic (ROC) curve analysis may be used determine the classifier boundary between groups of patients for which the classifier boundary between classes must be determined by a threshold value, for instance to determine whether a person is likely to have a disease (e.g. Parkinsons disease) or if a patient is likely to respond to a treatment or not.

In one embodiment of the present invention, the processor is further arranged for assessing one, or more, of the first indicator, the second indicator, and the extraction capacity with a database comprising reference values thereof.

In another embodiment of the present invention, the system further comprises a database with references levels of one, or more, of the first indicator, the second indicator and the extraction capacity for one or more subjects with:
shock, including circulatory and septic shock;
stroke;
hypoxia;
ischemia, including myocardial and renal ischemia, and reperfusion injury in any organ;
hypoperfusional states;
Sickle cell disease
hypotension, including hemorrhagic hypotension;
cancer, including malignant tumors;
diabetes and obesity;
hypertension
systemic autoimmunes diseases including systemic sclerosis
virus related encephalopathy
psychiatric disorders associated with chronic inflammation, such as depression, schizophrenia, ADHD and autism, aging; or
neurodegenerative diseases, including Alzheimer's disease and other dementias, Parkinson's disease, Huntington's Disease and multiple sclerosis.

The different reference levels may further be divided in groups according to age, sex/gender, degree of condition, pre-clinical stage etc.

One aspect of the present invention relates to the use of the system for monitoring the possible effect of a substance (e.g. an active pharmaceutical ingredient (API)) or a composition (e.g. one or more active pharmaceutical ingredients and one or more excipients) on the micro-vascular flow distribution of a tissue portion of a mammal.

In the present context, the term "active pharmaceutical ingredient (API)" refers to any substance that is biologically active.

In the present context, the term "excipient" refers to the substance of the tablet, or the liquid the API is suspended in.

Another aspect of the present invention relates to a database comprising references levels of one, or more, of the first indicator, the second indicator and the extraction capacity for one or more subjects with:
shock, including circulatory and septic shock;
stroke;
hypoxia;
ischemia, including myocardial and renal ischemia, and reperfusion injury in any organ;
hypoperfusional states;
Sickle cell disease
hypotension, including hemorrhagic hypotension;
cancer, including malignant tumors;
diabetes and obesity;
hypertension
systemic autoimmunes diseases including systemic sclerosis
virus related encephalopathy
psychiatric disorders associated with chronic inflammation, such as depression, schizophrenia, ADHD and autism, aging; or
neurodegenerative diseases, including Alzheimer's disease and other dementias, Parkinson's disease, Huntington's Disease and multiple sclerosis.

Figure 10:
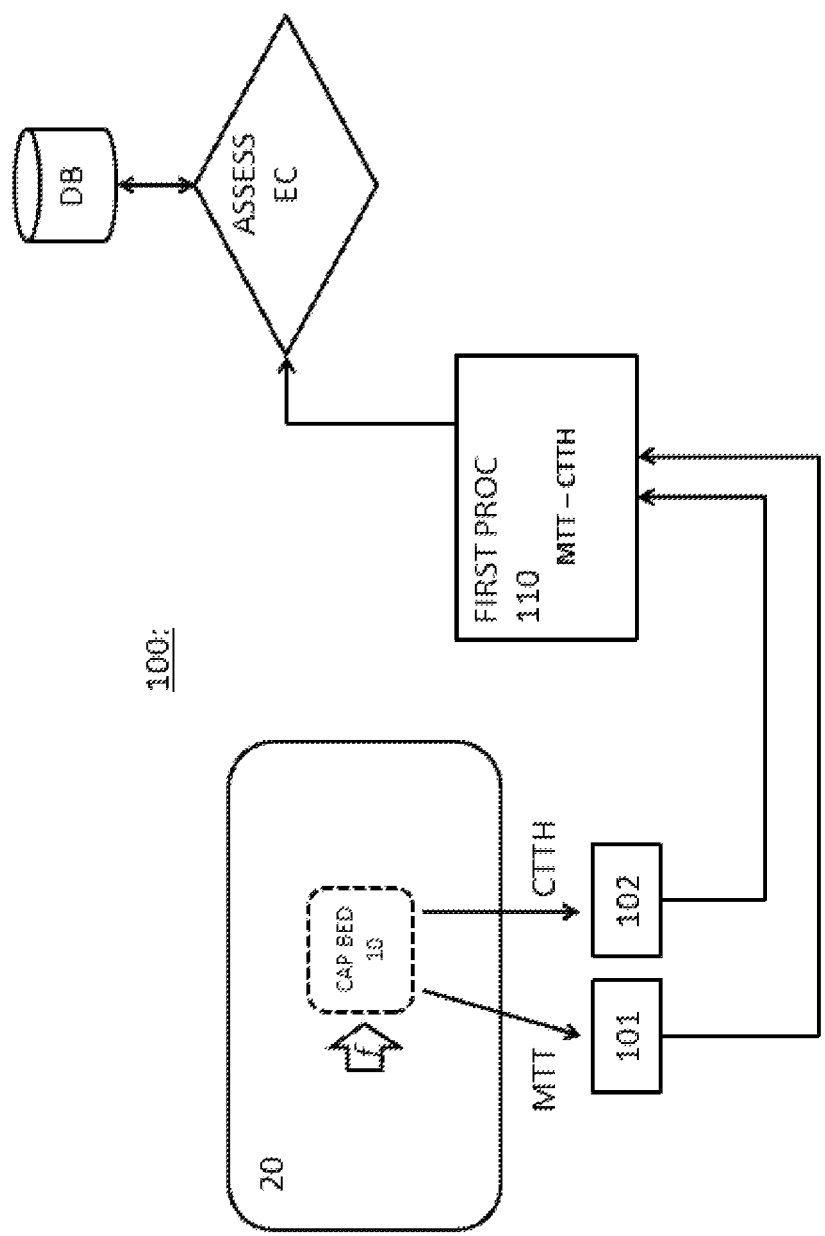
FIG. 10 is a schematic drawing with a system for measuring a micro-vascular flow distribution of a tissue portion of a mammal according to the present invention.

FIG. 10 is a schematic drawing with a system 100 for measuring a micro-vascular flow distribution of a tissue portion of a mammal according to the present invention. The system comprises:
means 101 for measuring a first indicator for the blood flow through a capillary bed 10;
means 102 for measuring a second indicator of heterogeneity of the blood flow in said capillary bed;
a first processor 110 arranged for using the first and the second indicator to estimate an extraction capacity (EC) of a substance from the blood in said capillary bed;
wherein the first processor applies a model connecting the first and the second indicator to the extraction capacity (EC) of a substance from the blood in said capillary bed, the model comprising the transfer rate of total substance concentration ($C_T$) across the capillaries being linearly dependent on the plasma concentration of the substance ($C_P$), the model further having a non-vanishing back flow of the substance from the tissue into the capillaries.

In FIG. 10, the means 101, or modality, for measuring a first indicator for the blood flow through the capillary bed 10; and the means 102, or modality for measuring a second indicator of heterogeneity of the blood flow in said capillary bed 10, are schematically indicated as separate entities purely for illustrative reasons, thus for some embodiments the means could be the same means, e.g. for DSC-MR measurements are recorded, yielding inter alia the arterial input function (AIF), that could be used for mathematically obtaining both the first indicator, e.g. MTT, and the second indicator, e.g. CTTH, under the relevant assumptions, c.f. separate discussions.

Similarly, for an optical based measurement, optical irradiation, e.g. by laser, and subsequent optical detection could be common for the means 101 and 102, the data being processed different to obtain the first and second indicator, respectively. However, others optical based measurement may have separate means, or modalities, for obtaining the first and second indicators.

Figure 11:
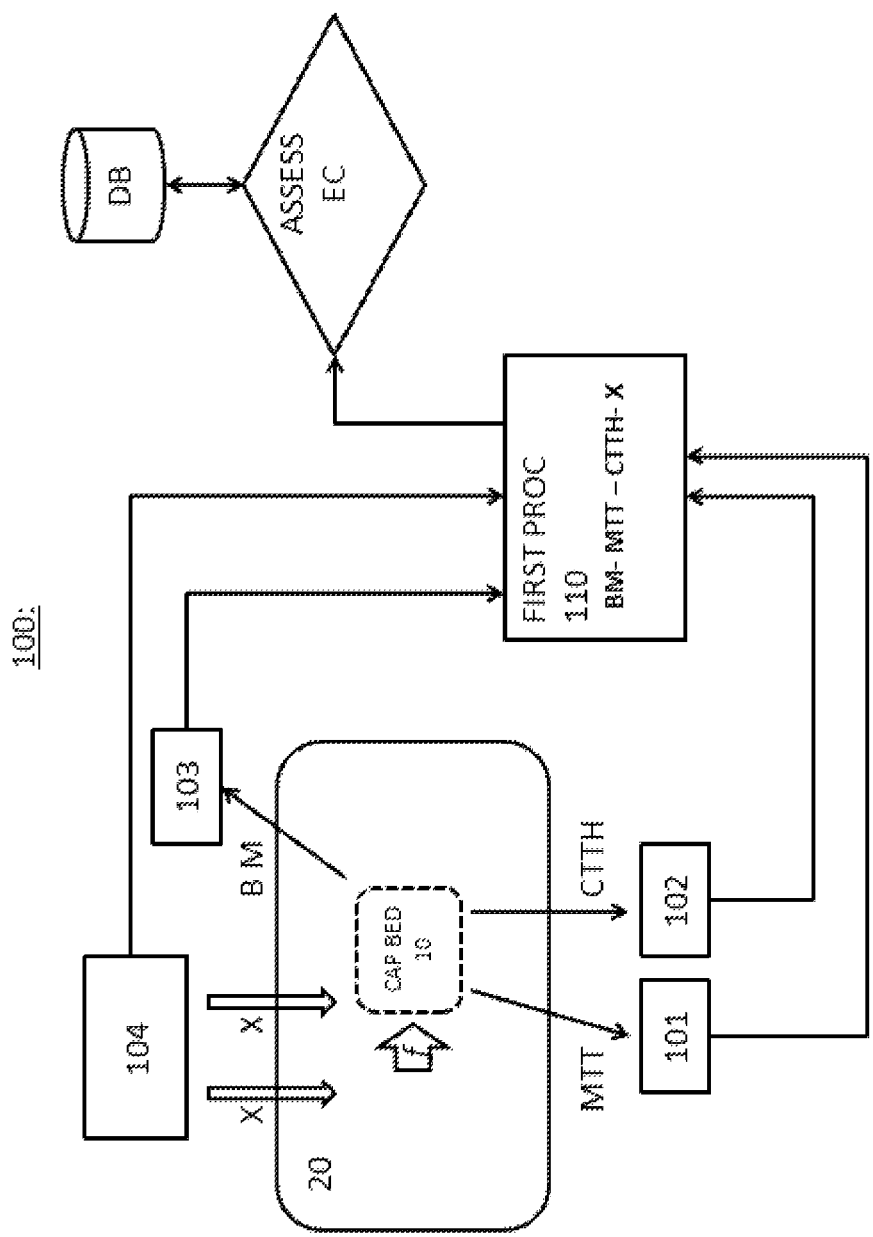
FIG. 11 is another embodiment of a system for measuring a micro-vascular flow distribution of a tissue portion when subjected to the drug or medicine indicated as "X"

FIG. 11 is another embodiment of a system for measuring a micro-vascular flow distribution of a tissue portion (similar to the system shown in FIG. 10) when subjected to the drug or medicine indicated as "X".

In another embodiment of the present invention, the system further comprises:

means for measuring a biomarker (e.g. NO, lactate) level, the biomarker being related to pericyte, basement membrane or endothelial cell conditions in, or near, said capillary bed, the biomarker being related to the first and the second indicator, and a processor (first or second) arranged for assessing said heterogeneity as a function of said biomarker (e.g. NO, lactate) level and an active pharmaceutical ingredient (X) level.

In the present context the term "biomarker" refers to substances or measurable parameters related to pericyte, basement membrane or endothelial cell conditions, such as the flow (velocity and density) of the formed elements of the blood, the diameter of capilliaries and blood vessels in general, the oxygen tension and/or pH in and around the capillary bed, NO (nitrogenmonoxide), and lactate. Furthermore, biomarker refers to conditions that can affect the flow of red blood cells, such as the thickness and composition (e.g. deposits) of the basement membrane, endothelial cell morphology (e.g. thickness and edema), capillary wall stiffness or diameter changes due to external edema.

In yet another embodiment of the present invention, the system further comprises:

means (104) for administering an active pharmaceutical ingredient (X) in, or near, the capillary bed.

The information about the active pharmaceutical ingredient level may be provided to the system, e.g. entered manually into a database being part of the system.

In one embodiment of the present invention, the system further comprises a second processor capable of using the first and the second indicator to estimate an extraction capacity (EC) of a substance (e.g. $O_2$) in said capillary bed.

In yet another embodiment of the present invention, the first and/or second processor is further arranged for comparing said extraction capacity (EC) and/or heterogeneity ($\sigma$) as a function of said biomarker (e.g. NO, Lactate) level and said active pharmaceutical ingredient (X) level.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Capillary Regulation of Oxygen Delivery in the Brain: Functional Recruitment Revisited Functional magnetic resonance imaging (fMRI) and positron emission tomography use cerebral blood flow (CBF), blood volume (CBV) and blood deoxygenation changes as proxies for neuronal activity, and for vasodilatory adaptation to low cerebral perfusion pressure (CPP). Findings of increased oxygen extraction without parallel CBF or CBV changes during functional activation and in patients with cerebrovascular disease therefore challenge operational models of neurovascular coupling and autoregulation.

Here the inventors show that functional recruitment, in guise of capillary flow redistribution, profoundly affects oxygen extraction. In carotid stenosis patients, such redistributions account for ipsilateral oxygen extraction fraction (OEF) increases in the absence of significant CBF or CBV changes.

Capillary flow redistributions reported during functional activation are shown to account for at least 40% of the change in extracted oxygen, likely explaining controversial deoxygenation stages and calibration errors in blood oxygen level dependent fMRI.

Functional recruitment may be as important as CBF to increase oxygen delivery during functional activation, and may provide a metabolic reserve in stages of reduced CPP.

Introduction

Cerebral blood flow (CBF) is regulated to meet the brain's metabolic needs during neuronal activity and changing cerebral perfusion pressure (CPP). The concepts of neurovascular coupling and cerebral autoregulation are cornerstones of brain mapping studies using CBF related changes as proxies for localized neuronal activity, patient management in cerebrovascular disease, and severe cerebral hypo- or hypertension.

The development of positron emission tomography (PET) methods to quantify CBF, cerebral blood volume (CBV) and the cerebral metabolic rate of oxygen consumption ($CMRO_2$) has revolutionized our knowledge of the haemodynamic and metabolic underpinnings of neuronal activity, and more recently, the development of fMRI has allowed the detection of changes in CBF, CBV and blood deoxygenation at high temporal and spatial resolution.

In spite of considerable progress in interpreting functional neuroimaging data in terms of the underlying neural processing, central observations challenge our understanding of the coupling of cerebral hemodynamics to oxidative metabolism: Elusive, short-lasting blood deoxygenation ('the initial dip') and well-established, prolonged post-stimulus deoxygenation ('post-stimulus undershoot') seemingly prove that blood deoxygenation is uncoupled from CBV and CBF during functional activation. Similarly, PET-studies of oxygen extraction fraction (OEF), CBF and CBV in patients with carotid stenosis show that some patients demonstrate normal CBV and CBF, in spite of significantly increased OEF—while patients with increased OEF and CBV are at extreme risk of a subsequent stroke.

Common to these studies—and, we claim, at the root of the controversy—is the fundamental paradigm that the vascular system's only means of adjusting oxygen delivery to meet metabolic needs, is by changing blood volume and blood flow. In cortical capillaries, the velocity and distribution of red blood cell (RBC) is highly variable. Neural activity and decreased perfusion pressure are hence accompanied not only by increased flux of RBCs, but also by rapid redistributions of capillary flows to more homogenous flow patterns. This phenomenon, has been speculated to improve oxygen extraction, a phenomenon called functional recruitment. Recent findings suggest that pericyte constriction of capillary diameter is controlled by local neuronal activity, supporting the notion that capillaries may play a key role in neurovascular coupling.

Here we model the combined effects of capillary flow heterogeneity, CBF and CBV on OEF based on standard, clinical magnetic resonance perfusion data. We show that capillary flow homogenization causes an effective increase in OEF, in addition to the known effects of CBF and CBV. Capillary flow distribution changes reported in the literature account for more than 40% of the increased oxygen delivery during neural activity in rats.

From the premise that states of altered flow heterogeneity are accompanied by OEF changes unaccounted for by parallel CBF and CBV changes, we argue that early and late deoxygenation in fMRI are the results of combined changes in functional recruitment, CBV and CBF in response to local neural activity. We further demonstrate that ipsilateral OEF values in patients with carotid stenosis can be explained by flow heterogeneity changes, serving as a validation of our models, and suggesting that functional recruitment may serve as a hitherto overlooked oxygen reserve.

Patients

Patient 1, a 63 year old male with episodic left-sided hemiparesis caused by occluded right ICA, and patient 2, a 58 year old male with episodes of right-sided blindness due to a 90% stenosis of the right internal carotid, were both examined by PET and PWI. They presented no neurological deficits at the time of examination. Subjects were first [$^{15}$O] PET scanned, followed by Perfusion Weighted Imaging. Blood pressure, pulse and blood oxygen saturation was monitored throughout both scanning sessions. Written informed consent was obtained from both subjects, and the study was approved by the Regional Committee on Research Ethics. PET scans were acquired and analyzed as described by Ashkanian et al. 2009, resulting in parametric maps of CBF, $CMRO_2$ and OEF in 128×128 matrices of 2×2 mm pixels with an isotropic resolution of 7 mm. PET-images were subsequently co-registered to MRI data and resulting PET-OEF resampled to the corresponding PWI-based OEC maps for direct comparison. Data from one additional patient had to be discarded due to severe signal loss caused by susceptibility artifacts, and inability to detect arterial supply vessels in MRI data.

Results are included in the below study.

Capillary Transit Time Heterogeneity and Oxygen Extraction Capacity

The inventors work addresses the fundamental question of how tissue receives sufficient oxygen to meet its metabolic demands. It is currently believed that (except in muscle) this is mainly achieved through local regulation of blood flow. In the current study, the inventors were particularly interested in this relation in brain, where a series of findings reveal fundamental discrepancies between levels of cerebral blood flow (CBF), and the corresponding oxygen metabolism ($CMRO_2$) during brain work. The challenge was therefore to find an alternative to the 130 year old paradigm of a neurovascular coupling, in which arteriolar diameter is adjusted to adapt CBF according to metabolic needs.

The inventors analyzed the role of capillary flow distributions in terms of supporting tissue oxygenation. The idea dates back to August Krogh, who in 1920 demonstrated the capillary motor regulating mechanism: Capillary pericytes may open capillaries, thereby redistributing flow (so-called recruitment), such that the extraction of oxygen is increased. The phenomenon was later abandoned in brain (and all tissues except muscle), as closed capillaries are generally not observed—yet the role of rapid changes in capillary flow patterns observed in response to local cellular activity, remains unknown.

The inventors successfully solved the complex set of equations that govern the biophysics of oxygen transport in tissue, and can now explain the profound implications of this phenomenon in detail. In particular, they are able to show how oxygen delivery to tissue depends not only on tissue blood flow—which is perhaps the most commonly assumed paradigm in the study and management of disease—but also on capillary transit time patterns.

Rather than performing detailed studies of capillary flow patterns themselves, they have performed an exhaustive analysis of no less than seven studies of transit time dynamics in brain to show that this novel biophysical mechanism is a fundamental property of the parallel organization of capillaries in biological tissue. Data consistently demonstrate that capillaries account for at least one third (and probably most) of the oxygen supply needed during physiological challenges to brain tissue, and prove that this mechanism is indeed necessary to fuel for example neural activity and resting energy needs during hypoxia.

In a direct comparison between gold-standard PET oxygen metabolism measurements and MRIbased model parameter estimation, they demonstrate first evidence that this new model may explain findings of high oxygen extraction fraction in patients with symptomatic carotid occlusion, but no apparent changes in CBF or CBV; a common finding that has mystified clinician and scientists for decades due to unexplained flow-metabolism uncoupling.

This novel insight provides the missing link, by revealing a neurocapillary coupling, as pericyte dilation and reduction of capillary transit time heterogeneity profoundly increases oxygen extraction capacity, independent of upstream arteriolar tone and CBF.

The model thereby adds important new insights into other unsolved problems within neuroscience. From the current controversies over the BOLD effect in MRI neuroimaging to the significance of capillary microangiopathy and pericyte loss observed in conditions such as ageing, hypertension, diabetes, Alzheimer's Disease and Parkinson's Disease. Bell and colleagues (Neuron, Nov. 4, 2010) recently reported that age-dependent vascular damage in pericyte-deficient mice precedes neuronal degenerative changes, learning and memory impairment, and the neuroinflammatory response. This study suggest that the parallel disturbance of capillary flows—and thereby the ability engage this 'capillary oxygen reserve' during any sort of functional or physiological challenge—may play an independent role in the pathogenesis of these conditions.

The physiological principle proven here applies to all tissue types, and is therefore of general interest, due to the fact that prior art have essentially 'overlooked' the large portion of oxygen delivery that depend on capillary function, as opposed to regulation of arterial and arteriolar diameter. In particular, microangiopathy and loss of pericytes is a general feature in ageing, hypertension and in diabetic complication. These findings may help understand how tissue hypoxia develops in these conditions, in spite of normal tissue perfusion. Of note, pericytes react to for example by-products of physical exercise and common anti-hypertensives. Hence, these findings may point not only to new disease mechanisms for chronic diseases, but new avenues in preventing and treating them, by specifically targeting pericyte function and survival.

The model also shows a disturbing property of capillary oxygen delivery. Slight disturbances in the heterogeneity of capillary flows, which have been established in for example ischemia and critical illness, cause paradox physiological state of malignant capillary transit time heterogeneity, in which attempts to increase blood flow leads to global hypoxia as well as local hyper-oxygenation.

This may alter our understanding of common states such as tissue hypoxia in critical illness and reperfusion injury.

Conclusion

Normal brain function depends on sufficient oxygen delivery to support neuronal activity. Neurovascular coupling, a range of mechanisms that converge on arterioles to adjust cerebral blood flow, represents the prior art framework for understanding how brain work is fueled. Currently, the capillary bed is not believed to actively regulate tissue oxygenation, yet the role of rapid homogenization of capillary flows, consistently observed in states of increased oxygen demand, remains elusive.

Here the inventors model the combined effects of vasodilation and capillary transit time heterogeneity (CTTH) on oxygen transport. It is shown that biophysically, reported CTTH changes during neuronal activity, hypoxia, mild hypercapnia and mild cerebral hypotension maintain appropriate oxygenation during such challenges, accounting for up to 50% of the change in oxygen delivery.

The inventors propose the existence of a neurocapillary coupling and speculate that capillary pericytes affect tissue oxygenation during increased oxygen needs by this mechanism, irrespective of their effect on arteriolar tone.

Results

FIG. 4 shows arteriolar, capillary and venular oxygenations in the case of 'actual' transit time distribution measured in the resting rat brain (FIG. 4.a.) by Stefanovic and colleagues (Stefanovic et al., 2008), and in the case of homogenous capillary transit times (FIG. 4.b.), which corresponds to our current notion of purely 'arteriolar' regulation of oxygen delivery, and for an. In this figure, we assumed negligible extracapillary oxygen concentration, and that oxygen in individual capillaries was extracted according to commonly accepted Crone-Renkin kinetics (Crone, 1963), and immediately metabolized. We set the model parameter $k=118$ $s^{-1}$ to yield a resting state oxygen extraction of 0.3 in this dataset and used this value throughout the paper. Note that, despite identical flow and number of perfused capillaries (no recruitment), resting state capillary transit time heterogeneity (CTTH) reduces the amount of oxygen that can be extracted (as evidenced by the higher venular oxygenation). The assumption that capillary oxygen extraction capacity depends on blood flow, and only on the capillary distribution of blood in cases of capillary recruitment, is clearly incorrect. FIG. 6.a. shows the combined contour and intensity plot of the oxygen extraction capacity (OEC—the maximal fraction of oxygen that can biophysically be extracted from blood), as a function of the mean transit time (MTT or sometimes abbreviated $\mu$) and transit time heterogeneity $\sigma$. Note that OEC is conveniently described by a term controlled by arteries and arterioles (on the x-axis), namely the mean transit time $\mu$, which by the Central Volume Theorem (Stewart, 1894) equals the CBV: CBF ratio, and a term describing the heterogeneity of the resulting RBC transit times (on the y-axis), namely the standard deviation of capillary RBC transit times, $\sigma$. Reported values of $\mu$ and $\sigma$, and their changes during various physiological or pathological changes, can therefore be translated into biophysical oxygen transport capacities, as well as the relative arteriolar and capillary contributions to these values or changes, by using FIG. 6.

Note that changes in capillary transit times provide a biophysical mechanism whereby oxygen extraction capacity may vary greatly for a given mean transit time (i.e. fixed blood volume and flow), even without capillary recruitment. For a fixed mean transit time, the most efficient oxygen extraction hence occurs for an infinitely narrow transit time distribution ($\sigma=0$).

The total metabolic rate of oxygen, that may be supported, $CMRO_2^t$, further depends on cerebral blood flow, as $CMRO_2^t=CBF \cdot C_A \cdot OEC$, where $C_A$ is the arterial concentration of oxygen. Again, we utilized the central volume theorem, $\mu=CBV/CBF$ (Stewart, 1894), where CBV in our case refers only to the fractional volume of blood vessels from which oxygen can diffuse across vessel walls. FIG. 6 depicts the dependence of $CMRO_2^t$ on transit time in two cases: In FIG. 6.b. oxygen extraction is assumed to occur in capillaries only. As capillaries allow only passage of single files of RBCs, the capillary blood volume is fixed from the perspective of oxygen transporting blood. In FIG. 6.c., oxygen diffusion is allowed to occur in larger vessels such as arterioles (Pittman, 2011), which may dilate in parallel with flow and therefore cause a smaller increase in $\mu$ for a given CBF increase. We chose a very conservative, empirical CBF-CBV relation based on total blood volume changes observed by PET in brain, proposed by Grubb and colleagues (Grubb et al., 1974). Note that the most efficient oxygen extraction again occurs for a homogeneous transit time distribution ($\sigma=0$).

A surprising phenomenon is noted in FIG. 6.b. The effects of vasodilation (reduction of transit time) on the amount of oxygen that can be off-loaded to tissue, differ according to the two phases separated by the yellow line in FIG. 6.b.: In the 'high CTTH' phase to the left of the line, net oxygen delivery decreases as mean transit times become faster, creating a paradox state in which vasodilation leads to increasing oxygen starvation of tissue. We will refer to this phenomenon (CTTH above the indicated line for a given $\mu$) as malignant CTTH in the following.

Interestingly, the mode (Equation (5), Experimental Procedures) predicts that for mean transit times beyond 6 seconds, OEC becomes 99% of its maximal value (using $k=118$ $s^{-1}$). Therefore, as transit times exceed about 6 s in the rat, oxygen extraction cannot be increased further. This inherent biophysical threshold (and its analogue value in humans) is of particular interest to studies of diseases where CBF is limited, such as acute stroke and severe carotid stenosis: Here, MTT is routinely measured by neuroimaging based perfusion techniques during routine clinical examinations, and may hence detect critical levels of hypoperfusion. FIGS. 6.c. and 6.d. shows the predicted relation between CBF, and OEC (decreasing curves) and $CMRO_2^t$ (increasing curves), respectively. Curves were determined for measured CTTH and transit time values during rest and functional activation in the brain (Stefanovic et al., 2008), and compared to current models of oxygen transport (Buxton and Frank, 1997; Vafaee and Gjedde, 2000), which assume uniform capillary transit time (our model for $\sigma=0$). Both figures assumed a uniform extracapillary oxygen tension of 25 mmHg, representing an upper limit of measured values in brain (Ndubuizu and LaManna, 2007). Note that high tissue oxygen tension decreases the maximum attainable OEF as blood-tissue equilibrium is reached, and OEC values in FIGS. 6.c. and 6.d. therefore reach only 50%.

FIG. 4.c. displays the relation assuming Grubbs relation, in which relatively large CBF increases only result in small mean transit time changes, due to the parallel vasodilation. Therefore, although CTTH reduction accounted for over 50% of the additional oxygen delivery, this assumption probably underestimates the importance of CTTH reduction on oxygen transport. Note that the combined effect of an CBF increase and CTTH reduction produce an almost linear increase in extracted oxygen with flow, unlike the more disproportionate increase in CBF needed to explain a given increase in oxygen utilization in previous models (Buxton and Frank, 1997; Fox and Raichle, 1986; Hyder et al., 1998; Vafaee and Gjedde, 2000). FIG. 4.*d*. shows the same relation assuming fixed blood volume: Note that vasodilation alone in this—probably more realistic—case would not alter oxygen delivery. Rather, the parallel reduction in CTTH was necessary to increase oxygenation to fuel brain work. This phenomenon owes to the fact that resting transit time characteristics in this case were such that an isolated transit time reduction would correspond to crossing the line that defines the area of malignant CTTH in FIG. 6.*b*. (See also the table in FIG. 3 and corresponding symbol in FIG. 6.*b*.)

Figure 5:
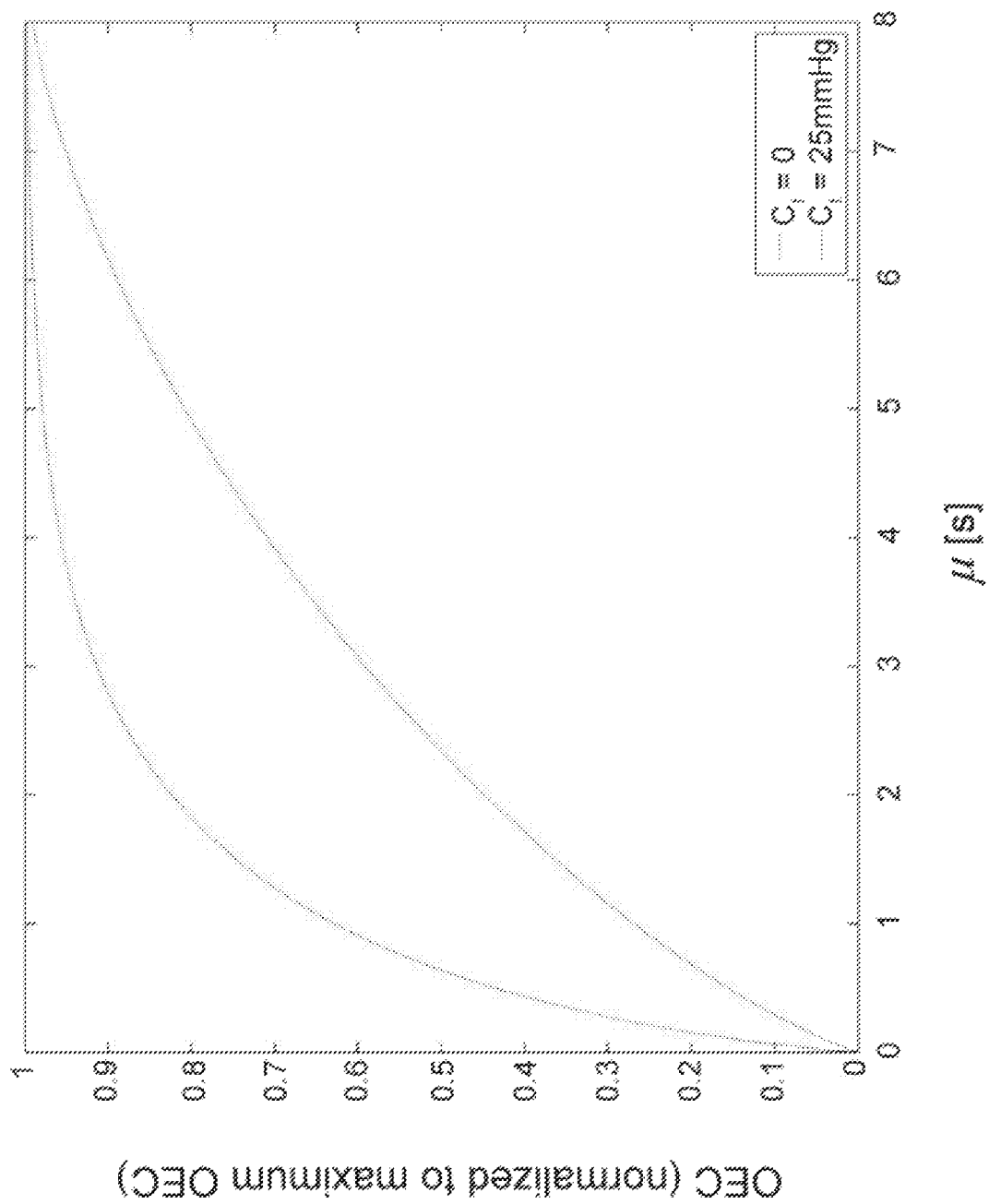
FIG. 5 shows the effects of tissue oxygen tension on the MTT-OEC relation.

FIG. 5 shows the relation between OEC and blood flow transit time for negligible and high tissue oxygen tensions. The main effect of a finite tissue oxygen tension is to reduce the maximum attainable OEC, while increasing the slope of the $CMRO_2$-CBF relation (Reducing the blood-tissue oxygen concentration gradient gradually eliminates the contribution of fast-flowing RBCs, who display poor extraction efficiency, to the slope of the curve). This property hence enhances the oxygen release by a sudden increase in blood flow and/or CTTH reduction due to physiological stimuli such as those studied below, or vasomotion.

Figure 3:
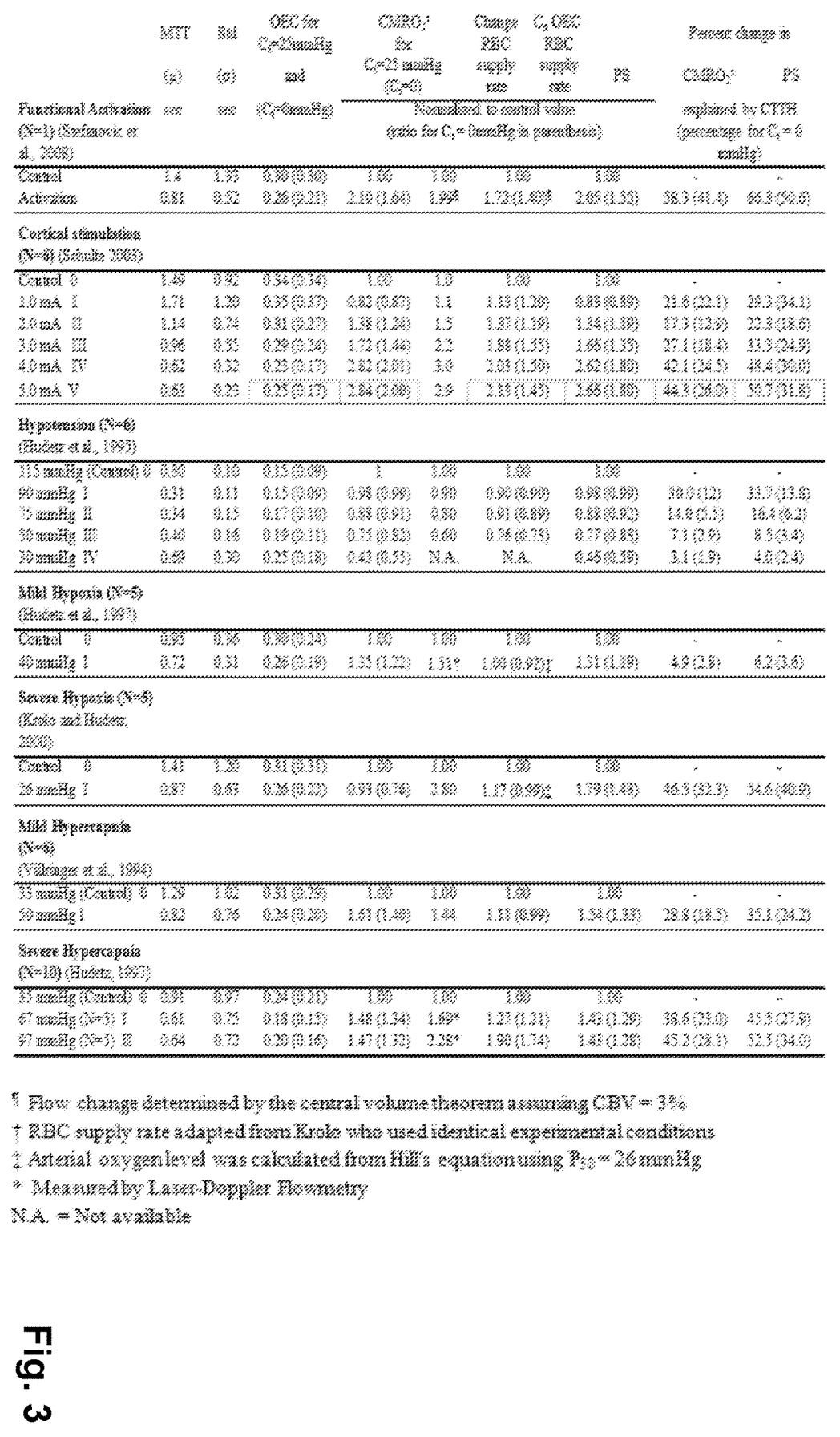

The table in FIG. 3 shows data from all available in vivo recordings, in which transit time characteristics were reported in such a manner that our model could be applied with limited assumptions. These were all performed in rat brain. Note that CTTH is large ($\sigma$ relative to $\gamma$) in the control states of all studies, emphasizing the importance of incorporating CTTH in models of oxygen transport. The $\mu$ and $\alpha$ values determined in the various physiological states are illustrated in the OEC and $CMRO_2^t$ contour plots in FIG. 6.

Qualitative observations of RBC or plasma flows during functional activation, consistently report CTTH reductions during functional hyperemia (Akgoren and Lauritzen, 1999; Vogel and Kuschinsky, 1996), with capillaries showing low velocities during rest displaying the largest velocity increases during activation (Stefanovic et al., 2008). Analysis of transit time recordings obtained by simultaneous tracking of intravascular contrast across several capillaries in a rat show that the resulting homogenization caused a smaller reduction in OEC than would result from a homogenous transit time distribution (FIG. 4 and FIG. 6.*a*.). The predicted $CMRO_2^t$ were within 20% of those inferred from independent flow change estimates, and within measured values of oxygen metabolism and oxidative glucose utilization in α-chloralose anesthetized rats during forepaw stimulation by localized spectroscopy (Hyder et al., 1996). Note that biophysically, CTTH reductions accounted for more than 32% of the increased oxygen delivery during functional activation by the most conservative assumptions (negligible extracapillary oxygen tension, and Grubbs relation). If we assume non-negligible tissue oxygen tension and (more realistically) constant volume of oxygen exchanging vessels, half if not all (FIG. 4.*d*.) of the additional oxygenation for functional activation depended on CTTH reductions. In direct cortical electrical stimulation (Schulte et al., 2003), data showed (except for one data point), gradual reduction of CTTH and OEC with increase in current strength, resulting in increasing maximum oxygen utilization rates. This concurs with expected metabolic needs, as increased electrode current (as opposed to frequency) is believed to elicit firing of an increasing number of neurons in the rat cortex. We note that the CTTH reduction accounted for an increasing proportion of the increase oxygen availability, and hence appears necessary to support increased tissue oxygen needs.

In hemorrhagic hypotension, data by Hudetz and colleagues (Hudetz et al., 1995) shows that maintenance of 'normal' CTTH seemingly plays a marked role in maintaining oxygen delivery as perfusion pressure drops (FIG. 3). Note that CTTH increased with gradual loss of perfusion pressure (autoregulation in terms of RBC flux was lost at a cerebral perfusion pressure dropped below 75 mmHg), rapidly diminishing the capillary contribution to total oxygen delivery in this animal model. FIG. 3 shows the dynamics of transit time and CTTH changes during the reported physiological stimuli in the OEC and contour plots. Note that in ischemia (reduced CBF), the model predicts metabolic benefits of maintaining low flow heterogeneity and the lowest possible mean transit time (i.e. blood volume), given the available blood flow.

In hypoxia, transit time homogenization was observed in proportion to arterial oxygen tension, resulting in high OEC despite dramatic increases in CBF. Our model hence predict that oxygen availability was preserved during severe hypoxia, which could be equally attributed to CTTH reduction and vasodilation (FIG. 3). In this case, CTTH reductions were clearly necessary to maintain resting metabolism. In this extreme case, the Grubb-relation underestimated the CBF increase and hence the predicted $CMRO_2^t$.

In hypercapnia the combined studies by Villringer and colleagues (Villringer et al., 1994) and Hudetz and colleagues (Hudetz et al., 1997) showed reduction of CTTH in proportion to the increase in $PaCO_2$, in agreement with a qualitative study by Abounader and colleagues in conscious rats (Abounader et al., 1995).

Interestingly, using measured increases in CBF, the model predicted largely unaltered oxygenation, despite a large increase of flow during a 5% $CO_2$ inhalation paradigm (Villringer et al., 1994). For higher $P_aCO_2$ levels (Hudetz et al., 1997), oxygen delivery clearly exceeded expected metabolic needs. We note that the hemodynamic changes resembled those of somatosensory and cortical stimulation, as commonly assumed in studies of the neurovascular coupling. To examine whether the changes in CTTH may explain observations of increased OEF in the absence of changes in CBF and CBV in symptomatic carotid stenosis (Derdeyn et al., 2002), we further analyzed two patients from a previous PET study (Ashkanian et al., 2009), for whom perfusion weighted imaging, and hence OEC model parameter estimates, were also available. In FIG. 7, gold-standard PET OEF map (7.*a*.) of a patient with unilateral carotid stenosis is compared with the corresponding, co-registered MRI maps of OEC (7.*b*.), MTT (7.*c*.) and CBV (7.*d*.). Note the corresponding areas of high OEF and OEC (encircled), which in turn did not display noticeable changes in regional CBV or MTT. FIGS. 7.*e*. and 7.*f*. show values of OEC and MTT, averaged over the affected and unaffected hemispheres, for each image slice in both patients. While there is significant correlation between MR estimates of OEC and PET OEF ($\rho=0.65$, $p<10^{-5}$), only modest correlation was found between MTT values and PET ($\rho=0.23$, $p=0.13$), confirming the notion that MTT and CTTH changes together explain increased OEF in symptomatic carotid stenosis. To compare the relative roles of CTTH and vasodilation as means of maintaining tissue oxygenation in these patients, we compared the change in a values in areas of increased CBV to those in areas of decreased CBV (both relative to the average contralateral values). The results in FIG. 7.g. indicate that brain tissue seemingly exploits CBV and CTTH changes in a complementary fashion to optimize oxygen extraction.

Overall, FIG. 3 and FIG. 6 show that (with the exception of severe hypotension), CTTH reductions counteracted the OEC-lowering effects of CBF increases across varying degrees of vasodilation. Importantly, even with the most conservative estimates of the effects of CTTH (Grubb's relation and negligible tissue oxygen tension) compared to those of vasodilation (transit time reductions) on total oxygen delivery, reduction of CTTH was necessary to maintain appropriate oxygenation, both for resting state metabolism during hypoxia, and to fuel cortical activity during somatosensory or cortical electrical activation.

Discussion

The model developed here extends existing models of oxygen extraction in tissue by including the effects of CTTH, based on capillary transit time properties available from in vivo microscopy studies. Using accepted diffusion properties of single capillaries, our model demonstrate that it is a basic property of the parallel organization of capillaries that oxygen extraction capacity depends not only on arterial and arteriolar tone as hitherto believed (as quantified by the mean transit time, the x-axis in FIG. 6), but also to a large extent on the distribution of capillary transit times (as quantified by the standard deviation of capillary transit times, the y-axis in FIG. 6).

The model thereby extends the original notion of capillary recruitment (Krogh, 1919) by showing that is represent merely an extreme case of capillary transit time heterogeneity, while changes in CTTH alone (with all capillaries open) may alter the effective capillary surface area available for diffusion several-fold (FIG. 6.d.)

Direct observations of the capillary bed in rat brain during rest consistently show RBC transit times to be extremely heterogeneous, constantly varying along and among capillary paths (Kleinfeld et al., 1998) with transit time standard deviations ranging from 30 to 100% of the mean transit time (See FIG. 3). Based on these in vivo results, our analysis results clearly demonstrate that it is crucial to include the effects of CTTH in studies of the coupling between cerebral oxygen metabolism and local hemodynamics. Model analysis of these data hence confirms the hypothesized effects of CTTH on the diffusion properties of oxygen in brain (Kuschinsky and Paulson, 1992).

Figure 8:
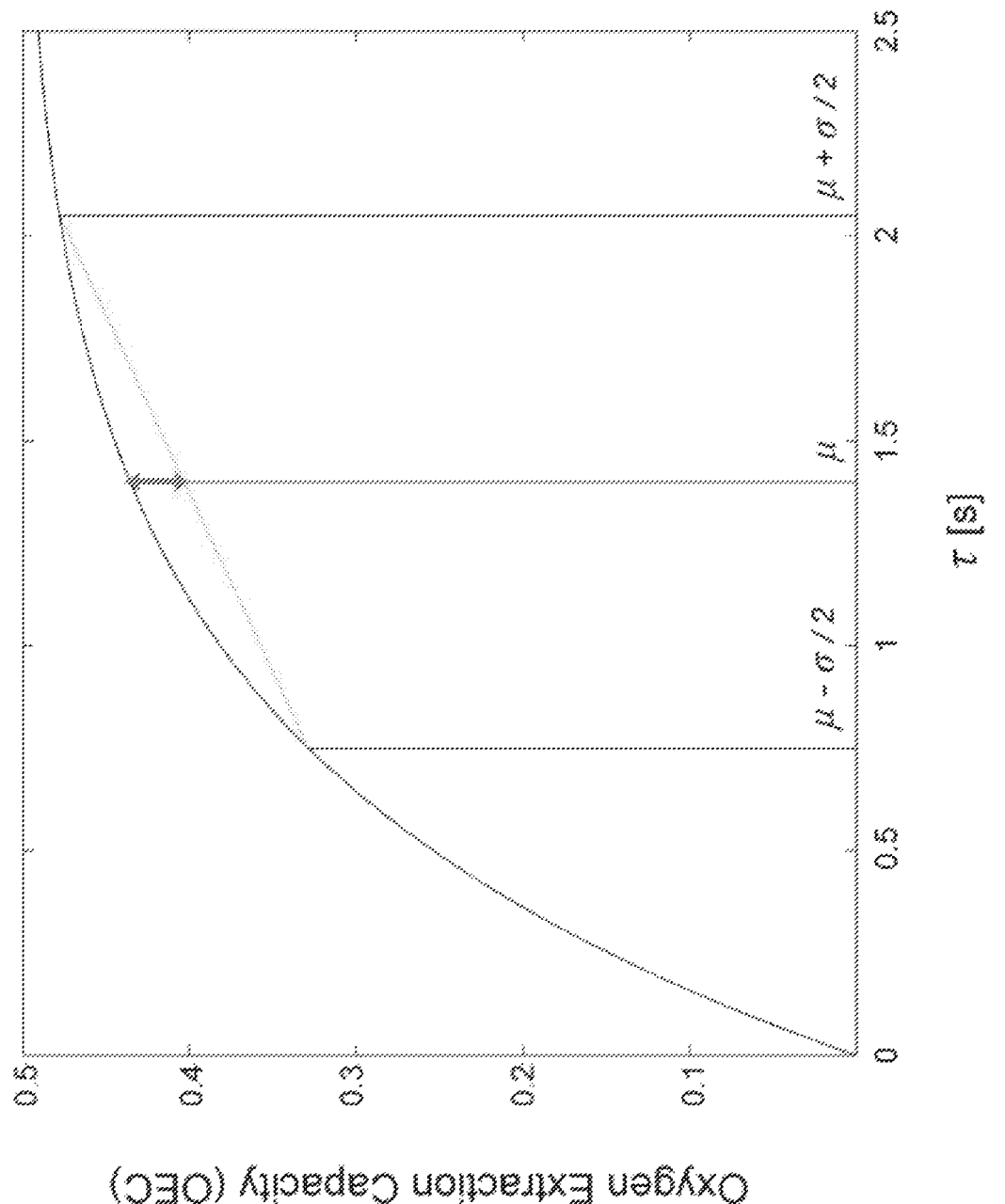
FIG. 8 shows oxygen extraction capacity as a function of capillary transit time.

Perhaps the most crucial finding is that—even by the most conservative estimates of the relative contributions of vasodilation and CTTH reduction to tissue oxygenation—adaption of capillary transit time heterogeneity is crucial to maintain sufficient oxygenation during physiological challenges such as hypoxia and 'normal' cortical activation. Our analysis shows that CTTH reductions effectively reduces the drop in oxygen extraction fraction (FIG. 6.a.) that would otherwise result from vasodilation (FIG. 8). Several researchers have noted that the OEC decrease (FIG. 8) that invariably accompanies with functional hyperemia implies that a disproportionate increase in CBF is required to support even modest increases in the metabolic rate of oxygen (Buxton and Frank, 1997; Fox and Raichle, 1986; Hyder et al., 1998; Vafaee and Gjedde, 2000). Our study shows however, that biophysically, the combined effects of CBF increase and CTTH reduction reduces OEC less, leading to almost proportional increases in flow and oxygen delivery, thereby greatly increasing oxygen extraction relative to an 'isolated' CBF change (FIGS. 4.c and 4.d.).

The separate effects of blood flow and CTTH on oxygen transport predicts a clear distinction between tissue ischemia and tissue hypoxia. In states of decreased cerebral perfusion pressure, parallel increases in $\mu$ and $\alpha$ was observed by Hudetz and colleagues (Hudetz et al., 1995). Similar findings of increased capillary flow heterogeneity by Tomita and colleagues in a model of ischemic stroke (Tomita et al., 2002), suggest that CTTH increase is a crucial phenomenon which reduces oxygenation in ischemia, in a manner that cannot be detected by CBF changes alone.

The patient examples (FIG. 7) provides first evidence that changes in CTTH may be involved in maintaining tissue oxygenation (by increasing OEF) in carotid stenosis. Our model predicts that maintenance of low CBV (and hence low $\mu$ for a given CBF) and low CTTH represent the most favorable hemodynamic state in a states of limited blood supply (reduced CPP). We speculate that the favorable outcome for patients with carotid stenosis displaying high OEF/normal CBV, observed by Derdeyn and colleagues (Derdeyn et al., 2002), owes to maintenance of such low CBV, and preserved capability to increase oxygenation by reducing CTTH.

The malignant CTTH phenomenon implies that any capillary hindrance to the passage of RBCs may have profound effects on oxygen extraction capacity, even in cases where CBF is normal. Abnormally high CTTH has been observed in cerebral ischemia (Tomita et al., 2002), and was recently attributed to abnormal constriction of capillary pericytes, persisting after tissue reperfusion (Yemisci et al., 2009). While the parallel a increase aggravates hypoxia for a given level of ischemia according to our model, tissue reperfusion may have paradox consequences if CTTH is not immediately normalizes, as suggested by the findings of Yemisci and colleagues (Yemisci et al., 2009). As CBF is normalized and p therefore becomes lower, persisting, high a values will tend to result in malignant CTTH (FIG. 6.b.). We note that the ensuing hypoxia/acidosis is likely to elicit upstream vasodilation, further decreasing oxygen delivery, resembling the physiological characteristics of the luxury perfusion syndrome (Lassen, 1966) which is observed across many tissue types upon reperfusion. Means of ensuring capillary patency and function hence seems of the utmost importance to maintain oxygenation in ischemia and reperfusion.

The extent to which CTTH reduction is an actively regulated mechanism, or a passive effect of the increased RBC flux in states of high CBF, remains poorly understood. The studies analyzed here generally showed decreasing CTTH as a function of flow. The notion of a passive process, however, is contradicted by findings of reduced CTTH in hypocapnic rats (Vogel et al., 1996), where CBF is significantly reduced, and in some cases of acute human stroke (Østergaard et al., 2000).

The capillary bed has attracted considerable interest in the search of mechanisms that couple neuro-glial activity to the local regulation of cerebral blood flow (Attwell et al., 2010). Capillary pericytes are contractile cells, found on the abluminal side of endothelial cells, and increasing in vitro evidence suggest that they contract and dilate in response to local blood pressure and cellular activity (Diaz-Flores et al., 2009). Peppiatt and colleagues demonstrated that a large proportion of cerebellar pericytes dilate in response to local electrical stimulation and GABAergic and glutamatergic signaling, suggesting a link between local inhibitory/excitatory signaling and local hemodynamics, possibly by eliciting upstream vasodilation (Attwell et al., 2010; Peppiatt et al., 2006). In a recent paper, however, Fernandez-Klett and colleagues (Fernandez-Klett et al., 2010) demonstrated that pericytes control capillary diameter in vivo, while arterioles were shown to elicit hyperemia in their experimental setting (Fernandez-Klett et al., 2010). We propose that such pericyte action is key to the neurocapillary coupling mechanism described above, as generalized pericyte dilation permits more homogenous flow of RBC in response to local release of neurotransmitters (Peppiatt et al., 2006)—and hence higher OEC, irrespective of parallel flow increase. Of note, pericyte constriction is believed to affect the passage of RBC only. Indeed, Vogel and colleagues, showed that the extent of CTTH depends on the presence of RBCs, supporting the role of pericytes in regulating CTTH (Vogel et al., 1997). This mechanism is further supported by the slight increase and homogenization of capillary CBV values observed during functional activation (Stefanovic et al., 2008), while explaining the profound effects of this seemingly insignificant blood volume change on oxygen delivery (Attwell et al., 2010).

Our findings may advance the understanding of the blood oxygenation changes observed during brain activity: If vasodilation (which generally increases blood oxygenation) and CTTH reduction (which increases OEC and hence decreases blood oxygenation) are controlled by independent mechanisms as suggested by the findings above, our findings suggest a straightforward interpretation of the BOLD signal as a superposition of a positive (arteriolar) and a negative (capillary) components.

In summary, the ability of the capillary bed to reduce CTTH seem crucial in order to maintain oxygenation during physiological challenges (neuronal activation, episodes of hypoxia or reduced perfusion pressure), while abnormally high CTTH may even cause reduced, overall oxygen extraction during rest, in spite of normal CBF (Malignant CTTH). In view of this, changes in capillary morphology and patency, such as the microangiopathies observed in hypertension, diabetes and neurodegenerative diseases, may interfere with capillary flow and have profound metabolic implications in their own right. Interestingly, changes in pericyte morphology are early hallmark of disease progression in these diseases (Diaz-Flores et al., 2009; Hamilton et al., 2010): The potential importance of pericytes and capillary morphology in neurodegenerative diseases was recently underscored by findings of Bell and colleagues, who found that age-dependent vascular damage in pericyte-deficient mice precedes neuronal degenerative changes, learning and memory impairment, and neuroinflammatory response (Bell et al., 2010).

Limitations to the Study

The application of the model is currently limited to data obtained by direct observations of RBC passage in superficial capillaries in animals. While technical advances may extend such microscopic techniques to deeper structures (Barretto et al., 2011) in rodent brain, we are currently extending neuroimaging based measurements of capillary blood retention in humans to assess CTTH noninvasively in humans (Østergaard et al., 1999), as reported above.

In terms of model limitations, we have assumed a constant value of the oxygen tension in tissue immediately outside the capillaries, in line with the recently suggested 'revised oxygen limitation hypothesis', according to which blood supply is regulated so as to maintain a constant, non-vanishing oxygen tension (Buxton, 2010). It has, however, been pointed out that tissue oxygen tension is likely to be heterogeneous, possibly fluctuating in time (Ndubuizu and LaManna, 2007). Our assumption of a tissue oxygen tension that remains constant in space and time may therefore be a simplification. We believe that our current model captures the qualitative implications of capillary flow heterogeneity, but future studies should analyze the influence of a biologically more realistic distribution of tissue oxygenation. In particular, the effects of non-negligible oxygen tension suggest that oxygen tension gradients in tissue represents an additional dynamic parameter that affects the brain's ability to regulate oxygen supply over short time scales. We assumed a gamma variate distribution of transit times through the capillary bed. While this assumption is accepted in the modelling of capillary transit time dynamics, it is convenient for the analytical mathematical approach chosen here. Other distributions would require more complex analysis, but not change the overall conclusions of our study. We assumed a homogeneous population of morphologically identical cylindrical capillaries, and that oxygen kinetics may be described in terms of two compartments with a single rate constant related to the capillary walls permeability to oxygen. If oxygen is well stirred in the capillary, the description in terms of a single characteristic timescale is accurate. Considering additional factors that affect oxygen binding to hemoglobin, such as pH, could improve our model, but would not change the overall conclusions of the study. In biological tissue, capillaries display a distribution of lengths, and are interconnected, such that the model in FIGS. 4.$a$. and 4.$b$. is somewhat oversimplified. Capillary transit time distributions therefore reflect the underlying distribution of capillary lengths, as well as the velocity distribution of RBCs. Also, capillary branching, with interconnections to other capillaries, tends to equilibrate oxygen tensions across some parallel capillary paths. These aspects mostly affect the estimation of absolute transit time heterogeneities from literature data that report these in terms of blood flow, RBC velocities, or cell fluxes, and do not reduce the quantitative effects of CTTH changes reported here.

Experimental Procedures

Modelling oxygen extraction capacity based on capillary transit time characteristics Our approach to model the effects of transit time heterogeneity on oxygen extraction capacity lends from previous models of MR based residue detection data (Mouridsen et al., 2006b), characterizing flow heterogeneity by the probability density function of microvascular transit times $h(\tau)$, parameterized as a gamma variate with parameters $\alpha$ and $\beta$.

$$h(\tau) = \frac{1}{\beta^{\alpha}\Gamma(\alpha)}\tau^{\alpha-1}e^{-\tau/\beta}, \quad (1)$$

The vascular mean transit time $\mu$ is then determined as $\alpha\beta$, and its standard deviation $\sigma=\sqrt{\alpha}\beta$ quantifies the heterogeneity of the flow. In the literature, perfusion heterogeneity of capillary flows is often reported in terms of the coefficient of variation, CV, defined as the standard deviation normalized by the mean. The relative heterogeneity, here defined as the transit time coefficient of variation is then $1/\sqrt{\alpha}$.

To incorporate the effect of flow heterogeneity on the upper biophysical limit for the proportion of oxygen that may be extracted by tissue, oxygen extraction capacity (OEC), and hence the upper limit on the cerebral metabolic rate of oxygen that can supported, $CMRO_2^t$, we first model the dependence of oxygen extraction $Q(\tau)$ on transit time $\tau$, and then compute $CMRO_2^{max}$ by integrating over the distribution $h(\tau)$ of transit times.

In mathematical terms, $CMRO_2=CBF \cdot C_A \cdot OEF$, where $C_A$ is arterial oxygen concentration, and $$OEF = \int_0^\infty d\tau h(\tau) Q(\tau). \quad (2)$$

In modelling $Q(\tau)$, we consider first a single capillary of length L and volume V, assuming that oxygen inside the capillary is well stirred along the radial direction, and that the current of oxygen across the capillary wall is proportional to the difference between plasma oxygen concentration ($C_p$) and tissue oxygen concentration ($C_t$). The differential equation for total oxygen concentration C as a function of the fractional distance $x \in [0,1]$ along a capillary with flow f and volume V then reads $$\frac{dC}{dx} = -\frac{kV}{f}(C_p - C_t) \quad (3)$$

assuming equal forward and reverse rate constants k for simplicity. Note that the capillary transit time $\tau$ is identical to V/f. The cooperativity of oxygen binding to hemoglobin is approximated by the phenomenological Hill equation:

$$C_B = B \frac{P^h}{P_{50}^h + P^h} \quad (4)$$

where $C_B$ is the concentration of bound oxygen, B is the maximum amount of oxygen bound to hemoglobin, P is oxygen partial pressure in plasma, $P_{50}$ is the oxygen pressure required for half saturation and h is the Hill coefficient. Neglecting the contribution of plasma oxygen to the total oxygen content ($C_B \approx C$), we use Eq. (4) to express the oxygen pressure in terms of total oxygen content ending up with a general equation for oxygen concentration as a function of the normalized distance x along a capillary with transit time $\tau$ (Hayashi et al., 2003; Mintun et al., 2001):

$$\frac{dC}{dx} = -k\tau \left( \alpha_H P_{50} \left( \frac{C}{B-C} \right)^{1/h} - C_t \right) \quad (5)$$

where $\alpha_H$ is Henry's constant. The model constants were assigned generally accepted literature values: h=2.8, B=0.1943 mL/mL, $C_A$=0.95·B, $\alpha_H$=3.1×10$^{-5}$ mmHg$^{-1}$ and $P_{50}$=26 mmHg. Oxygen concentration immediately outside the capillaries is unknown, here we used a value corresponding to P=25 mmHg (Ndubuizu and LaManna, 2007). This equation can be solved for x as a function of C, when tissue oxygen concentration is 0:

$$\alpha_H P_{50} k\tau x + C(x)^{1-1/h} B^{1/h} {}_2F_1\left(1-1/h, -1/h, 2-1/h; \frac{C(x)}{B}\right) \Big/ (1-1/h) = \text{constant.} \quad (6)$$

The constant on the right-hand side is determined by the initial value, $C(0) = C_A$ and $_2F_1$ is a hypergeometric function (Arfken and Weber, 2005). If oxygen binding corporativity is ignored so that $C_p \propto C_T$, capillary oxygen concentration will be given by the familiar exponential expression $C(x) = C(0)\exp(-k\tau x)$. Under the assumption of a constant tissue oxygen tension $C_t$ (Buxton, 2010), we numerically solve the differential equation in (8) to yield the single capillary extraction fraction $Q=1-C(1)/C(0)$ as a function of $k\tau$. We find that as the mean transit time increases, the oxygen extraction fraction approaches its maximal value of $Q_{max} \approx 0.5$. In order to calculate oxygen extraction capacity as the average over a given transit time distribution as expressed in Eq. (2), we approximate the capillary oxygen extraction fraction by a N'th order polynomial in $k\tau$, combined with the exponential decay expected in the absence of oxygen binding cooperativity:

$$Q(k\tau) = Q_{max}\left(1 - e^{-k r\tau}\sum_{n=0}^{N} q_n(k\tau)^n\right) \quad (7)$$

where $q_0 = Q_{max}$ and the remaining coefficients $q_n$ and r are found from least squares fitting. Over the different tissue oxygenation states, we were able to obtain a maximum error of about 0.02 compared to the numerical solution of Eq. (5) using a polynomial of degree 4. Equation (7) enables us to average over the gamma distribution yielding:

$$OEC(\alpha, \beta) = Q_{max}\left(1 - \frac{1}{\Gamma(\alpha)}\sum_n q_n(k\beta)^n \frac{\Gamma(n+\alpha)}{(rk\beta+1)^{n+\alpha}}\right) \quad (8)$$

This procedure yields OEC by standard numerical techniques, with k as the only unknown parameter. When cooperativity and tissue oxygen tension are ignored, we find instead the expression $$OEC = 1 - (1+k\beta)^{-\alpha}. \quad (9)$$

Note that the assessment of OEC does not rely on independent measurements of absolute CBF, only the determination of transit time distribution, either by direct observation of RBC velocities by in vivo imaging techniques, or by residue detection experiments, tracking the passage of intravascular ultrasound, MR or CT contrast bolus passage (Østergaard et al., 1999).

Model Calibration

The model constant k was fixed to yield resting OEC=0.3 based on transit time data recorded by Stefanovic and colleagues (Stefanovic et al., 2008) during forepaw stimulation in a rat (their FIGS. 5.c. and 5.d.). Consequently, k was set to k=118 s$^{-1}$ throughout the study.

Effect of CTTH on Apparent Permeability Surface Area Product (PS)

We define the 'apparent' PS product derived from a given tracer by $$PS = -CBF \ln(1 - OEC) \quad (10).$$

Using the central volume theorem and assuming Grubb's relation in order to relate flow to transit time, we can estimate the apparent PS product for the experiments by $$PS(\tau, \sigma) = -CBF_0(\tau/\tau_0)^{1/g-1} \ln(1 - OEC(\tau, \sigma)) \quad (11)$$

In the resting state in (Stefanovic et al., 2008), we find a value of $PS(\tau_0, \sigma_0)$=17 mL/min/100 g, whereas under the functional activation, $PS(T_a, \sigma_a)$ was 44 mL/min/100 g, given the model presented here and assuming a resting state flow, $CBF_0$, of 60 mL/min/100 g. Had functional activation elicited a change in the mean transit time only, PS would have been $PS(\tau_a, \sigma_0)$=29 mL/min/100 g.

Thus, homogenization of capillary flows accounts for approximately $(PS(\tau_a,\sigma_a)-PS(\tau_a,\sigma_0))/(PS(\tau_a,\sigma_a)-PS(\tau_0,\sigma_0))$=56% of the change in the PS product during activation. Note that the change in the apparent PS product depends on the type of tracer through the value of the rate constant k. In the simple case where oxygen binding cooperativity and tissue oxygen tension are neglected, the explicit formula becomes $$PS(\tau,\sigma) = \alpha CBF_0(\tau/\tau_0)^{1/g-1} \ln(1+k\beta). \quad (12)$$

Analysis of Reported Transit Time Characteristics

Transit time distribution data were obtained from seven studies performed in rat (N=number of animals per group), including cortical electrical stimulation (control and 1.0-5.0 mA, N=6 by Schulte and colleagues (Schulte et al., 2003), their FIG. 7), mild (control and $P_aO_2$ 40 mmHg, N=5 by Hudetz and colleagues (Hudetz et al., 1997), their FIG. 2.A.) and severe ($P_aO_2$ 26 mmHg, N=5 by Krolo and colleagues (Krolo and Hudetz, 2000), their FIG. 3) acute hypoxia, graded hemorrhagic hypotension (Cerebral perfusion pressure 30-110 mmHg, N=6 by Hudetz and colleagues (Hudetz et al., 1995), their FIG. 4, assuming a gamma variate distribution of transit times), and mild (control and $P_aCO_2$ 50 mmHg, N=6 by Villringer and colleagues (Villringer et al., 1994), their FIG. 4) and severe hypercapnia (control and $P_aCO_2$ at 67 and 97 mmHg; N=5; Hudetz and colleagues (Hudetz et al., 1997), their FIGS. 2.B. and 2.C.). Reported RBC velocity (v) distributions were converted to transit time ($\tau$) distributions assuming $\tau=L/v$, where L=400 μm was the assumed length of the capillaries. For the hypercapnia study by Villringer et al, the distribution of blood cell fluxes during normocapnia and hypercapnia were read off from their FIG. 4. An average red blood cell linear density $\langle\rho\rangle$ in the two conditions was then estimated by the ratios of the average cell fluxes $\langle n \rangle$ and the average blood cell speeds $\langle v \rangle$: $\langle\rho\rangle = \langle n\rangle/\langle v\rangle$. (Note this rough estimate, is likely less certain than the approaches above). Finally, the distribution of blood cell fluxes were converted to a transit time distribution from $\tau=L\langle\rho\rangle/n$.

Net oxygen delivery capacity ($CMRO_2^r$) was determined by (i) assuming Grubbs CBF-CBV relation (Grubb et al., 1974) (converted to a CBF-MTT relation using the central volume theorem (Stewart, 1894)) with coefficient g=0.38 and (ii) transit time estimates obtained from reported hemodynamic data. For the resting state, CBF was inferred from the central volume theorem based on MTT and CBV=1.6%, resulting in a value of CBF=60 ml/100 ml/min. Furthermore, for the arterial oxygenation, a value of $C_{aO2}$=19 mL/100 mL was assumed in the resting state.

Patients

Patient 1, a 63 year old male with episodic left-sided hemiparesis caused by occluded right ICA, and patient 2, a 58 year old male with episodes of right-sided blindness due to a 90% stenosis of the right internal carotid, were both examined as part of a previous PET study (Ashkanian et al., 2009), in addition to which they were both examined by subsequent perfusion weighted MRI. Written informed consent was obtained from both subjects, and the study was approved by the Regional Committee on Research Ethics. PET scans were acquired and analyzed as described earlier, resulting in parametric maps of CBF, $CMRO_2$ and OEF in 128×128 matrices of 2×2 mm pixels with an isotropic resolution of 7 mm. PET-images were subsequently co-registered to MRI data and resulting PET-OEF re-sampled to the corresponding PWI-based OEC maps for direct comparison.

MRI Measurements

MRI was performed on a 3.0 T Signa Excite HR GE Imager (General Electrics Medical Systems, Waukesha, Wis., U.S.A.). Following a high resolution image sequence for co-registration, perfusion imaging was performed by acquiring dynamic Gradient Recalled Echo Planar Imaging (EPI) (Time of Repetition 1500 ms, time of echo 30 ms) during the passage of a 0.1 mmol/kg bolus of gadobutrol (Gadovist®, Bayer Schering Diagnostics AG, Berlin) injected at a rate of 5 ml/s, followed by a 20 ml bolus of saline. We acquired 21 slices, 5 mm thick with a 6.5 mm interslice gap with an in-plane resolution of 1.875 $mm^2$. Perfusion analysis was performed using a Bayesian procedure by which CBF, α and β in Eq. (1) are estimated using a Levenberg-Marquardt type Expectation-Maximization algorithm (Mouridsen et al., 2006b). The arterial input function for the perfusion analysis was identified by an automatic AIF search algorithm to avoid operator bias (Mouridsen et al., 2006a). Oxygen extraction capacity maps were then calculated using Eq. (4). Gold-standard mean transit time (MTT) maps were calculated using circular SVD (Wu et al., 2003).

Noninvasive Determination of Oxygen Extraction Capacity and the Maximum Retinal Oxygen Metabolism that can be Supported in Normal Volunteers and Patients with Diabetes We applied the model of oxygen extraction capacity (OEC) and the upper, theoretical limit on oxygen metabolism that may be supported ($CMRO_2^r$), as a function of mean transit time (μ) and transit time heterogeneity (σ), to data obtained by laser scanning i opthalmoscopy in the retina.

Data were reported in Arend et al. 1991. The authors reported red blood cell (RBC) velocities (mean and standard deviation) in 21 healthy volunteers and 48 diabetic patients. The diabetic patients were further subdivided according to the severity of their retinopathy: (1) No retinopathy (N=7); (2) mild to moderate retinopathy (n=17); (3) preproliferative retinopathy (N=10); proliferative neuropathy (N=14).

To apply the model, we assumed a capillary length of 1000 μm, a CBV of 1.6%, and an interstitial $PO_2$ of 25 mmHg. The paper reported the statistics of the velocities, while our model addresses transit times characteristics. We assumed that transit times have a gamma variate distribution, and used this fact to relate the velocity moments to the transit time moments.

The value of the rate constant k was found by using the mean transit time and heterogeneity of healthy patients and assuming a OEC of 0.3.

Figure 12:
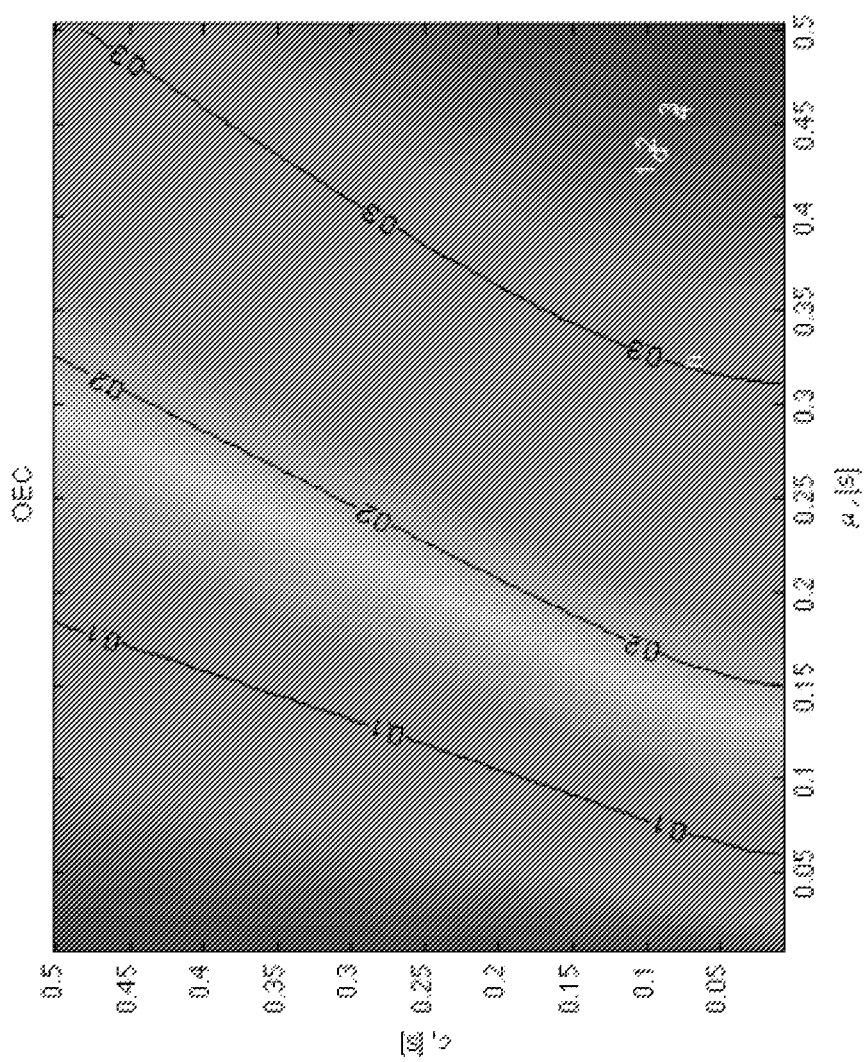
FIG. 12 shows an OEC plot in the retina of healthy and diabetic patients.

In the plots of FIG. 12, 'h' refer to healthy patients, 'd' to diabetic patients, and the numbers one through four to the categories of the diabetic patients above.

Alzheimer's Disease Increases Oxygen Extraction Capacity in Tempororparietal Lobe Due to Impaired Perfusion Introduction Alzheimer's Disease is considered a neurodegenerative disease, characterized by abnormal beta-amyloid metabolism and the formation of amyloid plaques and neurofibrillary tangles in the brain parenchyma.

The inventors have developed a model that allow assessment of the upper, biophysical limit to oxygen delivery to tissue based on residue detection data from conventional computerized tomography (CT) or magnetic resonance imaging (MRI), allowing direct assessment of microvascular limitations to oxygen delivery in patients.

Here the inventors test the hypothesis that Alzheimer's disease is associated with a loss of normal capillary flow heterogeneity, and that the resulting changes in oxygen extraction capacity correlates with patients symptomatology.

Methods & Materials

Subjects

Eighteen patients with clinically suspected possible or probable AD verified by ICD-10, DSM-IV and NINCDS-ADRDA were recruited as referrals from Demensklinikken, Aarhus University Hospital. The subjects in the patient group were only included if they obtained ≥20 points in the Mini-Mental-State Examination (MMSE) and were more than 40 years. Twenty age-matched controls were recruited in county of Aarhus and all controls performed in the normal range of neuro-psychological interview (MMSE score ≥28 points). Subjects in the both groups were excluded if they had diabetes mellitus type I and II, hypertension arterialis, suspicion of depression and suspicion of alcohol dementia. The mean age for the patient group was 72.9 (SD=5.1) years, and for the control group the mean age was 67.1 (SD=6.4) years.

Thirteen females were included in the patient group, and nine females were included in the control group.

Mean MMSE score for the patient group was 24.5 (SD=2.7) and for the control group mean MSSE was 29.4 (SD=0.7), see table 1, FIG. 13.

Image Acquisition

Multi slice T2* gradient-echo echo-planar images were acquired on a 1.5 T GE (GE Healthcare, Milwaukee Wis.) scanner with imaging parameters of TE=0.045 seconds, TR=1.5 seconds, 32 time slices of 16 images, 96×96 matrix with a field of view of 24

Of view 24×24, 5-mm-thick slices with 1.5-mm gap. Following an axial T1, GRE-EPI was performed during intra-venous bolus injection (5 ml/sec) of 0.2 mmol/kg gadobutrol (Gadovist®1.0 M, Schering) flushed by 20 ml saline.

Image Analysis

The perfusion data was used to estimate CBV, CBF, MTT, OEC and FH. The signal intensities were converted to concentration-time curves by: $C(t)=-\ln(S(t)/S_0)*(1/TE)$, where C(t) is the concentration, S(t) is the signal intensity and $S_0$ is the baseline signal intensity.

According to indicator dilution theory the contrast agent diluted in the tissue is given by:

$$C(t) = CBF \int_0^t C_a \tau R(t-\tau) d\tau,$$

where $C_a$ is the arterial input function. CBF is blood flow in tissue. R(t−τ) is the residue function describing the fraction of tracer still present in the tissue at time t and by means of residue function the hemodynamic in the voxel can be derived. We consider the above equation as a linear time-invariant system. The impulse to the system is arterial input function $C_a$, the impulse response is the measured concentration C and let the residue function be expressed by $$R = 1 - \sum_0^t h(t),$$

where the h(t) is the transport function. In the parametric approach of estimating the residue function we are minimizing the loss function $L=C(t)-C_a(t)R(t)$. The family of gamma distribution with scale parameter A and shape parameter β is sufficiently flexible for describing the residue function. The α's and β's are found by optimizing the loss function L using Levenberg-Maquardt type Expectation-Maximization algorithm described by Friston et al. 2003.

CBV is the area of R, CBF is the maximum of R, MTT is the product of a and β, OEC is given by $1-(1+P_c\beta)^{-a}$, where $P_c$ is the oxygen exchange rate constant and FH is the standard deviation of the residue function.

The individual perfusion maps in both groups were linear co-registered to Talairach space and blurred with a 3-dimensional Gaussian kernel (FWHM=8 mm).

Statistical Analysis

The statistical analysis was performed in the frontal lobe, temporal lobe and parietal lobe. To minimize inter-subject variations in perfusion values, the individual co-registered perfusion maps were normalized in order to mean perfusion value in white matter in semioval center. Two-sample t-test was used for ROI analysis of the mean perfusion values in the frontal, temporal and parietal lobe.

Results

Table 2, FIG. 13, gives the summary of the ROI analysis. Mean OEC and FH are significantly higher in patients compared with controls. In the Temporal lobe we observed no significant differences in OEC or FH between patients and controls.

Clinical Utility of Parametric Perfusion Estimates in Prediction of Final Outcome in Acute Stroke Introduction DSC-MRI (Dynamic Susceptibility Contrast MRI) parameters such as cerebral blood flow (CBF) and mean transit time (MTT) are important diagnostic maps, e.g. in acute stroke where they are used to identify ischemic regions. Non-parametric methods such as standard singular value decomposition (sSVD) or the timing-insensitive, block-circulant variant (oSVD), are commonly used to estimate perfusion parameters, but these methods produce highly fluctuating residue functions and high flow components are biased low. Recently, a parametric Bayesian approach, based on a physiological model of the microvasculature, has been shown to produce less biased flow estimates and produce smooth and monotonically decreasing residue functions in agreement with physiology. In addition, the oxygen extraction fraction (OEF) can be calculated based on the estimated capillary flow distribution. However, the clinical utility of perfusion estimates depends on their ability to correctly predict final infarct size. Here we use voxel-wise predictive algorithms to compare the predictive strength of sSVD, oSVD and parametric perfusion parameters.

Materials and Methods

Standard perfusion and diffusion weighted images were acquired for n=28 patients with acute stroke. All patients were treated with rtPA and a follow-up T2 scan was performed after 3 months. Final infarcts were outlined by a neuroradiologist. N=16 patients with final infarcts larger than 5 ml were included in the analyses. MTT was calculated using sSVD, oSVD and the parametric model (denoted sMTT, oMTT and pMTT). In addition, OEF was calculated based on the parametric model as described above To quantify the predictive strength of each deconvolution approach, a logistic regression model was trained for each perfusion parameter separately using jack-knifing (Wu et al, Stroke 2001). DWI and T2 were also included in each model. The training set was balanced and consisted of voxels in the outcome lesion and healthy voxels from both the contra-lateral hemisphere and the diffusion/perfusion mismatch region. Predictive performance was measured using the area under the receiver operating characteristics curve (AUC). This was evaluated in the region corresponding to prolonged MTT, such that the calculated AUC ($AUC_R$) reflects the ability to separate infarcting from non-infarcting voxels in the most critical region. ($AUC_R$) is taken as a conservative estimate of overall model performance. AUC was also computed using all brain voxels, which is more common ($AUC_V$).

Results

Figure 14:
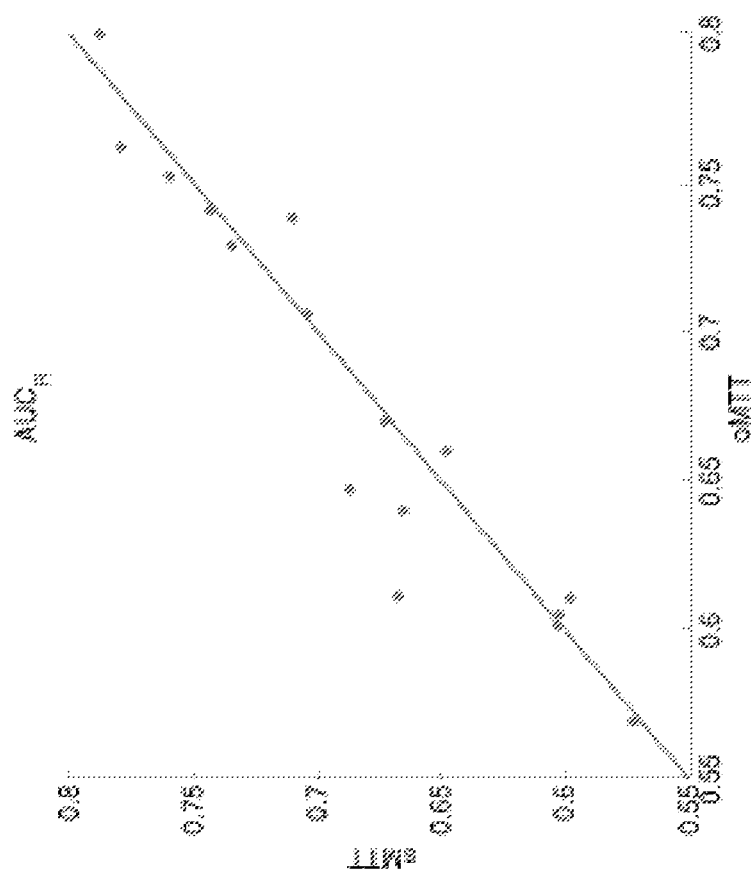
FIGS. 14, 15, and 16 show various receiver operating characteristics curves ($AUC_R$ and $AUC_{WB}$) versus oMTT/sMTT, pMTT/oMTT, and OEF/oMTT, respectively.
Figure 15:
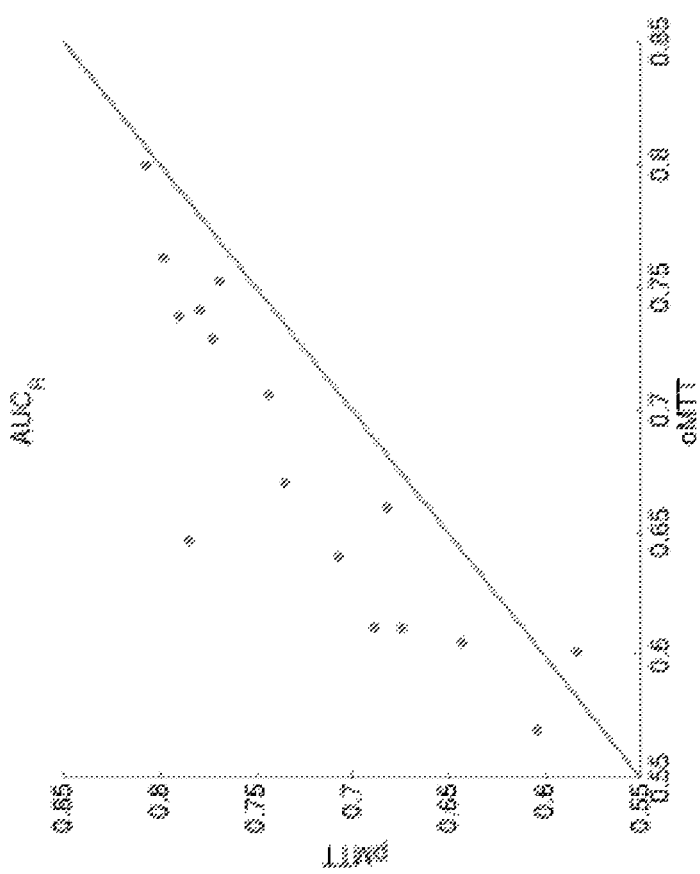
Figure 16:
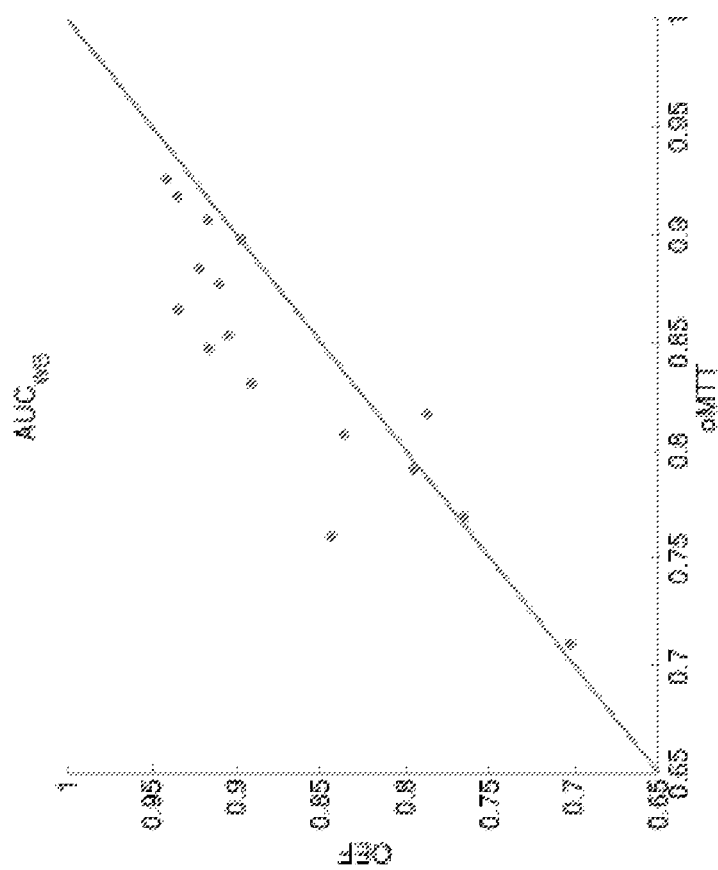

No difference in predictive performance was found between oMTT and sMTT (Wilcoxon, p=0.33). For oMTT median $AUC_R$=0.68, inter quartile range (IQR) [0.61; 0.74] and for sMTT median $AUC_R$=0.68, IQR [0.63; 0.74]. FIG. 14 further indicates the similarity between oMTT and sMTT. In contrast, pMTT yielded significantly (Wilcoxon, p<0.001) higher performance (median $AUC_R$=0.74, IQR [0.68; 0.78]) compared to oMTT. Moreover, as seen in FIG. 15, performance of pMTT was higher in 15 out of 16 patients (Exact binomial test, p<0.001). Similar results are observed when AUC is calculated using all brain voxels, where pMTT also leads to significantly increased performance compared to oMTT (Wilcoxon, p=0.01). OEF (median $AUC_V$=0.90, IQR [0.82; 0.92]) leads to significantly better overall performance than oMTT ($AUC_V$=0.85, IQR [0.80; 0.89]), Wilcoxon, p<0.01 (see FIG. 16), although the improvement in $AUC_R$ was not significant (p=0.15).

Conclusion

Mean transit time calculated based on the Bayesian parametric model leads to significantly improved prediction of final infarct size using both performance measures ($AUC_R$, $AUC_V$) compared to the SVD methods. Moreover, the best ($AUC_V$) performance was observed using OEF. In contrast, no significant difference was found between sSVD and oSVD estimates using either performance measure. This suggests an improved clinical utility of perfusion estimates based on the vascular model (Mouridsen et al, Neuroimage 2006) compared to SVD methods.

Assessment of Functional Hemodynamic in an Acute Stroke Patient with Contrast Enhanced Ultrasound Imaging (CEU)

Introduction

In this study we assessed the functional hemodynamic in an acute stroke patient with contrast enhanced ultrasound imaging (CEU). We expect that the Mean-Transit-Time (MTT) is prolonged on the ipsi-laterale (IL) hemisphere due to the occluded vessel and accordingly an elevation of Oxygen Extraction Capacity (OEC) is expected. Due to the ischemic conditions in the brain tissue, we expect dysfunctional flow regulation and hereby increased Flow-heterogeneity (FH) on IL hemisphere.

Method

A 53-year old male was admitted after symptoms of stroke admitted after acute onset of left sided hemiparesis due to MCA thrombosis. We assessed the functional hemodynamic by means of CEU. Parts of the ipsi-lateral parietal lobe were imaged via the temporal acoustic window in an oblique plane. A bolus of 0.3 ml ultrasound contrast agent (SonoVue®, Bracco, Milano, Italy; solution prepared as recommended) followed by 5 ml saline flush was administered while obtaining a 2 min. cine-loop of the above described part of the brain. The ultrasound system settings were the following: framerate: 18 Hz, gain: 57%/63% (ipsi/contra) and compression: 50. Images obtained by CEU were logarithmic compressed in order to facilitate visual interpretation. We linearalized the data in order to obtain linear relationship between the contrast concentration and image intensity. Subsequently, a temporal low-pass filtration and down sampling of data was performed achieving a repetition time (TR) of 1 s. Finally; the images were spatially averaged and down-sampled by a factor 0.25. The images were averaged in regions to improve the SNR and were afterwards down-sampled to remove redundant data. In order to determine the perfusion parameters OEC, FH and MTT we applied the parametric vascular model (Mouridsen et al, Neuroimage 2006) to CEU data.

Results

On the IL hemisphere we found elevated MTT (MTT=1.36) compared to the contra-laterale (CL) hemisphere (MTT=2.26), and consequently the OEC was elevated on the IL hemisphere (OEC=0.45) compared to the normal side (0.26). We observed the highest FH on the contra-lateral hemisphere, FH=1.66 (IL FH=1.32).

Discussion

In this study we assessed the functional hemodynamic of an acute stroke patient with CEU. We found elevated MU, OEC and FH on the IL hemisphere as expected. A computational issue actually overestimated the perfusion parameter estimates on CL hemisphere. We observed a secondary peak followed by a plateau on the tissue curve around 60 sec (not shown), which is possibly caused by motion artifact. This peak and plateau skews the fitted gamma variate rightward and consequently increases the perfusion parameters.

Ongoing Project on Measurements of Heterogeneity of Retinal Capillary Flow

System 1. Screening of Active Pharmaceutical Ingredients

Optical Methods

Retinal vessels from humans or experimental animals mounted in vitro with or without perfusion, either as isolated vessels, as vessels with preserved perivascular tissue, or as vessels studied as a part of larger retinal segments or the whole retinal vascular system, combined with:

A microscopical setup that allows video recordings of changes in the diameter and/or the perfusion of several retinal arterioles or capillaries simultaneously with the purpose of studying heterogeneity of the retinal microcirculation.

Bio Markers

Examination of the following parameters simultaneously in several retinal vessels The flow (velocity and density) of the formed elements of the blood using fluorescence and other markers The diameter of retinal vessels The oxygen tension in and around the retinal vascular system pH in and around the retinal vascular system System 2. Diagnostics Optical Methods Simultaneous evaluation of the flow in capillaries from several different microcirculatory units as studied on single or serial (video) images of the retina, especially including:

Retinal angiography

Scanning laser ophthalmoscopy

Laser Doppler flow metry

Adaptive optics retinal scanning

Orthogonal Polarization Spectral (OPS) imaging

Sidestream dark-field (SDF) imaging

Image (or video) recordings that enable the measurement of vascular diameters.

Bio Markers

Simultaneous evaluation of one or several of the following parameters from different vascular areas:

Retinal flow

Vessel diameter

Capillary transit time heterogeneity: a regulating factor to oxygen delivery to exercising skeletal muscle tissue in humans. (A putative contributor for the development of vascular diseases?). How CTTH accounts for features of T2DM For a long time, capillary recruitment has been synonymous with the capillaries' ability to gradually open as exercise demands increase. However, the existence of capillary recruitment seems redundant as several studies have shown that capillary transit time heterogeneity (CTTH) affects the efficacy of oxygen extraction in different tissues: a physiological phenomenon that becomes even more evident during exercise. Actually, it is widely recognised that exercise reduces CTTH, consequently securing muscle tissue oxygenation. In this study, we investigated whether graded handgrip intensity reduces CTTH in ten healthy humans in vivo using contrast enhanced ultrasound technique (CEUS). Our results demonstrate that CTTH affects the efficacy of oxygen extraction capacity (OEC): CTTH decreases from 3.91±0.87 sec. at rest to 1.73±0.25 sec. in response to exercise, consequently improving OEC from 30±3% at rest to 59±3%, respectively. Findings in residual plot analyses suggest that a gradual decrease in CTTH is associated with gradually improved OEC during graded handgrip exercise. Additionally, it has been demonstrated that muscle tissue oxygenation is critically dependent on capillaries (however by a mechanism that cannot be detected by CEUS). These findings seem to provide further understanding of the capillaries' ability to supply oxygen to working skeletal muscle in a homogenous/heterogeneous fashion: not, as previously thought, through opening of more capillaries (i.e. capillary recruitment). Obviously, this may not only have effects on muscle tissue oxygenation during exercise, but CTTH may also be a critical hemodynamic parameter in understanding different vascular diseases, such as type 2 diabetes (T2D).

The regulation of micro vascular blood perfusion has rich history of investigation and every microcirculationist has been puzzled by the capillaries' ability to adapt in response to exercise. It is well known that muscular oxygen uptake depends on extrinsic factors, including for instance oxygen supply and intrinsic factors, which regulate both the transfer of oxygen from the red blood cells (RBCs) to the mitochondria and the following utilisation of oxygen inside the mitochondria. Immensely influenced by August Krogh's capillary recruitment model (CRM) proposed almost a century ago, many microcirculationists use this model to explain that capillaries make use of a great capillary reserve (i.e. recruitment) during exercise in order to meet an increased blood-myocyte oxygen demand. However, in the light of considerable evidence gathered over the last 3 decades, we may call for a paradigm shift in our understanding of micro vascular blood perfusion.

Microcirculation According to Krogh and Bohr-Crone-Kety-Renkin Equation (Crone 1963):

Our inspiration from Krogh originates from his incredible work in exercising guinea pig and frog muscles in which he showed that capillaries serve as the critical site for augmented blood-myocyte oxygen flux, which gradually was increased during exercise (Krogh, 1919). Subsequently, among the most remarkable findings in these experiments, Krogh demonstrated that it is not adequate only to distribute a sufficient amount of oxygen to a specific organ, but oxygen has to be distributed within that particular organ precisely where it is required (Krogh, 1919). Consequently, it must be recognized that not only bulk blood flow, but particularly its appropriate distribution between and inside exercising skeletal muscles is immensely important for the exact moment-to-moment matching of oxygen delivery and metabolism. Having demonstrated this diffusive transport, Krogh argued that capillaries themselves are part of the regulation of nutrient supply by capillary recruitment (Krogh, 1919): i.e. opening of previously closed capillaries in order to augment the muscle's total capillary surface area available for substance diffusion.

Figure 17:
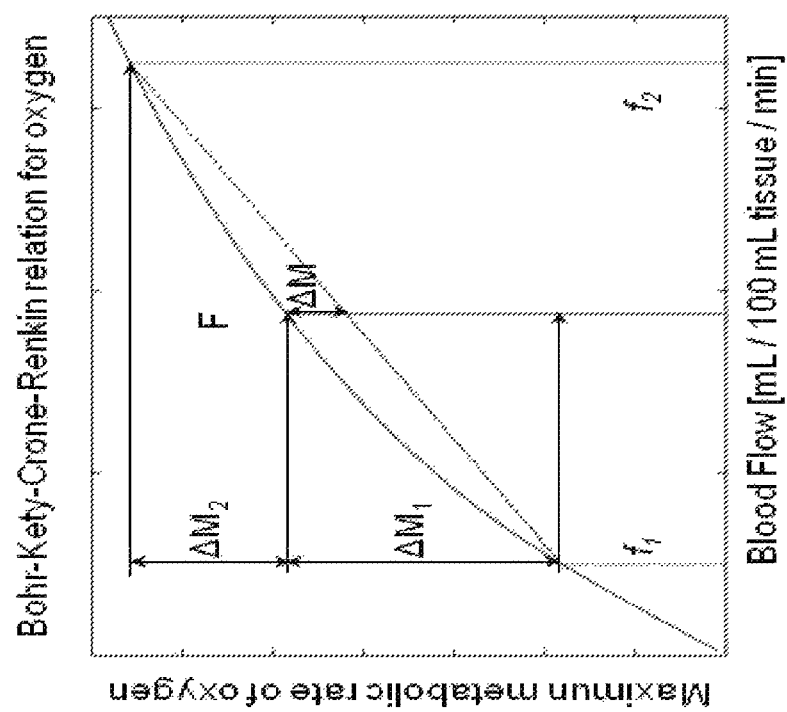
FIG. 17 shows a grey curve that represents the maximum amount of oxygen, which can diffuse from a single capillary into the tissue for a given tissue blood flow (mL blood per 100 mL tissue per minute). The curve shape determines three critical characteristics of oxygen diffusion into tissue: 1) the curve slope decreases towards high flow values, making flow increases gradually more inefficient. 2) if tissue capillaries—instead of all having equal flows and transit times as assumed by the classical Bohr-Kety-Crone-Renkin (Crone 1963) equation—were split into two equal-size populations with flows f1 and f2, then net tissue blood flow would remain unaffected, but oxygen availability would be reduced by ΔM. Thus, capillary transit time heterogeneity (CTTH) does affect tissue for a given flow, even without classical capillary recruitment. 3) the loss of oxygen availability in cases in which capillary flows in this way are reduced to f1, ΔM1 is always greater than the increase of ΔM2 of the remaining capillaries, receiving the remaining flow, f2. This phenomenon dramatically reduces the extraction efficacy.

Another model that has been widely accepted for elucidating the preservation of moment-to-moment muscle oxygenation is the Bohr-Kety-Crone-Renkin (BKCR) flow-diffusion equation. Accordingly, in order to secure moment-to-moment oxygenation of muscle tissue during exercise, blood flow increases through a capillary, thus also oxygen availability to the tissue (see FIG. 17). Additionally, the equation includes de facto that oxygen availability increases with capillary permeability and surface area.

Intuitively, both Krogh's CRM and the BKCR equation seem two perfect theories to demonstrate the adaptation of microvasculature in response to exercise: accordingly, at rest there is a great unused reserve in the capillary bed, which in response to exercise will open to meet the metabolic demands (i.e. capillary recruitment), consequently increasing the muscle's total capillary surface area for greater extraction of oxygen, glucose and free fatty acids as well as reducing the diffusion distance between capillary to mitochondrion (i.e. the BKCR equation). Thus, until now, traditional microcirculationists have rendered a continuous topicality of the CRM probable by capillaries' ability to gradually open in response to exercise as well as Krogh's CRM even today have been accepted at face value. Obviously, the traditional BKCR equation supports this, making the CRM even harder to oppose against. However, just as much as these theories seem an important integrative part of modern physiology, our underlying perception should perhaps be modified in the light of considerable evidence gathered over the last 3 decades has revealed that nearly all red blood cells (RBCs) transit through the entire capillary bed, both at rest and during exercise. Therefore, we aim to take the Popperian glasses on in a view to falsify the traditional CRM, as it seems to have some decisive intrinsic errors that have been overlooked in understanding moment-to-moment muscle tissue oxygenation.

Critical Appraisal of Krogh's CRM:

Is capillary recruitment from rest to exercise in fact physiologically possible? Microcirculationists that are ardent supporters of the CRM seem to have two fundamental problems: 1) nearly all—if not all—capillaries are perfused by RBCs probably controlled by adjacent pericytes (Vimtrup, 1922) and 2) not any scientist truly observes the capillaries in his experimental settings to support capillary recruitment.

Initially, Krogh himself acknowledged some intrinsic problems in his model that most likely would have supported RBC flux in the entire capillary bed if solved: the India ink particles clumped together, thus blocking opening to some capillaries, which might have been reduced or even eliminated at higher flow rates and the extreme surgical procedures often indispensable to attain good perfusion (Krogh, 1919). Obviously, these observations make the CRM somehow questionable, as to how muscle perfusive and diffusive oxygen conductances increase manifold in response to exercise. Another conspicuous consequence using the CRM is its extreme increases of haemoglobin in response to exercise,—presumably up to times as many compared to rest—which intuitively also seems erroneous. To our knowledge, no microcirculationist of the traditional CRM has ever demonstrated this. In fact, using NIRS technology in human skeletal muscle has revealed only a minor haemoglobin increase of approximately 20% in response to dynamic knee extension exercise (Lutjemeier et al., 2008). A third concern that also may conflict with the existence of traditional recruitment is anaesthetics, which in some cases reduce blood pressure to levels that induce skeletal muscle hypoperfusion owing to lack of driving pressure that may be exacerbated by a sympathetically mediated muscle vasoconstriction (Poole et al., 2011). Additionally, considerable research from the last three decades demonstrates that nearly all capillaries undergo perfusion in resting muscle, thus precluding capillary recruitment. Accordingly, direct observations reveal that more than 80% of red blood cells (RBCs) in resting muscles in rats transit through the capillary bed (Kindig et al., 2002; Poole et al., 1997; Hudlicka et al., 1982; Burton & Johnson, 1972), whereas others describe fully perfused capillaries at rest (Erikson & Myrhage, 1972). Subsequently, these observations are in great dispute with the capillary recruitment model, since only a small fraction of RBCs will transit through the entire capillary bed at rest. Interestingly, more than 25 years ago, capillary recruitment was suggested to be redefined, as the spatial distribution of RBCs most likely transited capillaries in a heterogeneous fashion at rest, becoming relatively less heterogeneous during exercise (Tyml, 1986). In fact, within the last decade, there is establishing evidence saying that blood perfusion is heterogeneous during rest, gradually becoming more homogeneous during endurance training (Laaksonen et al., 2010; Kalliokoski et al., 2004; Kalliokoski et al., 2003a; Kalliokoski et al., 2001). Additionally, capillary recruitment has also been precluded after direct observations of RBCs transit through the capillary bed in brain (Villringer et al., 1994; Kuschinsky & Paulson, 1992; Pawlik et al., 1981). Additionally, to our knowledge, pericytes have never been included in the explanation of potential capillary recruitment. However, in various animal models, pericytes have shown to control capillary perfusion through their spontaneous relaxation-contractility properties (Peppiatt et al., 2006; Hirschi & D'Amore, 1996), also proposed by Krogh himself (Krogh, 1919). Thus, under optimal non-confounding conditions, pericytes allow RBCs to transit through the entire capillary bed in a heterogeneous or gradually less heterogeneous fashion in order to supply oxygen according to the metabolic demand at rest or during exercise, respectively. Furthermore, the BKCR equation may even help us more to appreciate capillary perfusion as dynamic and constantly changing. Though, the classical BKCR flow-diffusion equation is limited by its intrinsic extraction property based on only one idealised capillary, redefining the model gives us a far more accurate answer to the hemodynamics of capillary perfusion, including de facto that capillaries in muscle tissue are part of a highly interconnected and tortuous arrangement, which display great variability among muscle groups (reference). Given the highly heterogeneous structures of capillary anatomy, the BKCR equation also predicts that any differences in perfusion among coupled capillaries reduce the efficacy of oxygen extraction relative to the model's estimates, however with an unaltered total capillary flow output. Microcirculation already uses this property to maintain high oxygen extraction during high flow conditions: capillary transit time heterogeneity (CTTH) is reduced in response to increased metabolic demands (Kalliokoski et al., 2004). Therefore, the parallel coupling of capillaries in tissue compensates for the inherent, poor extraction efficacy of single capillaries at high flows (see FIG. 17) and, contrary to earlier beliefs, allows the capillary bed to regulate extraction efficacy, without traditional recruitment. Accordingly, all these observations suggest that in order to secure moment-to-moment muscle tissue oxygenation, the CRM and its subsequent reduction of blood-myocyte diffusion distances seem erroneous. Rather, oxygen diffusion from capillaries to tissues is dependent on the time that the RBCs use to transit through the capillary bed, consequently affecting the oxygen extraction. Interestingly, CTTH may be one of the regulating factors to oxygen delivery in exercising skeletal muscles.

Our Comments to Krogh's CRM:

One factor that may answer how muscle diffusive oxygen conductance manifold in response to exercise, is the heterogeneous transit times of RBCs. Thus, it has been demonstrated that CTTH reduces concurrently with increasing blood flow during exercise in humans and different animals (Kalliokoski et al., 2004; Kayar et al., 1994). In vascular diseases, it is demonstrated that perfusion heterogeneity and CTTH are high, however greatly influenced by the character of the disease (Ellis et al., 2002; Humer et al., 1996; Kayar et al., 1994). In response to endotoxemia and sepsis, animal studies have also shown that increased perfusion heterogeneity is coupled with an increased mismatch in O2 demand and supply, consequently leading to an impaired oxygen extraction (Ellis et al., 2002; Humer et al., 1996). Another study has demonstrated that CTTH increases in the gut of endotoxemic pigs, consequently suggesting impaired oxygen extraction (Humer et al., 1996). Though not in continuation of these observations, it has been demonstrated that patients with T2D along with micro vascular complications have impaired capillary recruitment (Womack et al., 2009): this condition, however, we interpret as having a high CTTH.

Naturally, provided the validity in these studies, we may find ourselves in a time, in which we should call for a paradigm shift in our understanding of exact moment-to-moment muscle tissue oxygenation. Recently it has been suggested that blood flow and CTTH act in concert to closely match metabolic needs (Jespersen & Østergaard, 2011). Therefore, it is our aim to attempt to 1) demonstrate that capillary transit time heterogeneity is reduced during increased handgrip intensity (intermittent static), ultimately increasing oxygen extraction capacity (OEC), 2) show that contrast enhanced ultrasound technique (CEUS) can be used to measure these micro vascular changes—both hypotheses to support that all capillaries are perfused, both at rest and during exercise. And 3) establish a framework that show the consequences of appropriate vs. inappropriate muscle tissue oxygenation, consequently summing up the advantages and challenges, which the health care system faces.

Methodology:

Study population: A total of 10 test subjects (27.2±5.3 yr, 173±10 cm, 67.9±14.9 kg) volunteered for the experiment. Test subjects were recruited through advertisement at Department of Sports Science at Aarhus University. They were all given both oral and written information about the purpose, nature and potential risks before they gave a written informed consent to participate in the study. The subjects were requested to meet fasting and at least 3 hours after the subjects had eaten. Not any of the subjects were taking regular medication. The local Human subject Ethics Committee of Region Midtjylland approved the experiment and procedures applied.

Study design: skeletal muscle blood perfusion around the flexor region of the forearm was measured using CEUS with SonoVue®, as described in details below. Initially, skeletal muscle blood flow/perfusion was measured under normal resting conditions and then immediately after each intensity handgrip force (25% and 80% of individual maximal handgrip force). The maximal force generated on a calibrated Saehan handgrip ergometer was determined for the subject's dominant arm, with the total of 3 attempts used, which subsequently was used to calculate the handgrip forces of 25% and 80%. During the experiment, the handgrip ergometer was placed with its display against each test subject (all in a sitting position), thus one could follow the generated force that one was obligated to meet. Additionally, a timer was placed in front of each subject in a view to giving a visual signal to ensure the correct timing. A person from the research group also secured this by orally urging each test subject every 5 seconds to perform the requested force. All test subjects implemented the experiment. Before the experiment, an anatomical imaging above the flexor muscles of the subject's forearm was obtained as well as the first scan of capillary flow patterns were registered at rest. Afterwards, each test subject performed a 1-second handgrip exercise, once at 25% and at 80% of their pre-determined maximal force value every 5 seconds for 2 minutes. Immediately after each handgrip exercise, SonoVue® and saline injection were infused in the antecubital vein of the non-dominant arm, and another person from the research group scanned with a L9-3 (L17-5 only for anatomical imaging) linear transducer above the flexor muscles of the subject's forearm.

Blood Flow Measurements and Analysis:

A developed Vascular parametric model

Subjects with recent acute coronary syndrome or clinically unstable ischemic cardiac disorder (e.g. myocardial infarction, acute heart failure or severe rhythm disorders) were excluded. Additionally, smoking, obesity, pregnancy and breast-feeding also excluded potential subjects. Subjects that were included, were healthy and between 22 and 36 of age.

Statistical Methodology:

Data were analysed using Math Works. To test whether the data was normally distributed, the Lilliefors was applied. All data fulfilled the criterion of a normal distribution, consequently using the student's t-test to measure statistical differences. In all statistical analyses, the level of significance is set to $p<0.05$. All results are expressed as mean±standard error of the mean (SEM). Additionally, to test the relation between CTTH and OEC, a residual plot was applied.

Figure 18:
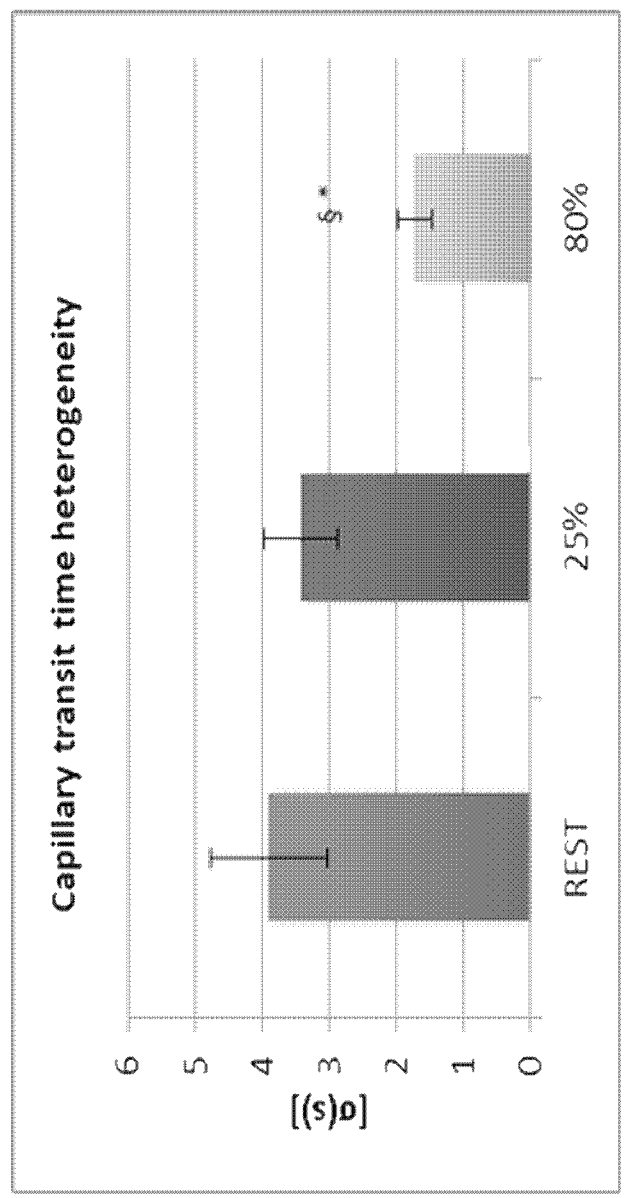
FIG. 18 shows the average capillary transit time heterogeneity at rest and during different exercise intensities (25% and 80% handgrip forces). § P<0.02, comparison between rest and 80% handgrip force. *P<0.01, comparison between 25% and 80% handgrip force.

Results:

Handgrip exercise decreased CTTH (see FIG. 18) by 56% from rest to 80% at their pre-determined maximal force (from 3.91±0.87 sec. at rest to 1.73±0.25 sec. at 80%, $P<0.02$), and by 50% from 25% to 80% handgrip forces (from 3.42±0.56 sec. at 25% to 1.73±0.25 sec. at 80%, $P<0.01$).

Figure 19:
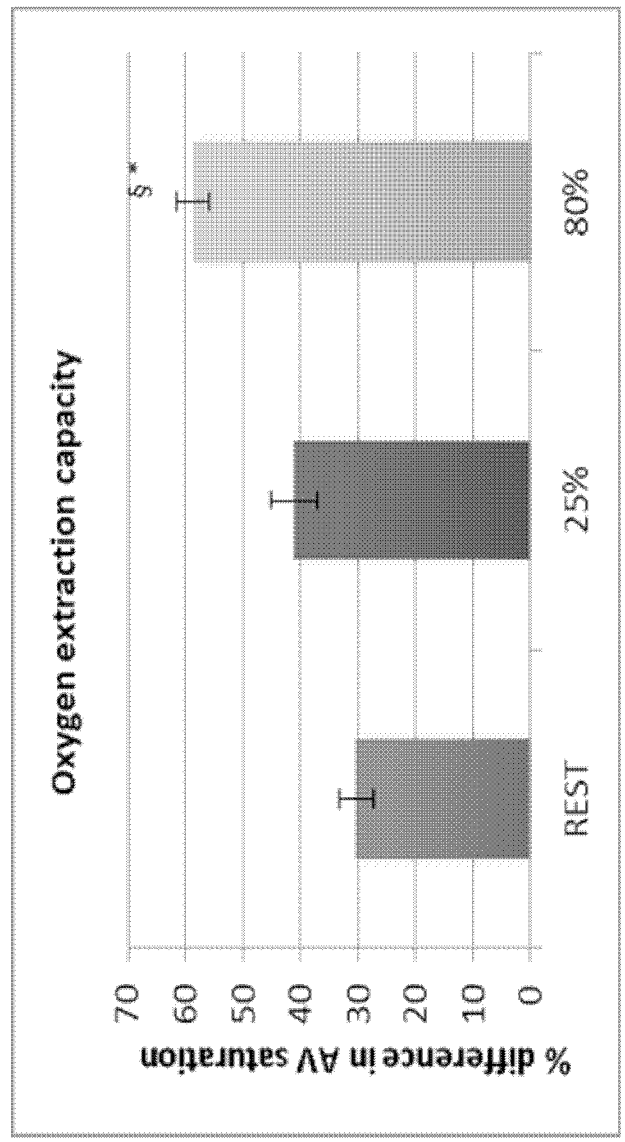
FIG. 19 shows the average oxygen extraction capacity at rest and during different exercise intensities (25% and 80% handgrip forces). § P<0.001, comparison between rest and 80% handgrip force. *P<0.01, comparison between 25% and 80% handgrip force.

Additionally, OEC increased in response to graded handgrip force (see FIG. 19). Consequently, OEC increased by 94% from rest to 80% handgrip force (30±3% at rest to 59±3% at 80%, $P<0.001$). Furthermore, between 25% and 80% handgrip forces, OEC increased by 44% (41±4% at 25% handgrip force to 59±3% at 80% handgrip force, $P<0.01$).

Between rest and 25% handgrip forces, no significant changes were observed in either CTTH ($P=0.50$) or OEC ($P=0.054$).

Finally, a residual plot (FIG. 3) between CTTH (abscissa axis) and OEC (ordinate axis) demonstrates how these hemodynamic parameters are interrelated under various handgrip intensities.

Discussion:

In the present study, it is demonstrated that less capillary transit time heterogeneity was associated to improve oxygen extraction capacity in human forearm muscle during graded intermittent static exercise. Consequently, this suggests that CTTH most likely is a regulating factor to oxygen delivery to exercising skeletal muscles. Additionally, we also show here that the vascular parametric model in CEUS most likely could be used to measure different hemodynamic parameters, including oxygen extraction capacity and capillary transit time heterogeneity.

CTTH: Its Functional Importance in Exercise and Disease

CTTH is a critical physiological parameter, because it may be one of the regulating factors to oxygen delivery to working skeletal muscles. Consequently, as oxygen diffuses across the capillary wall to muscle tissue, the time that blood stays in capillaries has a direct impact on the oxygen extraction (Honig & Odoroff, 1981). In this study, the results suggest that changes in CTTH (measured by the standard deviation a of transit time across the capillary bed) deeply influences the OEC for a given MBV/MP ratio (expressed as mean μ). Subsequently, this in vivo study demonstrates that graded handgrip exercise decreases CTTH by 56% (from rest to 80% handgrip force) and 50% (from 25% to 80% handgrip forces). These reducing findings are in agreement with other earlier studies, though the average decrease in CTTH found in this study was different than observed by other research groups (Kalliokoski et al., 2004; Tyml, 1986). Thus, in one study, micro vascular transit time heterogeneity decreased approximately 20% between rest and isometric exercise at 10% of maximal voluntary contractions (Kalliokoski et al., 2004). Another study conducted by a Canadian scientist revealed that electrical stimulation of frog muscles decreased transit time heterogeneity (Tyml, 1986). Though not observed in skeletal muscle, a study conducted on endotoxemic pigs showed that CTTH increased compared with the control group (12.3±4.9% versus −5.8±7.4%), thus suggesting that it impairs oxygen extraction during sepsis (Humer et al., 1996). However, other researchers have found no relation between transit time heterogeneity and oxygen extraction in canine intestine (Connolly et al., 1997). Rather, it was demonstrated that gut oxygen extraction is affected by redistribution of blood perfusion between different layers of the gut. In another study with 82 patients with left-to-right intracardiac shunts, the cardiopulmonary transit time heterogeneity in patients with moderate to severe shunts was increased (49±9%) compared with control patients (39±7%), who had no evident shunts (Kuikka et al., 1999). Thus, despite the fact that the concept of capillary transit time heterogeneity in skeletal muscle is relatively unexplored, both the obtained results and the other presented results suggest that it might be a critical parameter that potentially has an effect on the oxygen extraction capacity, both in a healthy and diseased state.

Capillary Transit Time Heterogeneity Versus Capillary Recruitment:

There is considerable evidence indicating that capillary recruitment can be stimulated by exercise (Womack et al., 2009; Rattigan et al., 2005), cold and hypoxia (Bourdillon et al., 2009; Parthasarathi & Lipowsky, 1999). Thus, the CRM has been generalised—and widely accepted—to explain the regulation of micro vascular hemodynamics during various states of adequate tissue oxygenation. However, as our model predicts, the efficacy of oxygen extraction is merely dependent on the temporal heterogeneity of capillary transit times, rather than capillary recruitment in order to secure tissue oxygenation.

OEC: Its Functional Importance in Exercise

In this study, it has been demonstrated that graded handgrip work improves OEC, which consequently enhances muscle oxygen supply. Naturally, this is rather crucial in order to meet the metabolic demand of a working muscle. Additionally, according to the presented results, muscle oxygen extraction may be critically dependent on capillary transit time and its heterogeneity. Other similar studies also suggest that CTTH affects the efficacy of oxygen extraction (Kalliokoski et al., 2004; Humer et al., 1996).

In this study, the OEC of resting muscle is 30±3% in healthy subjects (see FIG. 2 above). To a certain extent, this result is in agreement with the results found by two Finnish research groups (Laaksonen et al., 2010; Kalliokoski et al., 2001), who demonstrated a resting oxygen extraction capacity of 32±12% and approximately 30%, respectively. Additionally, a recently published study also demonstrates that oxygen extraction capacity in resting muscle is approximately 30% (Heinonen et al., 2011). Additionally, same study also demonstrates that resting OEC is increased by both NOS inhibition alone and by combining both NOS inhibition and cyclooxygenase (COX) inhibition, thus suggesting the importance of NO in blood flow regulation (Heinonen et al., 2011). Furthermore, another research group, who compared arm and leg maximal oxygen extraction in six elite cross-country skiers, demonstrated that resting oxygen extraction in arms is approximately 30% (Calbet et al., 2005). Therefore, it is reasonable to suggest that resting oxygen extraction capacity presented in this study is consistent with the other presented studies.

The obtained results from graded muscle work (25% and 80% handgrip exercises) seem to be in agreement with other studies. The oxygen extraction capacities obtained in this study during 25% and 80% handgrip forces were 41±4% and 59±3%, respectively. Though never having applied the vascular parametric model to CEUS before (at least to our knowledge), the obtained oxygen extraction capacities in human arm during graded muscle work are in approximate accordance with other studies (Laaksonen et al., 2010; Kalliokoski et al., 2004; Kalliokoski et al., 2003b; Kalliokoski et al., 2001). Subsequently, graded muscle work in legs is associated with increased oxygen extraction. Though not comparable in intensity with this study, Kallikoski and co-workers demonstrated an oxygen extraction of 45±11% during isometric leg muscle contractions at 10% of maximal voluntary contraction (Kalliokoski et al., 2004). Same research group conducted a similar study three years earlier, in which it demonstrated that trained subjects had an oxygen extraction of 49±14% versus untrained subjects, whose oxygen extraction capacities were 29±12% (Kalliokoski et al., 2001). Additionally, a mixed protocol of continuous and intermittent exercises revealed that the oxygen extractions during 10% isometric leg muscle contraction and 5% continuous static exercises were 37±22% and 30±23%, respectively (Kalliokoski et al., 2003b). Furthermore, one study has demonstrated oxygen capacities during isometric leg muscle contractions at 50% of maximal voluntary contraction (before and after low intensity) are 62±7% and 70±7%, respectively (Laaksonen et al., 2010). Thus, the results from the presented studies seem to be relatively comparable with the results presented in this study, as arms extract less oxygen than legs with the same intensity (Calbet et al., 2005). Furthermore, it is worth mentioning that the volunteered subjects in this study are moderately trained, thus showing that muscle tissue oxygenation is critically dependent on gradually homogeneous flow patterns in capillaries. Moreover, from these results it seems reasonable to speculate that the efficacy of oxygen extraction capacity is improved by regular exercise (also demonstrated by Kalliokoski and co-workers in 2001).

Methodological Considerations:

Despite the fact that the concept of capillary transit time heterogeneity has been applied for a relatively long time, the methodological approaches to measure CTTH are somewhat different. Traditionally, PET- and MRI-scans have been considered the most accurate methods to measure regional muscle blood perfusion in humans (Frank et al., 1999). Additionally, NIRS has also proven highly accurate for same purposes (Boushel et al., 2000). Within the last decade, CEUS has gradually become an accepted method in muscle perfusion measurements during exercise (Womack et al., 2009; Krix et al., 2009; Rattigan et al., 2005). However, the validity of CEUS has been rather poor; to our knowledge only two studies have attempted to 'validate' CEUS and this has been against muscle biopsy and venous occlusion plesthymography (Weber et al., 2006; Krix et al., 2005). However, only one study has attempted to find the relationship between backscattered intensity and contrast agent concentration, which is believed to be the primary objective in validating CEUS (Lampaskis & Averkiou, 2010). In this study, we initially also tested the relationship between backscattered intensity and SonoVue® concentration (0.15 ml, 0.30 ml and 0.40 ml were used) in order to confirm linearity (figure not shown). Consequently, we avoided any scenario of potential shadowing, which potentially would have resulted in different measurements (Lampaskis & Averkiou, 2010). Additionally, we also used a mechanical index (MI) of 0.07, thus reducing the risk of early bubble destruction. Therefore, the obtained results from this study indicate that CEUS most likely is a valuable method that brings accurate information about micro vascular changes during exercise; perhaps equally to other scan approaches. However, more studies are needed to further establish any validity of CEUS.

Functional Importance of CTTH in Micro Vascular System

Figure 20:
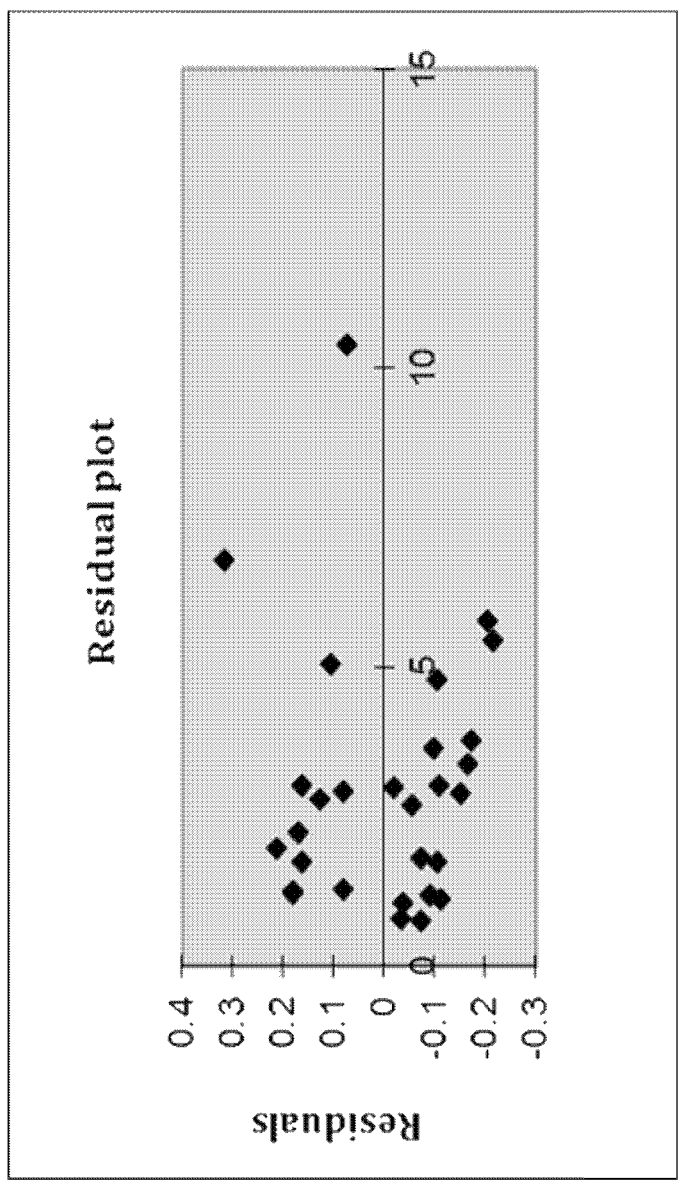
FIG. 20 shows the residuals of the CTTH(x)-OEC(y)-relation. As can be seen, the interrelationship between CTTH and OEC seems to show an approximate hyperbola dependency. Thus, it seems that small decreases in CTTH induces relatively high increases in OEC.

Capillary transit time heterogeneity is an interesting—and perhaps a rather important—feature of the microcirculation, thus potentially being a prerequisite for changing oxygen extraction capacity. In this study, we show that CTTH and OEC approximately follow a hyperbola structure (FIG. 20). Consequently, with these findings, we suggest that a gradual greater reduction of CTTH induces a gradual greater increase in OEC. Additionally, Kalliokoski and co-workers demonstrate that micro vascular transit time heterogeneity and oxygen extraction are weakly linearly correlated, though not graphically shown (Kalliokoski et al., 2004). However, together with our findings these results suggest that oxygen extraction capacity becomes gradually more dependent on the down regulation of capillary transit time heterogeneity as exercise becomes more strenuous (even without capillary recruitment).

Figure 21:
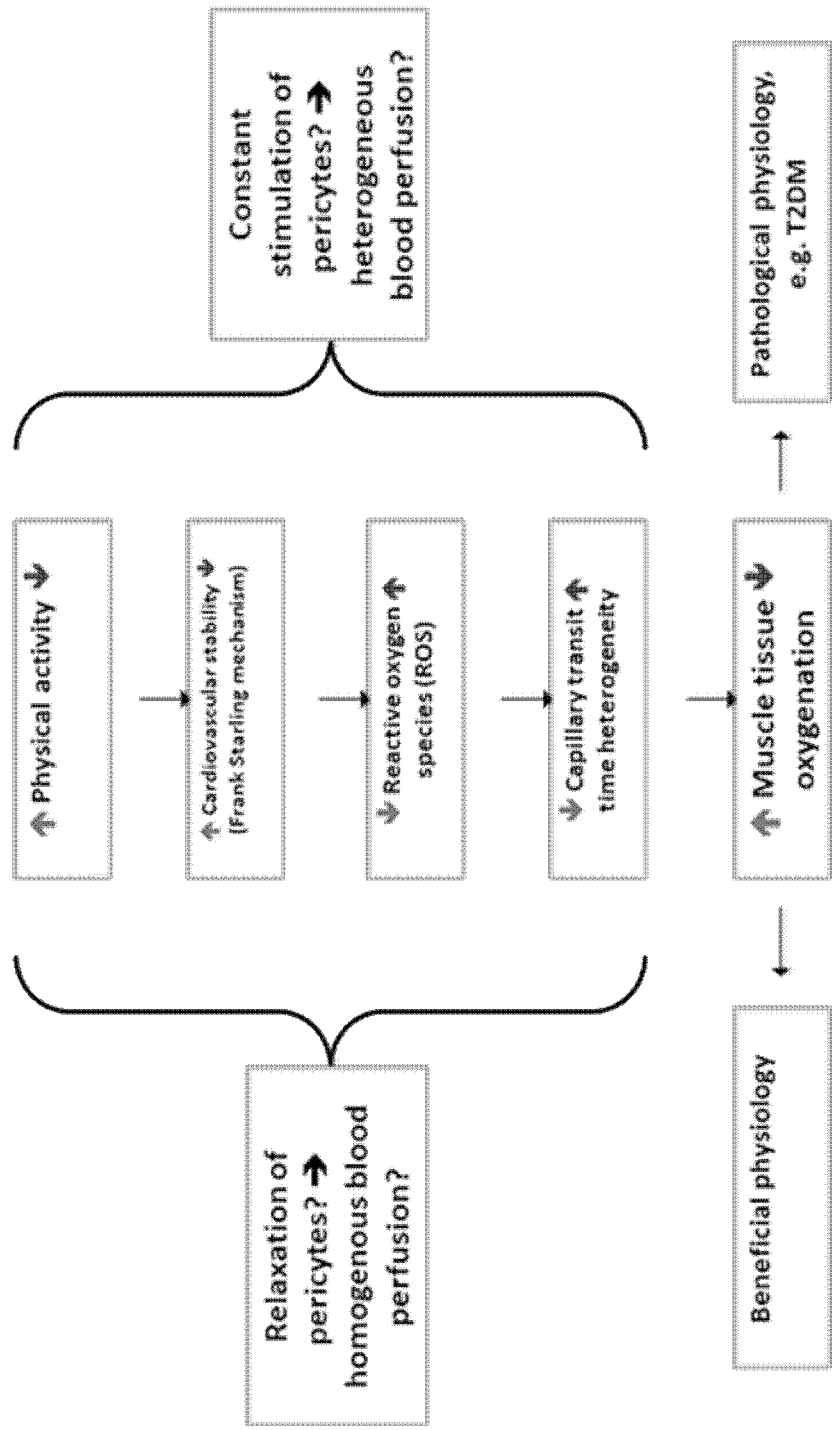
FIG. 21 shows a schematic outline of theoretical relation between cellular metabolic requirements and muscle blood perfusion. Regular physical exercise improves cardiovascular stability through greater utilisation of Frank Starling mechanism. In the long run, this is believed to induce a balanced production of reactive oxygen species (ROS) and antioxidants, possibly reducing the CTTH. Finally, this will improve muscle tissue oxygenation, leading to beneficial hemodynamic-metabolic coupling. The potential ability of pericytes to relax during exercise could possess pivotal effects throughout the entire vascular system by securing optimal oxygenation of organs. On the other hand, lack of regular physical exercise could favor several physiological adaptations, which lead to impaired muscle tissue oxygenation, and, similarly, poor glucose extraction, as observed in diseases such as type-two diabetes (e.g. T2DM)

Several research groups have also demonstrated that dynamic exercise elicits less heterogeneous blood perfusion in exercising muscle (Laaksonen et al., 2003; Kalliokoski et al., 2003a; Kalliokoski et al., 2001). Furthermore, increased capillary flow heterogeneity was demonstrated in a rat model of ischemic stroke (Tomita et al., 2002). Subsequently, these results suggest that CTTH may be a critical phenomenon, which increases muscle tissue oxygenation during graded muscle work and reduces oxygenation in the ischemic state. This active regulation of capillary perfusion patterns has been speculated to arise from the redirection of capillary flows by means of precapillary sphincters and functional thoroughfare or capillary pericytes (Peppiatt et al., 2006; Hirschi & D'Amore, 1996; Hudetz et al., 1996). Though not demonstrated in this study or in muscle capillary in vivo, an English research group has demonstrated that a large fraction of cerebellar pericytes dilate in response to local electrical stimulation (Peppiatt et al., 2006). A German research group recently showed that pericytes control capillary diameter in vivo, whereas arterioles induce hyperemia in their experimental setting (Fernandez-Klett et al., 2010). Even though this contradicts the notion that capillary pericytes induce upstream vasodilatation, it is reasonable to reconsider that the action of pericytes still may take part in a profound metabolic role, as generalised pericyte dilatation would allow more homogeneous flow of red blood cells in response to local release of neurotransmitters (Peppiatt et al., 2006), thus most likely reducing CTTH. Additionally, in the light of the presented results and the studies presented, one may speculate whether improved oxygenation in response to graded muscle work can relax pericytes (see FIG. 21)?

Since pericytes contribute to the regulation of micro vascular circulation (Díaz-Flores et al., 1991), these cells may also have a putative pharmacological function as well. Consider the present knowledge about cardiovascular diseases: whether it is e.g. acute myocardial infarction, heart failure or atherosclerosis (as seen in many patients with T2DM), all diseases show signs of varied dysoxygenation. The existing therapies (e.g. statins, antithrombotic and anti adrenergic drugs) that these patients receive aim to normalise blood flow (reperfusion) or tissue oxygen utilisation (sources), consequently overlooking the potential function of capillaries to control local as well as global tissue oxygenation. Interestingly, new results demonstrate that capillary changes are necessary to release 50-100% of oxygen needs (source). Therefore, dysoxygenation could originate in the blood vessels, rather than from tissue. Importantly, fairly many patients with T2DM gradually develop late complications (approximately 20-70%) despite progress in glucose control. For instance, diabetic retinopathy is associated with loss of retinal capillary pericytes, potentially explaining the occurrence of microaneurysms (Díaz-Flores et al., 1991). Additionally, it has been demonstrated that a higher density of pericytes provides the microvessels with greater resistance to damage by acute hypertension (Díaz-Flores et al., 1991). However, despite its clinical relevance, the effect is currently overlooked by blood flow measurement techniques. Moreover, the potential role of dysoxygenated blood vessels during different vascular diseases could be of highly relevant research, especially for future clinical therapy. This becomes even more interesting/relevant, as cardiovascular diseases account for huge, potentially increasing, economic burdens in total health care. Ultimately, upcoming/future research should focus on whether dysoxygenation could originate in the blood cells, since current therapy seeking to reduce dysoxygenation has not fully been succeeded.

In conclusion, we demonstrate that graded intermittent static handgrip exercise decreases capillary transit time heterogeneity, ultimately increasing oxygen extraction capacity in human skeletal muscle in vivo. Additionally, residual plot analysis suggests that less capillary transit time heterogeneity may improve muscle tissue oxygenation by increasing oxygen extraction capacity during exercise. Even more importantly, can we use CTTH for clinical use, e.g. for diabetic patients with vascular diseases to better understand the role of dysoxygenation? Furthermore, contrast-enhanced ultrasound technique may be a useful method to detect micro vascular changes during exercise.

Study Limitations:

Our model has been used to show that during episodes of high flow, capillary transit time heterogeneity reduces significantly in order to secure muscle tissue oxygenation, ultimately increasing the oxygen extraction capacity. Consequently, it has been demonstrated that muscle tissue oxygenation is critically dependent on capillaries, however by a mechanism that cannot be detected by CEUS. This mechanism, we believe is highly dependent on the activity of pericytes. Additionally, since our purpose simply was to show the close matching between CTTH and OEC during graded handgrip muscle work, this model could be even more sophisticated when supporting it with in vivo measurements of the metabolic changes that occur as human undergoes during exercise, including e.g. glucose uptake, insulin secretion, reactive oxygen and nitrogen species (RONS), c-reactive peptide lactate production and vasodilators. Additionally, specific expression of oxidative proteins (e.g. PGC-1$\alpha$) would most likely also predict and support an even stronger physiological relation between these proteins, blood flow and metabolic substances.

Thus, we will come one step closer to why capillaries are such an integral part of muscle tissue oxygenation and in various diseases, such as type 2 diabetes. Furthermore, provided that this model is gradually extended, we will improve our understanding of the relationships between muscle tissue perfusion and power, contraction strength and oxygen uptake, which can be directly applied for pharmacological purposes in various oxygen-dependent diseases, such as hypoxia and ischemia.

As the purpose of this study was to use CEUS to measure hemodynamic changes, our primary goal was to test its applicability in microcirculation. Naturally, these results of this study may have been more solid if supported by blood samples, including e.g. viscosity, lactate production, c-reactive peptide and plasma glucose. Additionally, the vascular parametric model that was used prevented us in measuring absolute muscle blood volume and muscle blood perfusion, which—if measured—could have supported the observed oxygen extraction capacity as well as a direct measurement of $VO_2$ would have been possible. Additionally, thorough analyses of notified changes in transit time characteristics propose that CTTH is decisive in a view to securing muscle tissue oxygenation during functional hyperemia, consequently claiming its potential relevance in various vascular diseases (e.g. T2DM) and ageing as well.

The Role of Capillary Dysfunction in Alzheimer's Disease

Subjects at risk of Alzheimer's Disease (AD) initially show increased cerebral blood flow and blood oxygen level dependent (BOLD) contrast responses to functional activation. These are followed by decreasing CBF and BOLD response as patients develop progress to mild cognitive impairment (MCI) and AD.

Here we present a hypothesis by which the paradoxical increase in CBF and BOLD responses can be accounted for by the lost ability to homogenize capillary blood flows. This hypothesis is based on recent insights into the relation between the heterogeneity of capillary flows, tissue oxygen tension and oxygen extraction. Our hypothesis proposes that as hyperemia is exhausted as a means of supporting neuronal oxygen needs during activation, tissue hypoxia and maintenance of low CBF becomes the only means of maintaining oxygen supplies We present the evidence for capillary involvement in AD pathophysiology. Finally, we discuss the preventative and therapeutic implications of this hypothesis, and its impact for translational dementia research.
Introduction There is accumulating evidence of a link between cerebral vascular dysfunction and Alzheimer's Disease. This includes evidence of both disruptions of the normal regulation of cerebral blood flow (CBF) in response to varying metabolic needs, neurovascular dysfunction (Girouard and Iadecola, 2006), and disturbances in the integrity of the capillary bed. The latter involve microvascular atrophy, physical disruptions of the capillary wall, and endothelial derived inflammatory and neurotoxic factors (Farkas and Luiten, 2001, Zlokovic, 2011). Changes of this type can be expected to result in hypoperfusion and a reduced supply of oxygen to brain tissue. Notably, capillary disturbances have been observed as antecedents of neurodegenerative changes associated with dementia (Bell et al., 2010). In addition, neurovascular dysfunction is a common feature of hypertension and stroke, both of which are major risk factors for AD (Girouard and Iadecola, 2006). These observations suggest that capillary changes and hypoperfusion are intimately involved in the etiopathogenesis of the disease.

Figure 22:
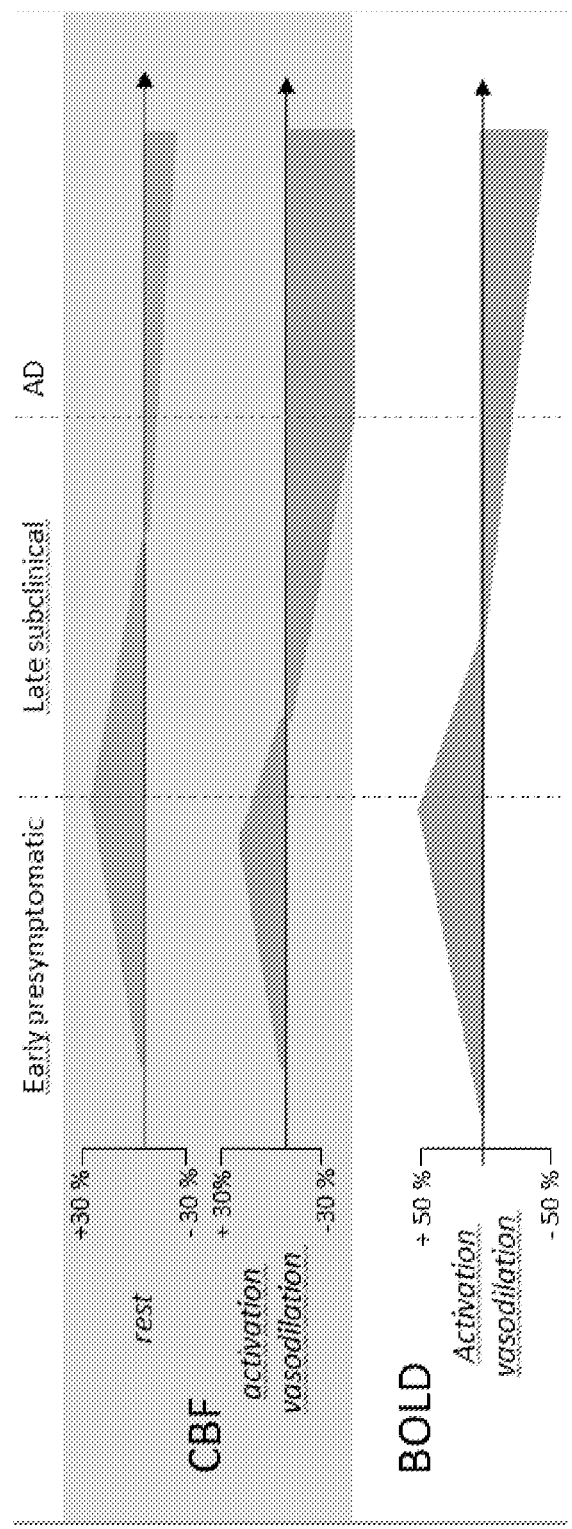
FIG. 22 shows an illustration of the biphasic nature of the CBF and BOLD changes during the course of the disease.

However, it is difficult to reconcile this view with the observation of abnormally high CBF levels in young, asymptomatic carriers of the APOE ε4 AD risk-gene, during both rest (Fleisher et al., 2009a, Scarmeas et al., 2003) and functional activation (Scarmeas et al., 2005). Furthermore, in high-risk subjects, functional MRI reveals elevated blood-oxygen-level-dependent (BOLD) amplitudes in the mediotemporal cortex during memory retrieval tasks. The biphasic nature of the CBF and BOLD changes during the course of the disease are illustrated in FIG. 22. Notably, the initial changes appear decades before the development of symptoms (Bondi et al., 2005, Bookheimer et al., 2000, Braskie et al., 2010, Ringman et al., 2011). This implies that there is either or both an increase in the CBF response and a decrease in oxygen extraction fraction (OEF) during increased metabolic demands. Although APOE ε4 carriers and AD patients develop hypoperfusion prior to the development of symptoms (Ruitenberg et al., 2005, Scarmeas and Stern, 2006), the observation of early hyperperfusion clearly contradict the idea that hypoperfusion is the initial event in the development of AD.

Differences in the way in which CBF is coupled to the metabolic needs during the different phases of the disease can explain this apparent paradox. Here we describe how differences in this coupling can be explained in terms of factors that disturb the pattern of erythrocyte flow through capillary networks. Accordingly, the presymptomatic hyperperfusion and the subsequent hypoperfusion can both be viewed as neurovascular adaptations that maintain tissue oxygenation.

Metabolic Effects of Capillary Flow Patterns

The local availability of diffusible substances, such as oxygen, is traditionally described by the Bohr-Kety-Crone-Renkin (BKCR) equation (Renkin, 1985) in terms of three hemodynamic parameters. Accordingly, the net extraction is limited by (i) regional CBF, (ii) capillary permeability, and (iii) capillary surface area. Under normal conditions, regional CBF is the main factor that determines local oxygen availability. In contrast, capillary permeability is not thought to be a limiting factor, due to the high diffusibility of oxygen molecules across the BBB. With regard to the third factor, there is no evidence in brain tissue of capillary recruitment, that is, the opening of additional capillaries in response to increased metabolic demands (Kuschinsky and Paulson, 1992). Capillary surface area is therefore considered to be constant and proportional to the capillary density under normal circumstances. As a consequence, hypoperfusion and capillary rarefaction would appear to be the only hemodynamic factors in the original BKCR relationship that can lead to decreased oxygen supply, neuronal dysfunction, and neurodegeneration.

Figure 23:
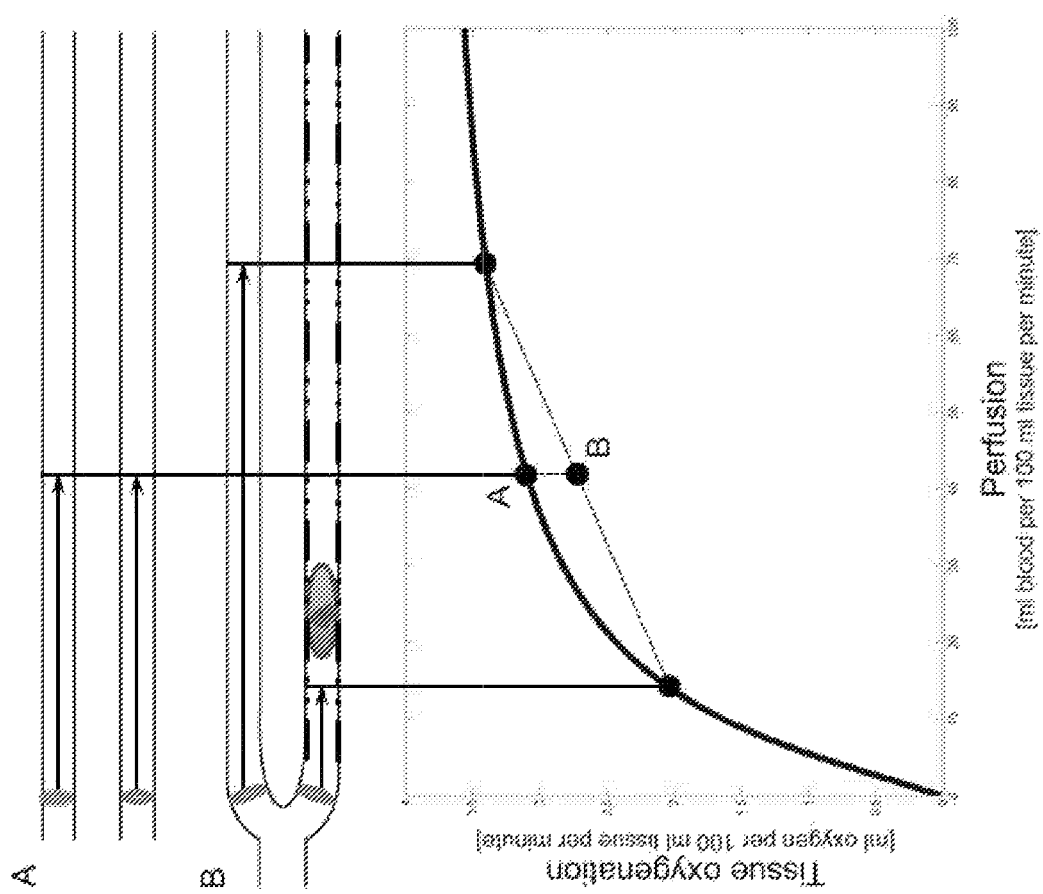
FIG. 23 shows the classical, single capillary flow-diffusion relation for oxygen (Crone, 1963) (bottom curve) shows the maximum amount of oxygen which can diffuse from a single capillary into tissue, for a given CBF. The curve shape predicts crucial properties of 'real' parallel-coupled capillaries (case B) as opposed to 'idealized' single capillaries (case A): Net tissue oxygen availability always decline if capillary flows differ from their mean (the point labeled B is always below the point labeled A, which corresponds to homogenous flows). Also, if erythrocyte flows are hindered along single capillary paths (as indicated by slow-passing immune cells and/or rugged capillary walls) upstream vasodilation amplifies redistribution losses, as erythrocytes are forced through other branches at very high speeds, with negligible net oxygenation gains.

The use of the BKCR equation to describe oxygen extraction in tissue implicitly involves the assumption that the flow of erythrocytes through individual capillaries is uniform. In reality, the flow velocities of erythrocytes through the individual capillaries are not identical (Kleinfeld et al., 1998, Pawlik et al., 1981, Villringer et al., 1994). They are inhomogeneous and influenced by the flow through other capillaries. Capillary flow patterns are complex functions of capillary bed topology, blood viscosity, the adhesion of blood cells to capillary walls, factors that affect the local diameter of individual capillaries (~6-8 µm), and the relative number, deformability, and size of the blood cells (~8-15 µm). FIG. 23 illustrates how the heterogeneity of capillary flows reduces the extraction of oxygen relative to that which would have been predicted from the BKCR paradigm (Østergaard et al., 2000). In view of this observation, we have recently extended the BKCR model to include the effects of capillary transit time heterogeneity (Jespersen and Østergaard, 2012).

According to the extended BKCR model, a reduction in capillary transit time heterogeneity (CTTH) is an integral part of the hemodynamic adaptations to increased metabolic needs. This is supported by the high degrees of CTTH in the resting state (Jespersen and Østergaard, 2012), as calculated from the in vivo recordings of capillary erythrocyte velocities in rats (Kleinfeld et al., 1998, Pawlik et al., 1981, Villringer et al., 1994). In addition, the distribution of erythrocyte velocities in rats, during hypercapnia, hypoxia, and cortical activation (Abounader et al., 1995, Hudetz et al., 1997, Krolo and Hudetz, 2000, Schulte et al., 2003, Stefanovic et al., 2008, Vogel and Kuschinsky, 1996), were shown to be accompanied by reductions in CTTH (Jespersen and Østergaard, 2012). Decreased CTTH (increased transit time homogeneity) acted in concert with increased CBF and changes in tissue oxygen tension to maintain a balance between oxygen availability and metabolic needs (Jespersen and Østergaard, 2012).

The properties of the extended model, with regard to the way in which tissue flow determines tissue oxygenation, differ significantly from those of the classical BKCR equation.

First, in addition to CBF and capillary density, which are the two parameters predicted by the BKCR equation to affect oxygen extraction, CTTH also influences the maximum achievable oxygen extraction fraction (OEFmax) for a given tissue oxygen tension. This is illustrated by the contour plot of OEFmax in FIG. 3.a., where the x-axis corresponds to the mean transit time (MTT) for blood as it passes through the capillary bed. Capillary MTT is defined as the ratio of the capillary CBV to the CBF (Stewart, 1894), that is, by the two central parameters in the original BKCR equation. The y-axis corresponds to the CTTH, here expressed as the standard deviation of the transit times for the individual capillaries. As can be seen in FIG. 23.a. for any MTT, an increase in CTTH results in a reduced OEFmax.

Figure 24:
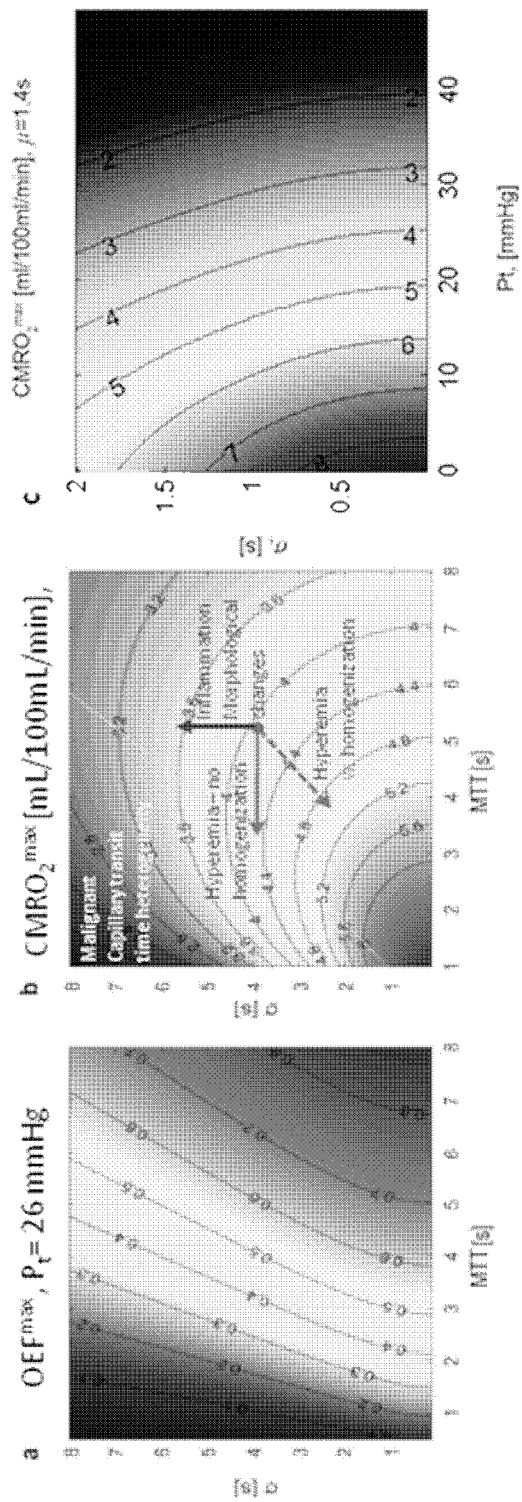
FIG. 24 shows contour plot of OEC (24.a.) for a given mean transit time and capillary flow heterogeneity (σ). The corresponding maximum oxygen delivery is shown in (3.b.) assuming fixed capillary blood volume, CBV=3%. Resting state values assumed are CBF=60 mL/100 mL/min; CaO2=19 mL/100 mL and PtO2=26 mmHg (Ndubuizu and LaManna, 2007). Note that maximum oxygen delivery increases with decreasing flow heterogeneity. The yellow line in 24.b. separates states in which increasing transit times lead to increasing oxygen extraction from states where increasing transit times lead to decreasing oxygen extraction: Malignant capillary transit time heterogeneity (CTTH).

Second, the maximum oxygen consumption that can be supported, CMRO2max, does not necessarily increase with CBF, as predicted by the original BKCR equation. As illustrated in FIG. 24.a., an increase in CBF, during which CTTH remains constant, may paradoxically lead to a hemodynamic state with reduced oxygenation availability. States such as these have been referred to as malignant CTTH (Jespersen and Østergaard, 2012). In FIG. 24.b., they correspond to combinations of CTTH and MTT that lie above the yellow line in FIG. 24.b. Under conditions during which CTTH approaches malignant levels, the extended BKCR equation predicts that the lowering of oxygen tension in the tissue becomes the means by which oxygen availability can be maintained. According to the model, this will be the case provided the CBF is kept low in order to maximize OEFmax. This is illustrated in FIG. 24.c. where CBF is maintained at normal, resting levels. CMRO2max is plotted as a function of tissue oxygen tension (Pt) and CTTH. Note that the typical oxygen requirements for neuronal firing correspond to only a modest reduction in tissue oxygen tension. Therefore, provided CBF remains suppressed, the increased blood-tissue oxygen concentration gradients, which accompany functional activation, facilitate the extraction of oxygen in amounts that are sufficient to support the additional energy requirements of the tissue (Jespersen and Østergaard, 2012). Paradoxically, when the CTTH is irreversibly elevated, the combination of attenuated vasodilator responses and tissue hypoxia will result in energetically favorable states.

Third, the extended BKCR equation predicts that any metabolic benefits of angiogenesis will depend on concomitant changes in CTTH and CBF values. Below the malignant CTTH levels (FIG. 24.b.), increased capillary blood volume must be accompanied by an even greater increase in CBF in order to reduce MTT. Contrary to the predictions of the BKCR equation, angiogenesis will not result in an increase in oxygen availability, unless there is a parallel increase in CBF via normal vasomotor function. Instead, the extended BKCR equation predicts that compensatory angiogenesis in response to tissue hypoxia would tend to reduce the availability of oxygen in tissue when the hypoxia is accompanied by an impaired vasodilatory response, such as observed in AD (Girouard and Iadecola, 2006).

Hypothesis of the relation between microvascular dysfunction and AD etiopathology.

Figure 25:
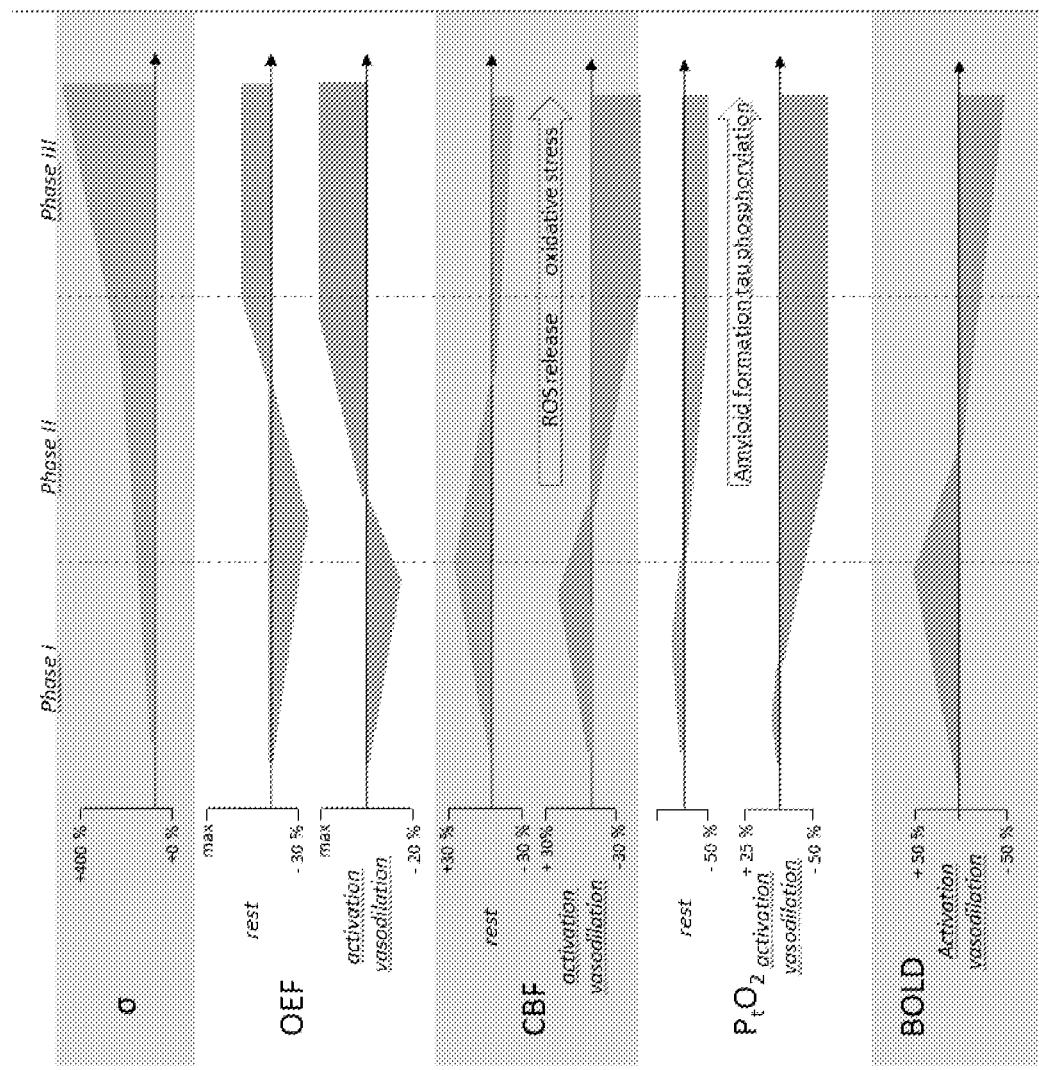
FIG. 25 shows the changes in CBF and tissue oxygen tension which are necessary to maintain tissue oxygenation over time, according to the extended BKCR model.

Here, we operationally define 'capillary dysfunction' as an irreversible increase in CTTH, that is, the hemodynamic correlate of changes in capillaries or in blood that disturb the normal passage of erythrocytes through the capillary bed. Sources of capillary dysfunction and reversible increases in CTTH are discussed further below. The hypothesis presented here, on the basis of the extended BKCR model, assumes that changes in CBF and tissue oxygen tension reflect attempts by the tissue to maintain tissue oxygenation. In FIG. 25, the degree of capillary dysfunction, the CTTH value, increases with time towards the right. The graphs below this display the changes in CBF and tissue oxygen tension which are necessary to maintain tissue oxygenation over time, according to the extended BKCR model. To facilitate the comparison of these curves to the BOLD and CBF changes shown in FIG. 22, the temporal dynamics of OEFmax are shown in the lower graph.

Phase I

During this phase microvascular dysfunction is minimal (CTTH panel) and increases in resting and activity-related CBF levels can still compensate for any decrease in OEFmax. This phase corresponds to the period during which young asymptomatic APOE ε4 carries have increased CBF values during rest (Fleisher et al., 2009a, Scarmeas et al., 2003) and relatively more pronounced CBF increases during functional activation (Scarmeas et al., 2005). In addition, both the enhanced increase in CBF and the reduction in OEF, during functional activation, are predicted to result in an increase in BOLD signals during this phase (Davis et al., 1998) (Davis. These changes in BOLD signals are consistent with the observations made in young asymptomatic APOE-4 carries during memory retrieval tasks (Bondi et al., 2005, Bookheimer et al., 2000, Ringman et al., 2011).

As CTTH and resting CBF continue to increase, the role of vasodilation, as a means of increasing oxygen availability, is eventually exhausted. When this limit is reached, hypoxia ensues and the tissue enters Phase II.

Phase II

During this phase, the CTTH continues to increase, and the extended BKCR model predicts that net oxygen extraction becomes progressively more dependent on the oxygen concentration gradients that result from tissue hypoxia, rather than from increases in CBF. As CTTH continues to increase, the model further predicts that CBF responses will have to be suppressed if an optimal OEFmax is to be maintained. Notably, suppression of the CBF responses, which is a hallmark of neurovascular dysfunction, is observed in humans and in animal models of hypertension and AD (Girouard and Iadecola, 2006). It is now widely accepted that this reduction in CBF responses is associated with an increased production of NADPH derived reactive oxygen species (ROS), which attenuates the normal activity-related vasodilation (Kazama et al., 2003, Kazama et al., 2004, Park et al., 2011).

The increase in the production of ROS could be driven by reductions in tissue oxygen tension. Reductions in tissue oxygen tension are known to activate mechanisms that attempt to either restore oxygenation or help the tissue to adapt to hypoxia (Eltzschig and Carmeliet, 2011). These include the formation of the hypoxia-inducible transcription factors (HIF-1), which are known to be elevated in both AD patients and in animal models of AD (Grammas et al., 2011). HIF-1 induces adaptations in mitochondrial respiration that are beneficial to the tissue, and NF-κβ induced inflammation (Eltzschig and Carmeliet, 2011). Notably, HIF-1 also results in the up-regulation of NADPH oxidase 2 (NOX-2) (Yuan et al., 2011). NOX-2 is involved in electron transport across membranes and in the production of ROS as part of normal brain function (Kishida et al., 2005; Sorce and Krause, 2009). However, high levels of NOX-2 in microglia, astrocytes, neurons, and cerebral vessels are also involved in oxidative cell damage during ageing and in a number of neurological disorders, including AD (Sorce and Krause, 2009). Oxidative cell damage is believed to be an early feature of the AD, in that oxidation of RNA and proteins precedes the deposition of Aβ (Nunomura et al., 2001).

Paradoxically, hypoxia-induced up-regulation of NOX-2 and the subsequent production of ROS can induce changes in arterioles that can benefit tissue oxygenation when CTTH is elevated. ROS attenuates normal vasodilation and, according to the extended BKCR model, helps to maximize oxygen extraction. Increased ROS-production also interferes with the regulation of CBF, in that the walls of small arteries and arterioles become thicker and more rigid as a result of prolonged oxidative damage. In particular, vascular smooth muscle cells degenerate and develop abnormal focal constrictions that result in the narrowing of the vessel lumen. Such permanent reductions in arteriolar diameter would replace the endogenous production of ROS as a means of reducing the CBF responses. As a consequence, progressive arteriolar narrowing would expected to be accompanied by decreases in the production of ROS. This is consistent with the observation that the oxidation of RNA and proteins in tissue decreases, rather than increases, during the course of AD (Nunomura et al., 2001).

The progressive reduction in the CBF responses that occur during Phase II might be expected to result in neurological disturbances. From the perspective of oxygen availability, however, reduced CBF responses represent an adaptation to the increased CTTH. According to the extended BKCR equation, the resulting increase in OEFmax is sufficient to support the typical metabolic requirements of cortical activation in rat brain (Jespersen and Østergaard 2012). This is consistent with recent experimental evidence that pharmacological blockage of the normal CBF response does not interfere with normal neuronal activity Leithner et al 2010; masamoto et al 2009). The extent to which neurovascular dysfunction impairs neurological function during the early stages of AD is uncertain.

As symptoms develop, resting CBF values are typically reduced by 20-30% relative to controls (Farkas and Luiten, 2001). Reductions in tissue oxygen tension, continued oxidative stress and inflammation now initiate the tissue damage that comes to dominate Phase III.

Phase III

Although tissue hypoxia and increased ROS levels are required for optimal oxygen extraction during Phase III, they are also central to the development of key pathological features of AD. First, HIF-1 stimulates the expression of both human and animal β-amyloid precursor protein (APP) cleavage enzyme (BACE1), which leads to an increased production of Aβ (Zhang and Le, 2010). Second, the pathognomonic self-assembly of hyperphosphorylated tau protein into neurofibrillary tangles (NFT) is up-regulated in the presence of both hypoxia and oxidative stress (Zhang and Le, 2010) (Chen et al., 2003). Third, hypoxia impairs the degradation of Aβ, as well as the clearance of Aβ across the blood-brain barrier (BBB), and leads to increased levels of Aβ in the parenchyma (Zhang and Le, 2010, Zlokovic, 2010). The role of hypoxia in AD is supported by the observation that APP23 transgenic mice subjected to hypoxia have increased Aβ1-40 and Aβ1-42 levels, increased plaque number, and exacerbated memory deficits (Sun et al., 2006). High Aβ levels, in turn, has been associated with neuronal dysfunction, neuroinflammation and neuronal loss (Hardy and Selkoe, 2002). There is overwhelming evidence of hypoxia-induced up-regulation of angiogenic factors in AD (Grammas et al., 2011). It is therefore paradoxical that capillary atrophy, rather than angiogenesis, is a dominant feature of AD and AD models (Farkas and Luiten, 2001). The extended BKCR model predicts that, in order for increased capillary volume to be metabolically beneficial, the CBF must also increase in parallel. This is unlikely to occur, however, because, as pointed out above, the blockage of upstream vasodilation invariably results in reductions in the CBF as the disease progresses. The lack of angiogenesis,—and even the capillary rarefaction—observed in AD could therefore in fact be energetically favorable in view of parallel reductions in CBF.

Discussion

The model presented here infers AD etiopathogenesis from the changes in tissue hemodynamics and tissue oxygen tension which must occur in order to maintain oxygen availability as risk-factor related CTTH increases accumulate over time. The extended BKCR model predicts that increased CTTH causes profound dissociations of CBF and oxygen availability (Jespersen and Østergaard, 2012), and that compensatory changes in CBF and tissue oxygen tension to preserve tissue oxygen metabolism would result in neuroimaging findings in qualitative agreement with those found in asymptomatic high risk subjects prior to the diseases, and in MCI/AD. Importantly, the model predicts that neurovascular dysfunction and tissue hypoxia are necessary, but also sufficient means of maintaining tissue oxygenation for normal brain function. Consequently, the oxidative stress, the activation of inflammatory pathways and the amyloid formation commonly observed in AD could partly be viewed as long-term collateral damage, resulting from intrinsic attempts to secure short-term tissue oxygenation in response to capillary dysfunction.

It is a crucial feature of the model that the disease progression is derived entirely from gradual changes in capillaries morphology and function. Regardless of pathoanatomical or pathophysiological origin of capillary changes, their metabolic correlate is determined entirely by CTTH, and disease-related or compensatory changes in arterial and arteriolar tone, described by MTT. Therefore, the model applies more broadly to dementia conditions where microvascular changes occur, such as vascular dementia, and possibly the dementias observed in HIV and HCV, where capillary endothelium is specifically affected by viral infections. In view of this, the model may provide a framework for understanding the overlapping pathological features found in late-onset dementia (Fotuhi et al., 2009). It should be noted, that the duration of the proposed phases I-III may vary according to the local susceptibility of capillaries to specific vascular risk factors and local metabolic activity, giving rise to differences in regional neuronal degeneration, and symptom presentation.

Below, we discuss the evidence of changes in capillary morphology in AD and in common AD risk factors, as well as the correlation of such findings with cognitive deficits in patients and animal models. We then discuss existing evidence of a role of capillary dysfunction in the etiopathogenesis of AD, and the therapeutic implication of this notion.

Changes in Capillary Morphology and Function in AD.

Capillary morphology, and in particular capillary wall structure, are profoundly altered in AD compared to normal ageing (Farkas and Luiten, 2001, Perlmutter and Chui, 1990). Capillaries appear atrophic, fragmented and irregular, with varying diameters. The inner wall, normally formed by specialized endothelial cells with tight junctions, often appear atrophic or swollen, with altered surface properties (Farkas and Luiten, 2001). Endothelial cells are surrounded by capillary pericytes, which are key to the regulation of capillary diameter during functional activation (Fernandez-Klett et al., 2010), to blood brain barrier function (Armulik et al., 2010, Daneman et al., 2010), to angiogenesis (Dore-Duffy and LaManna, 2007), and to the brain's immune system (Thomas, 1999). The fate of pericytes of in AD remain unclear as they have been reported to either undergo atrophy or to appear in a higher proportion in some capillary sections (Farkas and Luiten, 2001). Together, endothelial cells and pericytes produce the capillary basement membrane (CBM) which contains collagen, laminin and proteoglycans, but undergo a number of pathological changes in AD (Perlmutter and Chui, 1990). These involve fibrillary and amyloid deposits between the inner and outer lamina, which protrude into the capillary lumen. FIG. 24 summarizes the morphological changes in capillary wall structure and lumen in humans specimens, and in animal models (Farkas and Luiten, 2001)

The properties of pericytes in environments of elevated amyloid-levels have received special attention. Cultured human pericytes undergo degeneration when exposed to certain subtypes of Aβ (Verbeek et al., 1997). In both spontaneous and hereditary AD, pericytes express Aβ receptors which have been shown to be involved in the internalization of amyloid and subsequent pericyte death (Wilhelmus et al., 2007). Pericytes are believed to come in close contact with amyloid during the normal clearance of soluble amyloid through the perivascular space (Ball et al., 2010, Carare et al., 2008, Weller et al., 2008).

Amyloid-induced pericyte damage could change capillary morphology and function, and thereby, according to the model above, cause neurovascular dysfunction. Interestingly, Aβ amyloid, and in particular the amyloid Aβ1-40 subtype, has been shown to attenuate normal vasodilator responses, owing to concomitant increase in the production of endothelial superoxide and a reduction in the bioavailability of NO (Iadecola et al., 1999, Niwa et al., 2001, Thomas et al., 1996). In support of a hypoxia-related adaptation, ROS were recently shown to be derived from NADPH oxidases (Park et al., 2011).

Both arterioles and capillaries are densely innervated by noradrenergic projections from locus coerulus and acetylcholinergic fibers from basal forebrain (Peppiatt et al., 2006). This innervation seems to facilitate dilation of both arterioles and pericytes during increased metabolic needs in normal brain (Attwell et al., 2010). Scheibel and colleagues found a extensive pericyte degeneration and complete loss of pericapillary nervous plexes in AD (Scheibel et al., 1987). In addition to remote nervous control, capillary diameter is also regulated by a range of local metabolic and neurotransmitter signals (Attwell et al., 2010). Therefore, the metabolic effects of reduced vascular innervation remains poorly understood. For recent comprehensive reviews of the role of pericytes in AD, see (Hamilton et al., 2010, Winkler et al., 2011)

Changes in Capillary Morphology and Function in AD Risk Factors

Cardiovascular Disease have long been known to share the same risk factors (Breteler, 2000). Thickening of the capillary basement membrane is indeed a common feature of cardiovascular risk factors Studies in spontaneously hypertensive, stroke-prone rats show degeneration. The table below show findings in common AD risk factors.

| Risk Factor | Changes in capillary morphology | Reference |
|---|---|---|
| Ageing | Thickening of basement membrane Possibly pericyte loss | (Thomas, 1999) |
| Hypertension | Pericyte degeneration, swelling of endothelium and surrounding astrocyte end-feet (spontaneously hypertensive rats). | (Tagami et al., 1990) |
| Ischemic stroke | Pericyte constrictions (animal models) | (Dalkara et al., 2011, Yemisci et al., 2009) |
| Diabetes | Loss of pericytes and thickening of capillary basement membrane of the cerebral capillaries (animal models) Thickening of basement membrane (humans) | (Junker et al., 1985, McCuskey and McCuskey, 1984) (Johnson et al., 1982) |
| Brain trauma | Dislocation of pericytes, away from capillaries (animal models) | (Dore-Duffy et al., 2000) |

Studies support the link between capillary constrictions and upstream neurovascular dysfunction in AD risk factors. Angiotensin-II, which is involved in the pathogenesis of hypertension, constricts a large proportion of freshly isolated retinal microvessels via activation of pericytic AT1 receptors (Kawamura et al., 2004). Meanwhile, in vivo administration of angiotensin-II attenuates upstream vasodilation during functional hyperemia and result in the release through NADPH oxidase derived radicals (Kazama et al., 2003, Kazama et al., 2004). Cognitive Correlates of microvascular morphology.

In pericyte-deficient mice, Bell and colleagues demonstrated that age-related vascular damage precedes neurodegenerative changes, learning and memory impairment, and neuroinflammatory responses (Bell et al., 2010), supporting the notion that dysfunctional capillaries in themselves may create a phenotype characteristic of dementia.

In humans, several studies show that the formation of neurofibrially tangles (NFT) and the progressive neuronal loss within the entorhinal cortex and the hippocampal CA1 formation correlate with cognitive decline in the course of aging. According to quantitative stereological estimates of the total neuronal loss and NFT density, these 'traditional' histological changes are believed, however, to account for only half of the variability in Clinical Dementia Rating (CDR) scores recorded in brain aging and AD, respectively. Controlling specifically for the number of neurofibrillary tangles and neuron numbers, Bouras and colleagues showed that mean capillary diameters, rather than capillary numbers, in entorhinal cortex and the CA1 hippocampal area, are independent predictors of cognitive status in old individuals with cognitive impairment (Bouras et al., 2006). Regulation of Capillary and Arteriolar Diameter in Capillary Dysfunction The apparent need for suppression of CBF in capillary dysfunction would seem to pose a major challenge to the intrinsic regulation of vascular and capillary diameters. In normal brain, increased neuronal activity is accompanied by the dilation of both arterioles and capillaries (Fernandez-Klett et al., 2010) (Attwell et al., 2010). This is thought to be caused be relaxation of SMC and pericytes in response to factors such as the release of neurotransmitters (Peppiatt et al., 2006), increasing lactate levels and low oxygen tension (Yamanishi et al., 2006), and vascular innervation (Attwell et al., 2010). According to the extended BCKR model, arteriolar and capillary dilation appear synergistic, as they tend to increase CBF while also reducing CTTH to maintain OEFmax.

As CTTH approaches MTT, suppression of CBF responses become critical, while CTTH must be kept as low as possible to maintain high OEFmax. Therefore, the visadilatory action of neurotransmitters and metabolic signals must instead be suppressed at the arteriolar level, while maintained at the capillary level. Endogenous production of ROS and down-regulation of NO at the level of arteriolar endothelium can provide efficient suppression of CBF, but a short distance downstream of the arteriole, contractile pericytes would be expected to react in a similar way to altered levels of vasoactive substances. Pericytes are thus known to constrict in response to ROS production (Yemisci et al., 2009) and to NO depletion (Haefliger et al., 1994, Haefliger and Anderson, 1997). In this way, neurovascular dysfunction may cause constricting of otherwise unaffected capillaries, and thereby increase CTTH. Endogenous suppression of CBF could therefore lead to downstream reductions in OEFmax. Unlike the permanent changes in capillary morphology which lead to capillary dysfunction, such reductions in CTTH could, however, be irreversible, as we will discuss further below.

Modulation of AD Disease Severity by Altered Capillary Flows

The proposed disease mechanism predicts that progression of the disease in closely linked to CTTH and CBF, and in particular, their combined proximity to the state of malignant CTTH, where hypoxia ensues, and CBF is argued to be suppressed by intrinsic production of ROS. Consequently, it would be expected that factors that increase CTTH, or factors which alter CBF would also affect disease severity. In particular, factors which temporarily increase CBF are expected to aggravate neurological symptoms and accelerate disease progression throughout Phase II. Meanwhile, and in contrast to theories proposing hypoperfusion as the primary cause of the disease, hypoperfusion would be expected to reduce oxidative stress and slow the progression of the disease throughout Phase II.

In this section, the evidence of links between AD severity and capillary flow patterns is reviewed. Below, reports of correlations between CBF, symptom severity and disease progression severity are discussed.

White Blood Cell Properties. The ratio of leukocytes to RBCs is only 1:1000 in normal blood. Nevertheless, leucocytes profoundly affects the microcirculation; both due to their diameters, which exceed that of a normal capillary, and due to the stiffness of their cytoplasm. Both factors slow capillary flows due to the deformation required for entrance into, or passage through, the capillaries (Mazzoni and Schmid-Schonbein, 1996). The viscosity of leukocyte cytoplasm is further decreased during systemic inflammation. Combined with the effects of increased cell counts, it is therefore likely that systemic inflammation results in an additional increase in RBC CTTH (See FIG. 22).

The cerebral microcirculation displays inflammatory changes in AD, in a manner similar to that observed as the chronic, low-grade inflammation associated with diabetes, hypertension, obesity, and cardiovascular disease. AD brain endothelial cells express elevated levels of inflammatory adhesion molecules, such as monocyte chemoattractant 1 (MCP-1), intercellular adhesion molecule-1 (ICAM-1) and cationic antimicrobial protein 37 (CAP37). When combined with the deformation and shear stress that occurs in immunoactive cells as they pass at low velocity through capillaries with disrupted inner lumens (See FIG. 22), the blood-brain barrier in AD is likely to be disrupted and brain parenchyma exposed to toxic substances released by activated immune cells that come in to prolonged contact with an activated endothelium. This is supported by evidence that the capillaries of AD patients release significantly higher levels of proinflammatory factors, including NO, thrombin, TNFα, IL-1β, IL-6 and matrix metalloproteinases (MMPs) than age-matched controls, and provides additional evidence that capillary inflammation may contribute to chronic parenchymal inflammation—See overview by Grammas, and references therein (Grammas, 2011).

Systemic inflammation contributes unfavorably to the progression of AD (Holmes et al., 2009). This phenomenon may explain puzzling reports of a higher prevalence of chronic infections in AD cohorts and the striking effects that eradication therapy has on cognitive scores and overall AD patient survival (Kountouras et al., 2009, Kountouras et al., 2010). As white blood cell rheology in mild inflammations such as these are not believed to affect overall perfusion, these findings appear to favor CTTH changes rather than perfusion changes as a key factor in AD.

Conversly During this stage, agents that relax capillary but not arteriolar tone may improve tissue oxygenation without eliciting deleterious hyperemia. Blockage of β2-adrenergic receptors (Zschauer et al., 1996), the AT-1 angiotensin II receptor system (Kawamura et al., 2004, Matsugi et al., 1997), and calcium channels are theoretically capable of inhibiting pericyte constriction and can be expected to improve tissue oxygenation by facilitating more homogenous capillary transit times. Takeda and colleagues have shown that treatment of APP mice with an AT-1 blocker reduced the level of ROS in capillaries to levels similar to those recorded in wild-type mice. At the same time, it partly reversed the upstream neurovascular dysfunction (vasoconstriction) and resulted in improved spatial learning (Takeda et al., 2009). This finding is in agreement with the dilatory effects on capillaries that this AT-1 blocker has in vivo, and is consistent with reports of the beneficial effects of common anti-hypertensives in prevention and delaying the onset of AD (Shah et al., 2009). The beneficial effects are due in part to the prevention of microangiopathy in hypertension and diabetes, and in part to its direct effects on the tone of functioning pericytes. Strategies for reversing NO depletion is discussed in a separate section below.

CBF, AD Severity and AD Progression

Chronic increases in CTTH prevents homogenization of capillary transit times during hyperemia. This occurs not only during neuronal firing, but also during physiological hyperemia which results from increased arterial CO2 level or from hypoxemia. Our model predicts that obstructive sleep apnea, will accelerate neurodegenerative changes in patients with capillary dysfunction, as a result of the hypoxia and oxidative stress that accompanies vasodilatory signaling hypoxia/hypercapnia. which is related to sleep-disorders and a prominent risk factor in the development of dementia (Fotuhi et al., 2009), Pharmacologically Induced CBF Reduction Quantitative PET measurements in patients with early signs of Parkinson's disease, show that that treatment with the NMDA receptor antagonist memantine lowers resting CBF and increases OEF (Borghammer et al., 2008). In agreement with the notion that alleviation of the needs for intrinsic ROS production to reduce CBF would reduce disease progression, memantine has been shown to reduce clinical deterioration in moderate-to-severe Alzheimer's disease (Reisberg et al., 2003).

Inflammation and Cerebral Microcirculation in AD

The Role of NO

Although depletion of arterial NO may be beneficial during vasodilation if CTTH is high, a downstream decrease in capillary NO will result in an increase in the CTTH and a decrease in the oxygen availability. The lack of a constitutive production of NO has also been linked to the progression of AD (de la Torre and Stefano, 2000). Accordingly, the therapeutic administration of NO could be of importance in the treatment of AD.

NO is produced from L-arginine by NO synthases (NOS's) (Knowles et al., 1989). In mammalian tissues NO can also be produced from nitrite (Zweier et al., 1995). The nitrite in humans stems from either NO or dietary nitrate/nitrite (Bryan et al., 2005; van Faassen et al., 2009). Dietary nitrite consequently provides an accessible route for manipulation of the physiological levels of NO and would circumvent the need for pharmacological agents with the same effects.

Nitrite accomplishes this through the production of NO, which directly inhibits the mitochondrial complex I (Shiva et al., 2007). Nitrite also decreases NADPH oxidase activity and superoxide production (Montenegro et al.). Moreover dietary nitrate increases the production of mitochondrial ATP, by specifically reducing the uncoupling of protons across the mitochondrial membrane. This reduction allows the mitochondria to reduce the amount of oxygen needed to produce more ATP (Larsen et al., 2011).

As a source of NO, nitrite could be of importance for the oxygen metabolism in brain tissue on several levels: i)

Nitrite could act to decrease CTTH in response to neuronal activity, in that neuronal activity decreases local pH through the secretion of acid by astrocytes (Chesler, 2003). This would also allow nitrite to play a role at the capillary level in that astrocytic endfeet directly contact capillaries. ii) By reducing oxidative stress and the production of ROS's during hypoxic events, e.g. during neuronal activity in Phase II and III, nitrite could help reduce the amount of vascular and cellular injury in AD. iii) By increasing mitochondrial oxygen efficiency nitrite could expand the window for normal physiological functioning and delay the time at which low pO2 becomes pathophysiological. iv) Nitrite could act to reduce the development of a malignant and irreversible increases in CTTH, by reducing the flow-reducing effects of vascular injury.

One indication that nitrite may ameliorate the progression of AD is that the intrathecal levels of nitrate in AD patients are inversely correlated with the degree of intellectual impairment (Tarkowski et al., 2000). It is also noteworthy that green leafy vegetables is the major dietary source of nitrate and a key part of the Mediterranean diet, which is reported to offer some protection against AD (Scarmeas et al., 2007). In addition, the therapeutic value of green leafy vegetables in hypertensive disorders appears to be related to their nitrate/nitrite content (Gilchrist et al., 2010). Finally, the production of NO and the NO signalling cascade are integral aspects of the physiology of memory processes (Susswein et al., 2004) and the constitutive production of NO is paramount in preventing increases in immune responses (de la Torre and Stefano, 2000).

Diagnostic and Methodological Implications

PET using the glucose analog fluoro-deoxy-glucose (FDG) is widely used in routine diagnostic neuroimaging of patients suspected of having AD (Jagust, 2000). It is generally assumed that tracer uptake is proportional to glucose uptake even though FDG is not metabolized as glucose is. This has critical implications for the interpretation of FDG uptake data, in that both FDG and glucose blood-tissue clearance is limited by CTTH in much the same way as oxygen. Because FDG is not metabolized, it is not possible to compensate as it is for oxygen and glucose, by a higher blood-tissue concentration gradient. The reduction in FDG uptake observed with PET in asymptomatic APOE-4 carriers (Reiman et al., 2004) may therefore be indicative of the high sensitivity of this technique to early increases in CTTH, rather than an indication of reduced glucose metabolism in APOE-4 carriers in young adulthood. The clearance of FDG further depends on the kinetics and density of capillary glucose transporters in AD patients. A thorough analysis of this effect is beyond the scope of this paper.

While FDG is sensitive to both the early hemodynamic and later neurodegenerative aspects of the disease process proposed here, PET combined with radiotracers with high affinity for amyloid and tau can, according to the model proposed here, provide high specificity and sensitivity to AD pathology that develops in both the hypoxic and subsequent degenerative phases (Small et al., 2006).

Figure 26:
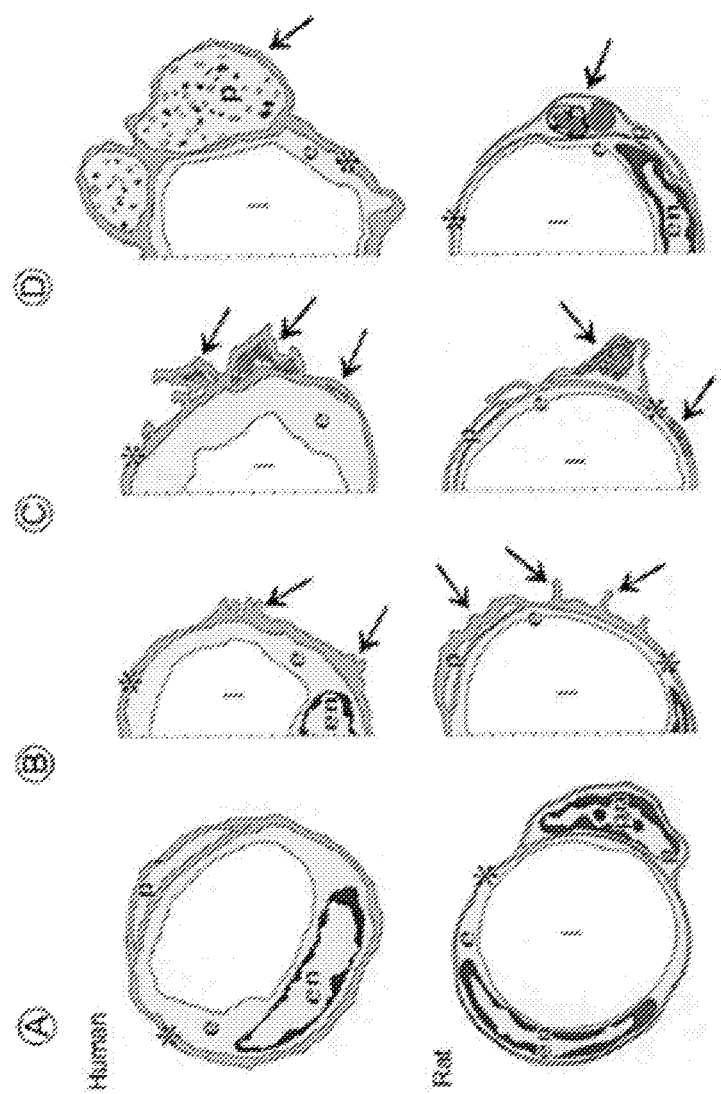
FIG. 26 shows an example of the application of this technique to a patient with AD, and to a somewhat older control-subject.

CTTH can, in theory, be determined from MR, CT, and ultrasound images acquired during the passage of erythrocytes through capillaries in the presence of an intravascular contrast agent (Ostergaard et al., 1999). These techniques have been used to demonstrate disturbed CTTH during acute ischemia (Østergaard et al., 2000). In our own laboratory this approach has recently been used to quantify $\mu$, $\sigma$ and OEFmax (Mouridsen et al., 2011). FIG. 26 shows an example of the application of this technique to a patient with AD, and to a somewhat older control-subject. Magnetic resonance imaging also permits measurement of CBF and BOLD-changes during the performance of standardized memory task. Of note is the measurement of the so-called resting state network activity, which does not depend on subjects ability to cooperate. This can be expected to be a particularly fruitful avenue for further exploration of the evolution of neurovascular dysfunction (Fleisher et al., 2009b)

In animal models, capillary morphology, pericyte tone and RBC flow dynamics can be assessed in vivo with two-photon confocal microscopy (Fernandez-Klett et al., 2010, Stefanovic et al., 2008). Recording $\mu$ and $\sigma$ across ensembles of capillaries can be used to calculate OEFmax and CMRO2max (FIG. 23). Similarly, Laser-Doppler recordings of the mean and standard deviation of RBC velocities permit of $\mu$ and $\alpha$ to conveniently assessed (Jespersen and Østergaard, 2012).

Implications for Translational Research

The proposed roles of capillary morphology and leuco/hemodynamics in the pathophysiology of AD provide a mechanism by which age can become a risk factor in the disease. It also points to the limitations of studying certain aspects of the disease mechanisms in organisms that do not possess a vascular system or that do not display changes in capillary morphology.

Example

Tumor: OEFmax Before and after Anti-Angiogenic Treatment i Glioblastoma

The Extended Bohr-Kety-Crone-Renkin equation (Jespersen & Østergaard 2012) predicts that in order for angiogenesis to improve oxygen availability in tissue, the capillary mean transit time, i.e. the ratio of the capillary blood volume to regional tumor blood flow (rTBF [ml/100 ml/min]), must increase. Therefore, unless rTBF is closely regulated, and is gradually elevated as angiogenesis progresses, the formation of new blood vessels is, parasoxically prone to make the tumor more hypoxic, and therefore more prone to metastasize, to become more malignant, and to respond poorly to therapy.

Conversely, antioangiogenic treatment, in a best case scenario where all tumor vessels destroyed, can only be expected to reverse a tumor to it's original oxygenation—whereas remaining, malignant tumor cells are likely to survive to the extent that they utilize prevailing tissue oxygen. After angiogenic treatment, they may then grow by inducing angiogenesis again.

Figure 27:
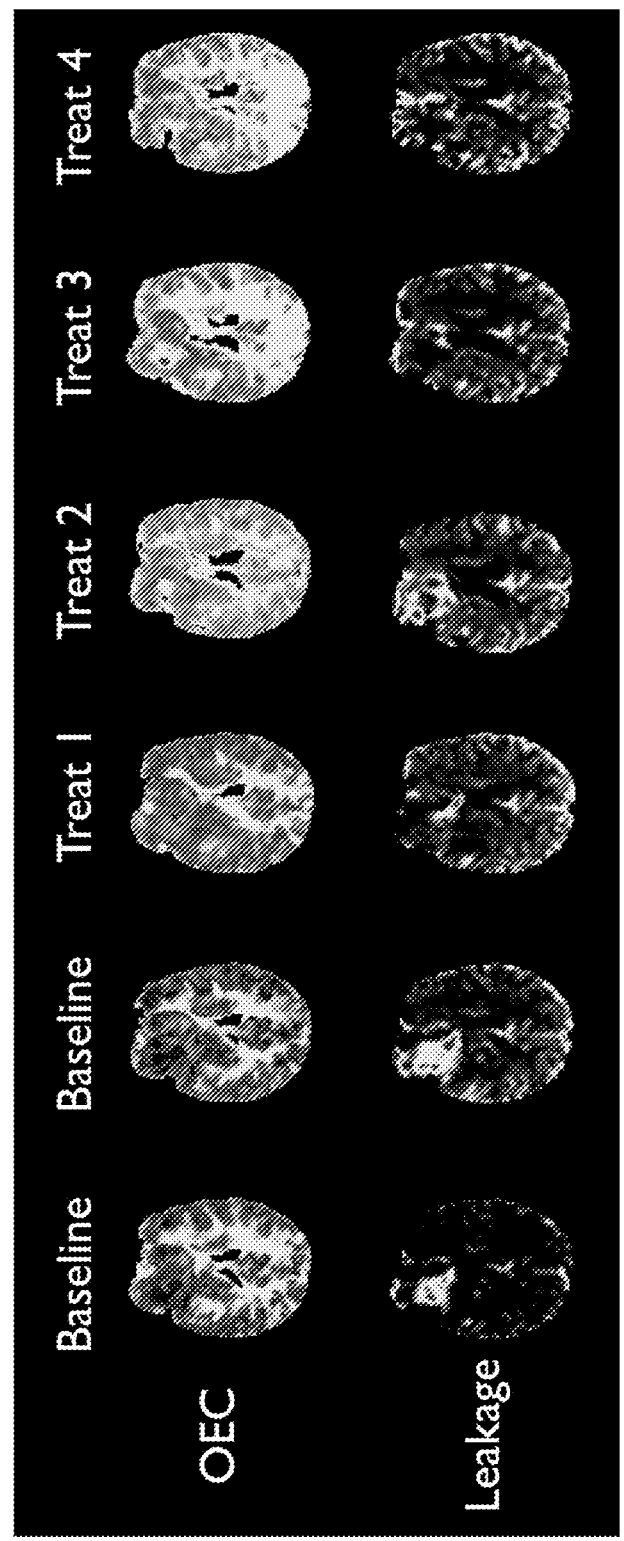
FIG. 27 shows a patient given 4 anti-angiogenic treatment.

FIG. 27 shows a patient given 4 anti-angiogenic treatment. Notice how the initial treatment normalizes maximum oxygen extraction (from being zero, presumeably due to tortuous vessels with high CBV). Antioangiogenic treatment seeming restores tumor oxygenation by pruning this tortuous tumor vasculature. The effect is only temporary, as continued tumor growth seemingly cause hypoxia and stimulates angiogenesis, which is not reversed at subsequent treatments—instead oxygen extraction capacity (OEF or OEFmax) increases. One could envision using such measurements for optimizing individualed treatment—here by giving Adjuvant tumor cell targeted therapy after treatment.

Figure 28:
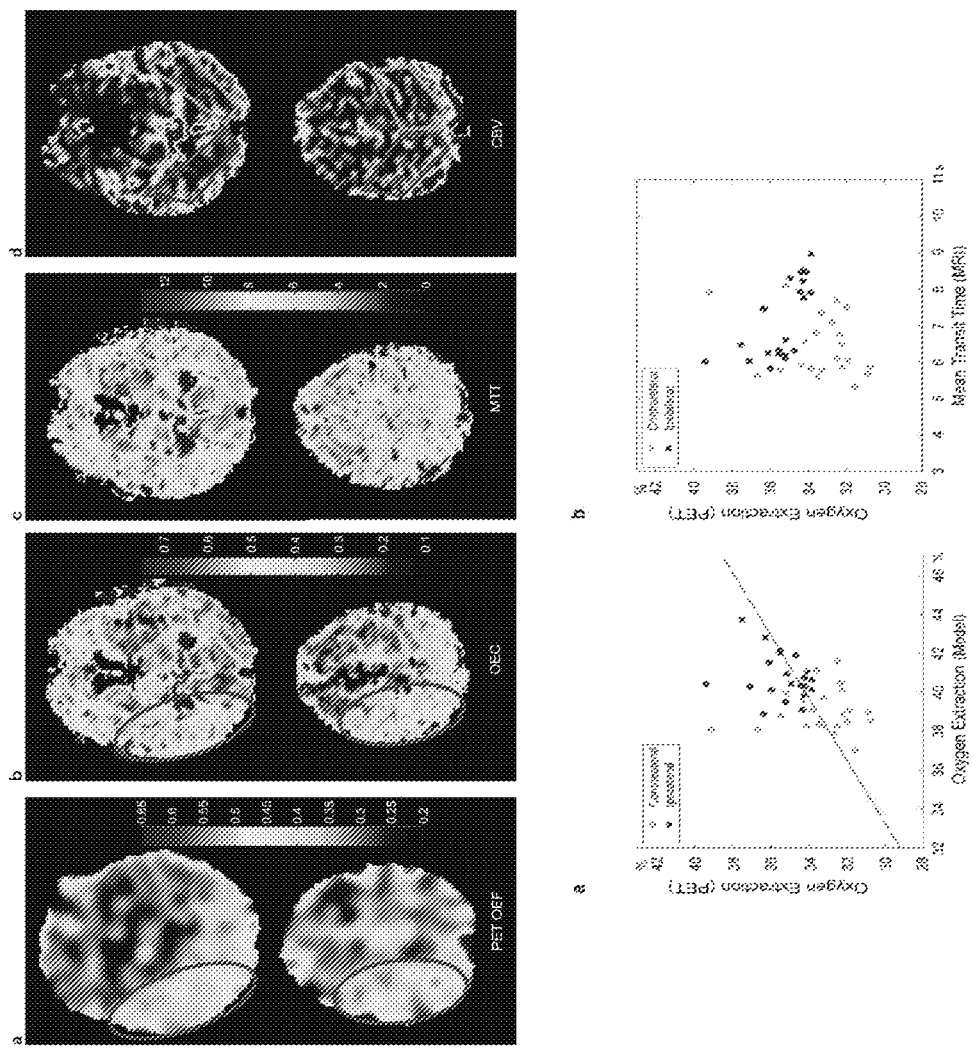
FIG. 28 shows Cerebral blood volume and MTT (the CBV/CBF ratio) measured by dynamic suceptibility contrast (DSC) in a patient with intermittent neurological symptoms due to a unilateral carotid stenosis. The left panel shows the oxygen extraction fraction (OEF) recorded by positron emission tomography (PET) using radiolabelled water and oxygen.

FIG. 28 shows Cerebral blood volume and MTT (the CBV/CBF ratio) measured by dynamic suceptibility contrast (DSC) in a patient with intermittent neurological symptoms due to a unilateral carotid stenosis. The left panel shows the oxygen extraction fraction (OEF) recorded by positron emission tomography (PET) using radiolabelled water and oxygen.

The traditional view would be that the carotid stronosis limits CBF, therefore giving episodes of neurological symptoms. However, neither CBV or MTT are affected, and as one can see in the lower right panel, there is no apparanet relation between MTT and OEF. When measurements by DSC of CTTH are included, however, the model prediction of OEFmax (here called OEC) correlates with the 'true' value—see leftmost panels in upper and lower panel row. This indicates that the microvasculature plays a significant role in determining oxygen availability, and therefore that microvascular disease in the brain (following hypertension etc) could in fact mimics what has hitherto been assumed to be the result of restricted flows through the large vessels.

The therapeutic implications of this notions are significant: Whereas the rational treatment of large vessel limitations of flow is surgery (by-pass), the treatment of microvascular disease is medical (cholesterol lowering, antihypertensives etc). I accordance with this, a study in N Eng Journ Med recently showed that aggressive medical treatment was better than surgery in such patients.

The Functional Hemodynamic of a Kidney in Pig

Introduction

In this study we assessed the functional hemodynamic of a kidney in pig in healthy state and in hemodynamic compromised (by inducing ischemia) state with contrast enhanced ultrasound imaging (CEU). We expect that the Mean-Transit-Time (MTT) is prolonged due to compromised hemodynamic and accordingly an elevation of maximum Oxygen Extraction Fraction (OEFmax) is expected. Due to the ischemic conditions in the kidney, we expect dysfunctional flow regulation and hereby increased Flow-heterogeneity (FH).

Method

A 40 kg pig was used to assess the functional hemodynamic of a kidney. In the first trial, the kidney was evaluated in healthy state (Pre-intervention). In second trial, the main supplying artery (the renal artery) was clamped in 10 minutes and subsequently the kidney was evaluated by CEU (Post-occlusion). In the final trial, the pig underwent a systemic administered of streptococcal bacterium and was evaluated after 45 minutes (Septic shock) by CEU. The ultrasound system settings were the following: framerate: 17 Hz, gain: 100% and compression: 50. The raw data from the scanner was linearized using an unscrambler-software developed by Phillips Healthcare. Subsequently, a temporal low-pass filtration was performed achieving a repetition time (TR) of 1 s. The AIF was manually identified and the perfusion parameters were determined in a region-of-interest (ROI). The perfusion parameters OEFmax, FH and MTT were determined using parametric vascular model.

Results

Figure 29:
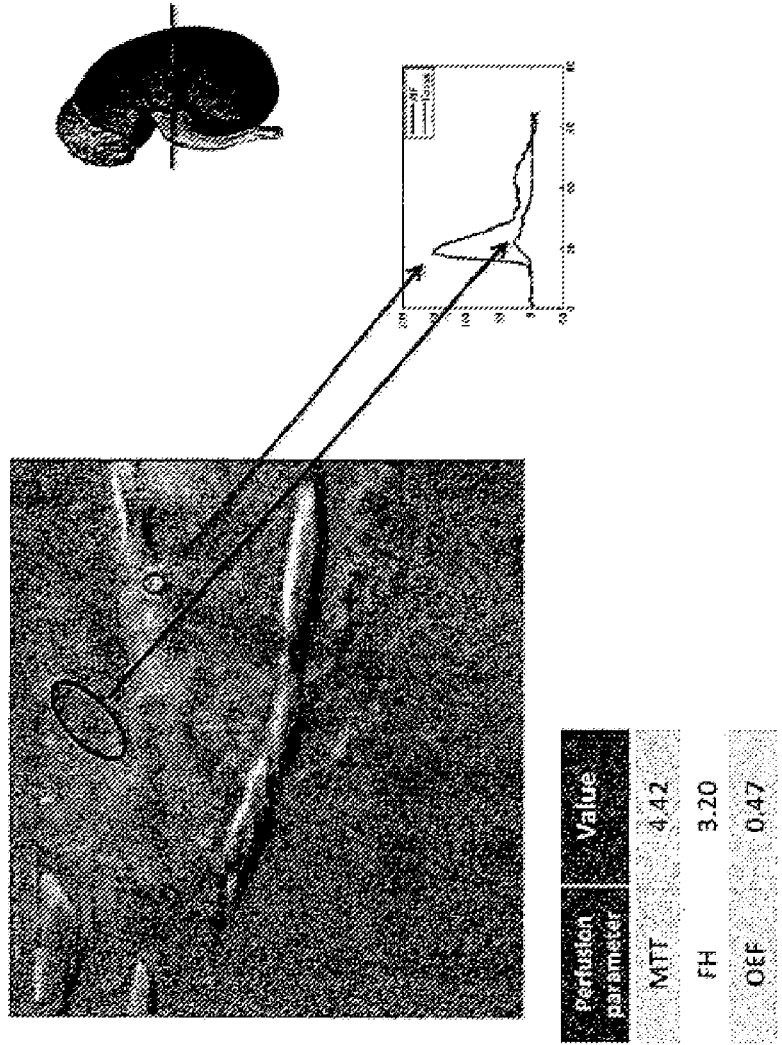
FIG. 29 shows the perfusion values in pre-intervention state. The largest circle indicate the ROI in tissue and the smallest circle indicate the AIF. In the uppet right sub-figure the scan plane is shown.
Figure 30:
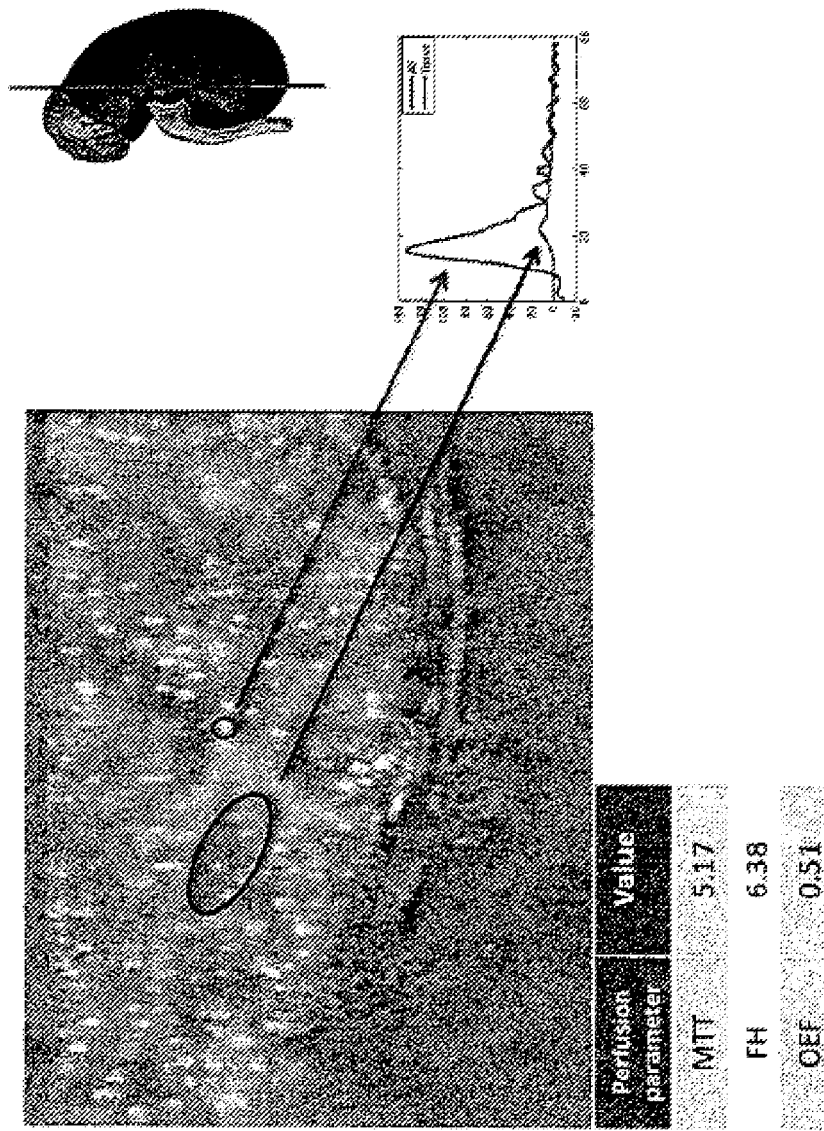
FIG. 30 shows the perfusion values in post-occlusion state. The largest circle indicate the ROI in tissue and the smallest circle indicate the AIF. In the uppet right sub-figure the scan plane is shown.

We found that (FIGS. 29+30), in the intervention states the MU, FH and OEFmax elevated in order the pre-intervention state. At the baseline the perfusion parameters were MTT=4.42 sec, FH=3.20 sec and OEFmax=0.47%. After occlusion the perfusion parameters were increased to MTT=5.17 sec, FH=6.38 sec and OEFmax=0.51% and increased further in the septic shock state MTT=6.31 sec, FH=8.26 sec and OEFmax=0.53%.

Discussion

Figure 31:
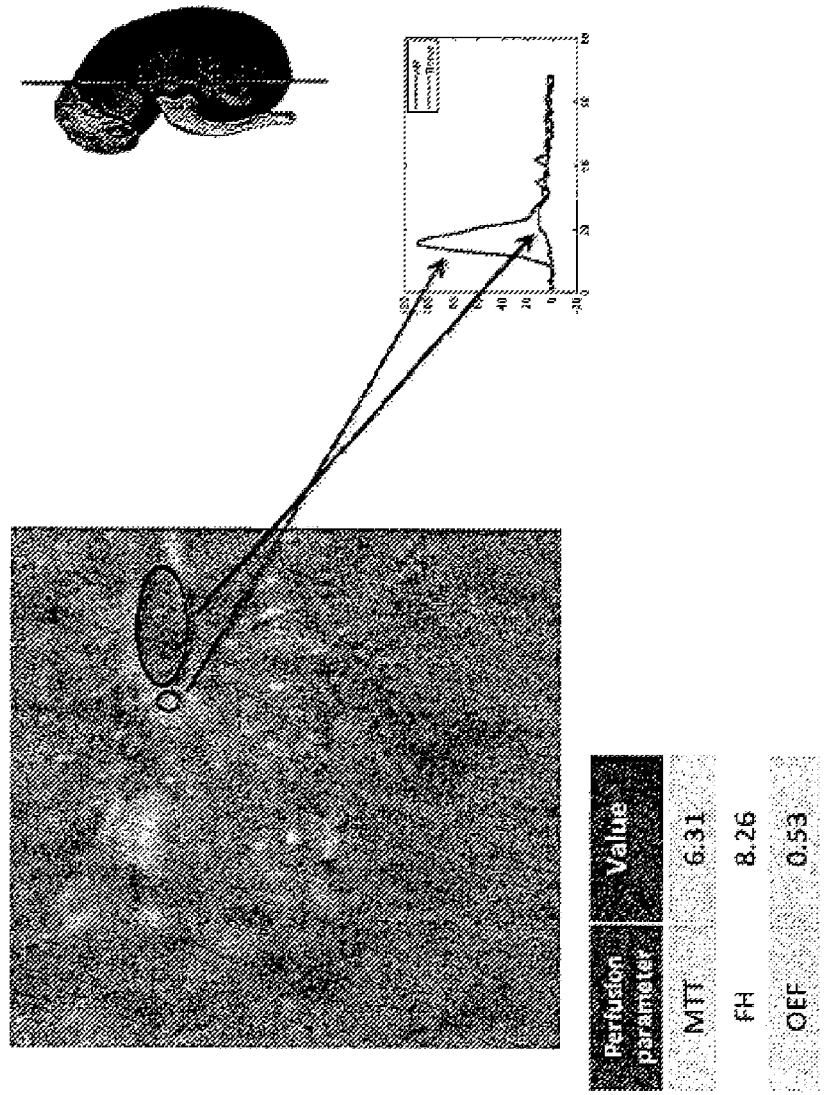
FIG. 31 shows the perfusion values in septic shock state. The blue circle indicate the ROI in tissue and the red circle indicate the AIF. In the uppet right sub-figure the scan plane is shown.

In this study we assessed the functional hemodynamic of a kidney in pig in healthy state and in hemodynamic compromised (by inducing ischemia) state with contrast enhanced ultrasound imaging (CEU). We expected an increase in perfursion parameters MTT, FH and OEFmax and found increament in the post-occlusion state and an further increament in the septic shock state in order to baseline (FIG. 31).

All patent and non-patent references cited in the present application, are hereby incorporated by reference in their entirety.

REFERENCES

Abounader, R., Vogel, J., and Kuschinsky, W. (1995). Patterns of capillary plasma perfusion in brains in conscious rats during normocapnia and hypercapnia. Circ. Res. 76, 120-126.

Akgoren, N., and Lauritzen, M. (1999). Functional recruitment of red blood cells to rat brain microcirculation accompanying increased neuronal activity in cerebellar cortex. Neuroreport 10, 3257-3263.

Arfken, G. B., and Weber, H. J. (2005). Mathematical Methods for Physicists, Sixth Edition: A Comprehensive Guide (Boston: Elsevier Academic Press).

Armulik, A., Genove, G., Mae, M., Nisancioglu, M. H., Wallgard, E., Niaudet, C., He, L., Norlin, J., Lindblom, P., Strittmatter, K., Johansson, B. R., Betsholtz, C., 2010. Pericytes regulate the blood-brain barrier. Nature. 468, 557-561.

Ashkanian, M., Gjedde, A., Mouridsen, K., Vafaee, M., Hansen, K. V., Ostergaard, L., and Andersen, G. (2009). Carbogen inhalation increases oxygen transport to hypoperfused brain tissue in patients with occlusive carotid artery disease: increased oxygen transport to hypoperfused brain. Brain Res. 1304, 90-95.

Attwell, D., Buchan, A. M., Charpak, S., Lauritzen, M., Macvicar, B. A., and Newman, E. A. (2010). Glial and neuronal control of brain blood flow. Nature 468, 232-243.

Ball, K. K., Cruz, N. F., Mrak, R. E., Dienel, G. A., 2010. Trafficking of glucose, lactate, and amyloid-beta from the inferior colliculus through perivascular routes. J. Cereb. Blood Flow Metab. 30, 162-176.

Barakat, R., Cordero, Y., Coteron, J., Luaces, M. & Montejo, R.; Exercise during pregnancy screen at 24-28 weeks: a randomised controlled trial; Br J Sports Med, 2011.

Barretto, R. P., Ko, T. H., Jung, J. C., Wang, T. J., Capps, G., Waters, A. C., Ziv, Y., Attardo, A., Recht, L., and Schnitzer, M. J. (2011). Time-lapse imaging of disease progression in deep brain areas using fluorescence microendoscopy. Nat. Med. 17, 223-228.

Bell, R. D., Winkler, E. A., Sagare, A. P., Singh, I., LaRue, B., Deane, R., and Zlokovic, B. V. (2010). Pericytes control key neurovascular functions and neuronal phenotype in the adult brain and during brain aging. Neuron 68, 409-427.

Bondi, M. W., Houston, W. S., Eyler, L. T., Brown, G. G., 2005. fMRI evidence of compensatory mechanisms in older adults at genetic risk for Alzheimer disease. Neurology. 64, 501-508.

Bonen, A., Dohm, G. L. & van Loon, L. J.; Lipid metabolism, exercise and insulin action; Essays Biochem 42: 47-59, 2006.

Bookheimer, S. Y., Strojwas, M. H., Cohen, M. S., Saunders, A. M., Pericak-Vance, M. A., Mazziotta, J. C., Small, G. W., 2000. Patterns of brain activation in people at risk for Alzheimer's disease. N. Engl. J. Med. 343, 450-456.

Borghammer, P., Vafaee, M., Ostergaard, K., Rodell, A., Bailey, C., Cumming, P., 2008. Effect of memantine on CBF and CMRO2 in patients with early Parkinson's disease. Acta Neurol. Scand. 117, 317-323.

Bouras, C., Kovari, E., Herrmann, F. R., Rivara, C. B., Bailey, T. L., von Gunten, A., H of, P. R., Giannakopoulos, P., 2006. Stereologic analysis of microvascular morphology in the elderly: Alzheimer disease pathology and cognitive status. J. Neuropathol. Exp. Neurol. 65, 235-244.

Boushel, R., Langberg, H., Olesen, J., Nowak, M., Simonsen, L., Bülow, J. & Kjær, M.; Regional blood flow during exercise in humans measured by near-infrared spectroscopy and indocyanine green; J. Appl. Physiol. 89: 1868-1878, 2000.

Braskie, M. N., Medina, L. D., Rodriguez-Agudelo, Y., Geschwind, D. H., Macias-Islas, M. A., Cummings, J. L., Bookheimer, S. Y., Ringman, J. M., 2010. Increased fMRI signal with age in familial Alzheimer's disease mutation carriers. Neurobiol. Aging.

Breteler, M. M., 2000. Vascular risk factors for Alzheimer's disease: an epidemiologic perspective. Neurobiol. Aging. 21, 153-160.

Buxton, R. B. (2010). Interpreting oxygenation-based neuroimaging signals: the importance and the challenge of understanding brain oxygen metabolism. Front. Neuroenergetics 2, 8.

Buxton, R. B., and Frank, L. R. (1997). A model for the coupling between cerebral blood flow and oxygen metabolism during neural stimulation. J. Cereb. Blood Flow Metab. 17, 64-72.

Buxton, R. B., Wong, E. C., and Frank, L. R. (1998). Dynamics of blood flow and oxygenation changes during brain activation: the balloon model. Magn. Reson. Med. 39, 855-864.

Burton, K. S. & Johnson, P. C.; Reactive hyperemia in individual capillaries of skeletal muscle; Am J Physiol 223, 517-524, 1972.

Calbet, J. A. L., Holmberg, H.-C., Rosdahl, H., van Hall, G., Jensen-Urstad, M. & Saltin, B.; Why do arms extract less oxygen than legs during exercise?; Am J Physiol Regul Integr Comp Physiol 289: R1448-R1458, 2005.

Carare, R. O., Bernardes-Silva, M., Newman, T. A., Page, A. M., Nicoll, J. A., Perry, V. H., Weller, R. O., 2008. Solutes, but not cells, drain from the brain parenchyma along basement membranes of capillaries and arteries: significance for cerebral amyloid angiopathy and neuroimmunology. Neuropathol. Appl. Neurobiol. 34, 131-144.

Chaigneau, E., Oheim, M., Audinat, E., and Charpak, S. (2003). Two-photon imaging of capillary blood flow in olfactory bulb glomeruli. Proc. Natl. Acad. Sci. U.S.A. 100, 13081-13086.

Connolly, H. V., Maginniss, L. A. & Schumacker, P. T.; Transit time heterogeneity in canine small intestine: significance for oxygen transport; J. Clin. Invest. 99, 228-238, 1997.

Crone, C. (1963). The Permeability of Capillaries in various Organs as Determined by use of the 'Indicator Diffusion' Method. Acta Physiol. Scand. 58, 292-305.

Dalkara, T., Gursoy-Ozdemir, Y., Yemisci, M., 2011. Brain microvascular pericytes in health and disease. Acta Neuropathol. 122, 1-9.

Daneman, R., Zhou, L., Kebede, A. A., Barres, B. A., 2010. Pericytes are required for blood-brain barrier integrity during embryogenesis. Nature. 468, 562-566.

Davis, T. L., Kwong, K. K., Weisskoff, R. M., and Rosen, B. R. (1998). Calibrated functional MRI: mapping the dynamics of oxidative metabolism. Proc. Natl. Acad. Sci. U.S.A. 95, 1834-1839.

Derdeyn, C. P., Videen, T. O., Yundt, K. D., Fritsch, S. M., Carpenter, D. A., Grubb, R. L., and Powers, W. J. (2002). Variability of cerebral blood volume and oxygen extraction: stages of cerebral haemodynamic impairment revisited. Brain 125, 595-607.

Diaz-Flores, L., Gutierrez, R., Madrid, J. F., Varela, H., Valladares, F., Acosta, E., Martin-Vasallo, P., and Diaz-Flores, L., Jr. (2009). Pericytes. Morphofunction, interactions and pathology in a quiescent and activated mesenchymal cell niche. Histol. Histopathol. 24, 909-969.

Díaz-Flores, L., Gutiérrez, R., Varela, H., Rancel, N. & Valladares, F.; Microvascular pericytes: a review of their morphological and functional characteristics; Histol Histopath (1991) 6: 269-286.

Dor, Y., Brown, J., Martinez, 0.1. and Melton, D. A.; Adult pancreatic β-cells are formed by self-duplication rather than stem-cell differentiation; Nature, 2004; 429: 41-46.

Dore-Duffy, P., LaManna, J. C., 2007. Physiologic angiodynamics in the brain. Antioxid. Redox Signal. 9, 1363-1371.

Dore-Duffy, P., Owen, C., Balabanov, R., Murphy, S., Beaumont, T., Rafols, J. A., 2000. Pericyte migration from the vascular wall in response to traumatic brain injury. Microvasc. Res. 60, 55-69.

Duling, B. R. & Damon, D. H.; An examination of the measurement of flow heterogeneity in striated muscle; Circ Res. 1987; 60(1):1-13.

Ellis, C. G., Bateman, R. M., Sharpe, M. D., Sibbald, W. J. & Gill, R.; Effect of a maldistribution of microvascular blood flow on capillary O2 extraction in sepsis; Am J Physiol Heart Circ Physiol 282: H156-H164, 2002.

Eltzschig, H. K., Carmeliet, P., 2011. Hypoxia and inflammation. N. Engl. J. Med. 364, 656-665.

Erikson, E. & Myrhage, R.; Microvascular dimensions and blood flow in skeletal muscle; Acta Physiol Scand 86, 211-222, 1972.

Farkas, E., Luiten, P. G., 2001. Cerebral microvascular pathology in aging and Alzheimer's disease. Prog. Neurobiol. 64, 575-611.

Fernandez-Klett, F., Offenhauser, N., Dirnagl, U., Priller, J., and Lindauer, U. (2010). Pericytes in capillaries are contractile in vivo, but arterioles mediate functional hyperemia in the mouse brain. Proc. Natl. Acad. Sci. U.S.A.

Fleisher, A. S., Podraza, K. M., Bangen, K. J., Taylor, C., Sherzai, A., Sidhar, K., Liu, T. T., Dale, A. M., Buxton, R. B., 2009a. Cerebral perfusion and oxygenation differences in Alzheimer's disease risk. Neurobiol. Aging. 30, 1737-1748.

Fleisher, A. S., Sherzai, A., Taylor, C., Langbaum, J. B., Chen, K., Buxton, R. B., 2009b. Resting-state BOLD networks versus task-associated functional MRI for distinguishing Alzheimer's disease risk groups. Neuroimage. 47, 1678-1690.

Fotuhi, M., Hachinski, V., Whitehouse, P. J., 2009. Changing perspectives regarding late-life dementia. Nat. Rev. Neurol. 5, 649-658.

Fox, P. T., and Raichle, M. E. (1986). Focal physiological uncoupling of cerebral blood flow and oxidative metabolism during somatosensory stimulation in human subjects. Proc. Natl. Acad. Sci. U.S.A. 83, 1140-1144.

Frank, L. R., Wong, E. C., Haseler, L. J. & Buxton, R. B.; Dynamic imaging of perfusion in human skeletal muscle during exercise with arterial spin labeling; Magn. Reson. Med. 42, 258-267, 1999.

Fujii, N., Jessen, N. & Goodyear, L. J.; AMP-activated protein kinase and the regulation of glucose transport. Am J Physiol Endocrinol Metab 291: E867-E877, 2006.

Georgia, S. & Bhushan, A.; β cell replication is the primary mechanism for maintaining postnatal β cell mass; J Clin Invest. 2004; 114: 963-968.

Girouard, H., Iadecola, C., 2006. Neurovascular coupling in the normal brain and in hypertension, stroke, and Alzheimer disease. J. Appl. Physiol. 100, 328-335.

Grammas, P., 2011. Neurovascular dysfunction, inflammation and endothelial activation: implications for the pathogenesis of Alzheimer's disease. J. Neuroinflammation. 8, 26.

Grammas, P., Tripathy, D., Sanchez, A., Yin, X., Luo, J., 2011. Brain microvasculature and hypoxia-related proteins in Alzheimer's disease. Int. J. Clin. Exp. Pathol. 4, 616-627.

Grubb, R. L., Jr, Raichle, M. E., Eichling, J. O., and Ter-Pogossian, M. M. (1974). The effects of changes in PaCO2 on cerebral blood volume, blood flow, and vascular mean transit time. Stroke 5, 630-639.

Haefliger, I. O., Anderson, D. R., 1997. Oxygen modulation of guanylate cyclase-mediated retinal pericyte relaxations with 3-morpholino-sydnonimine and atrial natriuretic peptide. Invest. Ophthalmol. Vis. Sci. 38, 1563-1568.

Haefliger, I. O., Zschauer, A., Anderson, D. R., 1994. Relaxation of retinal pericyte contractile tone through the nitric oxide-cyclic guanosine monophosphate pathway. Invest. Ophthalmol. Vis. Sci. 35, 991-997.

Hamilton, N. B., Attwell, D., and Hall, C. N. (2010). Pericyte-mediated regulation of capillary diameter: a component of neurovascular coupling in health and disease. Frontiers in Neuroenergetics 2, 1-15.

Hardy, J., Selkoe, D. J., 2002. The amyloid hypothesis of Alzheimer's disease: progress and problems on the road to therapeutics. Science. 297, 353-356.

Hayashi, T., Watabe, H., Kudomi, N., Kim, K. M., Enmi, J., Hayashida, K., and Iida, H. (2003). A theoretical model of oxygen delivery and metabolism for physiologic interpretation of quantitative cerebral blood flow and metabolic rate of oxygen. J. Cereb. Blood Flow Metab. 23, 1314-1323.

Heinonen, I., Saltin, B., Kemppainen, J., Hannu, T. S., Oikonen, V., Nuutila, P., Knuuti, J., Kalliokoski, K. & Hellsten, Y.; Skeletal muscle blood flow and oxygen uptake at rest and during exercise in humans: a pet study with nitric oxide and cyclooxygenase inhibition; Am J Physiol Heart Circ Physiol 300: H1510-H1517, 2011.

Hertz, M. M., and Paulson, O. B. (1980). Heterogeneity of cerebral capillary flow in man and its consequences for estimation of blood-brain barrier permeability. J. Clin. Invest. 65, 1145-1151.

Hirschi, K. K. & D'Amore, P. A.; Review—Pericytes in the microvasculature; Cardiovascular Research 32 (1996) 687-698.

Holmes, C., Cunningham, C., Zotova, E., Culliford, D., Perry, V. H., 2011. Proinflammatory cytokines, sickness behavior, and Alzheimer disease. Neurology. 77, 212-218.

Holmes, C., Cunningham, C., Zotova, E., Woolford, J., Dean, C., Kerr, S., Culliford, D., Perry, V. H., 2009. Systemic inflammation and disease progression in Alzheimer disease. Neurology. 73, 768-774.

Honig, C. R. & Odoroff, C. L.; Calculated dispersion of capillary transit times: significance for oxygen exchange; Am. J. Physiol. 240 (Heart Circ. Physiol. 9): H199-H208, 1981.

Hudetz, A. G., Biswal, B. B., Feher, G., Kampine, J. P., 1997. Effects of hypoxia and hypercapnia on capillary flow velocity in the rat cerebral cortex. Microvasc. Res. 54, 35-42.

Hudlicka, O., Zweifach, B. W. & Tyler, K. R.; Capillary recruitment and flow velocity in skeletal muscle after contractions; Microvascular Research 23: 201-213, 1982.

Humer, M. F., Phang, P. T., Friesen, B. P., Allard, M. F., Goddard, C. M. & Walley, K. R.; Heterogeneity of gut capillary transit times and impaired gut oxygen extraction in endotomexic pigs; J Appl Physiol. 81(2): 895-904, 1996.

Hudetz, A. G., Feher, G., and Kampine, J. P. (1996). Heterogeneous autoregulation of cerebrocortical capillary flow: evidence for functional thoroughfare channels? Microvasc. Res. 51, 131-136.

Hudetz, A. G., Feher, G., Weigle, C. G., Knuese, D. E., and Kampine, J. P. (1995). Video microscopy of cerebrocortical capillary flow: response to hypotension and intracranial hypertension. Am. J. Physiol. 268, H2202-10.

Hyder, F., Chase, J. R., Behar, K. L., Mason, G. F., Siddeek, M., Rothman, D. L., and Shulman, R. G. (1996). Increased tricarboxylic acid cycle flux in rat brain during forepaw stimulation detected with 1H[13C]NMR. Proc. Natl. Acad. Sci. U.S.A. 93, 7612-7617.

Hyder, F., Shulman, R. G., and Rothman, D. L. (1998). A model for the regulation of cerebral oxygen delivery. J. Appl. Physiol. 85, 554-564.

Iadecola, C., Zhang, F., Niwa, K., Eckman, C., Turner, S. K., Fischer, E., Younkin, S., Borchelt, D. R., Hsiao, K. K., Carlson, G. A., 1999. SOD1 rescues cerebral endothelial dysfunction in mice overexpressing amyloid precursor protein. Nat. Neurosci. 2, 157-161.

Jagust, W. J., 2000. Neuroimaging in dementia. Neurol. Clin. 18, 885-902.

Jespersen, S. N., Østergaard, L., 2012. The Roles of Cerebral Blood Flow, Capillary Transit Time Heterogeneity and Oxygen Tension in Brain Oxygenation and Metabolism. J. Cereb. Blood Flow Metab. 32, 264-277.

Jespersen, S. N. & Østergaard, L.; The roles of cerebral blood flow, capillary transit time heterogeneity and oxygen tension in brain oxygenation and metabolism; J. Cereb. Blood Flow and Metab.: 1-14, 2011.

Jessen, N. & Goodyear, L. J.; Contraction signaling to glucose transport in skeletal muscle; J Appl Physiol 99: 330-337, 2005.

Johnson, P. C., Brendel, K., Meezan, E., 1982. Thickened cerebral cortical capillary basement membranes in diabetics. Arch. Pathol. Lab. Med. 106, 214-217.

Junker, U., Jaggi, C., Bestetti, G., Rossi, G. L., 1985. Basement membrane of hypothalamus and cortex capillaries from normotensive and spontaneously hypertensive rats with streptozotocin-induced diabetes. Acta Neuropathol. 65, 202-208.

Kawamura, H., Kobayashi, M., Li, Q., Yamanishi, S., Katsumura, K., Minami, M., Wu, D. M., Puro, D. G., 2004. Effects of angiotensin II on the pericyte-containing microvasculature of the rat retina. J. Physiol. 561, 671-683.

Kazama, K., Anrather, J., Zhou, P., Girouard, H., Frys, K., Milner, T. A., Iadecola, C., 2004. Angiotensin II impairs neurovascular coupling in neocortex through NADPH oxidase-derived radicals. Circ. Res. 95, 1019-1026.

Kalliokoski, K. K., Knuuti, J. & Nuutila, P.; Blood transit time heterogeneity is associated to oxygen extraction in exercising human skeletal muscle; Microvascular Research 67 (2004) 125-132.

Kalliokoski, K. K., Laaksonen, M. S., Knuuti, J. & Nuutila, P.; Perfusion Distribution Between and Within Muscles During Intermittent Static Exercise in Endurance-Trained and Untrained Men; Int J Sports Med 2003a.

Kalliokoski, K. K., Laaksonen, M. S., Takala, T. O., Knuuti, J. & Nuutila, P.; Muscle oxygen extraction and perfusion heterogeneity during continuous and intermittent static exercise; J Appl Physiol 94:953-958, 2003b.

Kalliokoski, K. K., Oikonen, V., Takala, T. O., Sipilä, H., Knuuti, J. & Nuutila, P.; Enhanced oxygen extraction and reduced flow heterogeneity in exercising muscle in endurance-trained men; Am J Physiol Endocrinol Metab 280: E1015-E1021, 2001.

Kayar, S. R., Hoppeler, H., Jones, J. H., Longworth, K., Armstrong, R. B., Laughlin, M. H., Lindstedt, S. L., Bicudo, J. E. P. W., Groebe, K., Taylor, C. R. & Weibel, E. R.; Capillary blood transit time in muscle in relation to body size and aerobic capacity; J. exp. Biol. 194, 69-81 (1994).

Kazama, K., Wang, G., Frys, K., Anrather, J., Iadecola, C., 2003. Angiotensin II attenuates functional hyperemia in the mouse somatosensory cortex. Am. J. Physiol. Heart Circ. Physiol. 285, H1890-9.

Kishida, K. T., Pao, M., Holland, S. M., Klann, E., 2005. NADPH oxidase is required for NMDA receptor-dependent activation of ERK in hippocampal area CA1. J. Neurochem. 94, 299-306.

Kindig, C. A., Richardson, T. E. & Poole, D. C.; Skeletal muscle capillary hemodynamics from rest to contractions: implications for oxygen transfer; J. Appl. Physiol. 92: 2513-2520, 2002.

Kleinfeld, D., Mitra, P. P., Helmchen, F., and Denk, W. (1998). Fluctuations and stimulus-induced changes in blood flow observed in individual capillaries in layers 2 through 4 of rat neocortex. Proc. Natl. Acad. Sci. U.S.A. 95, 15741-15746.

Knudsen, G. M., Pettigrew, K. D., Paulson, O. B., Hertz, M. M., and Patlak, C. S. (1990). Kinetic analysis of blood-brain barrier transport of D-glucose in man: quantitative evaluation in the presence of tracer backflux and capillary heterogeneity. Microvasc. Res. 39, 28-49.

Kountouras, J., Boziki, M., Gavalas, E., Zavos, C., Deretzi, G., Chatzigeorgiou, S., Katsinelos, P., Grigoriadis, N., Giartza-Taxidou, E., Venizelos, I., 2010. Five-year survival after *Helicobacter pylori* eradication in Alzheimer disease patients. Cogn. Behav. Neurol. 23, 199-204.

Kountouras, J., Boziki, M., Gavalas, E., Zavos, C., Grigoriadis, N., Deretzi, G., Tzilves, D., Katsinelos, P., Tsolaki, M., Chatzopoulos, D., Venizelos, I., 2009. Eradication of *Helicobacter pylori* may be beneficial in the management of Alzheimer's disease. J. Neurol. 256, 758-767.

Krix, M., Krakowski-Roosen, H., Kauczor, H.-U., Delorme, S. & Weber, M.-A.; Real-time contrast-enhanced ultrasound for the assessment of perfusion dynamics in skeletal muscle; Ultrasound in Med. & Biol., Vol. 35, No. 10, pp. 1587-1595, 2009.

Krix, M., Weber, M.-A., Krakowski-Roosen, H., Huttner, H. B., Delorme, S., Kauczor, H.-U. & Hildebrandt, W.; Assessment of skeletal muscle perfusion using contrast-enhanced ultrasonography; J Ultrasound Med 2005; 24: 431-441.

Krogh, A. (1919). The supply of oxygen to the tissues and the regulation of the capillary circulation. J. Physiol. (London) 52, 457-474.

Krolo, I., and Hudetz, A. G. (2000). Hypoxemia alters erythrocyte perfusion pattern in the cerebral capillary network. Microvasc. Res. 59, 72-79.

Kuschinsky, W., and Paulson, O. B. (1992). Capillary circulation in the brain. Cerebrovasc. Brain Metab. Rev. 4, 261-286.

Kuikka, J. T., Kettunen, R., Tikanoja, T. & Lansimies, E.; Transit time heterogeneity of bolus flow through the heart and lungs in patients with left-to-right intracardiac shunt; Physiol. Meas. 20 (1999), 207-214.

Lassen, N. A. (1966). The luxury-perfusion syndrome and its possible relation to acute metabolic acidosis localised within the brain. Lancet 2, 1113-1115.

Laaksonen, M. S., Björklund, G., Heinonen, I., Kemppainen, J., Knuuti, J., Kyröläinen, H. & Kalliokoski, K. K.; Perfusion heterogeneity does not explain excess muscle oxygen uptake during variable intensity exercise; Clin Physiol Funct Imaging (2010) 30, pp. 241-249.

Laaksonen, M. S., Kalliokoski, K. K., Kyröläinen, H., Kemppainen, J., Teras, M., Sipilä, H., Nuutila, P. & Knuuti, J.; Skeletal muscle blood flow and flow heterogeneity during dynamic and isometric exercise in humans; Am J Physiol Heart Circ Physiol 284: H979-H986, 2003.

Lampaskis, M. & Averkiou, M.; Investigation of the relationship of nonlinear backscattered ultrasound intensity with microbubble concentration at low MI; Ultrasound in Med. & Biol., Vol. 36, No. 2, pp. 306-312, 2010.

Leithner, C., Royl, G., Offenhauser, N., Fuchtemeier, M., Kohl-Bareis, M., Villringer, A., Dirnagl, U., Lindauer, U., 2010. Pharmacological uncoupling of activation induced increases in CBF and CMRO2. J. Cereb. Blood Flow Metab. 30, 311-322.

Malonek, D., Dirnagl, U., Lindauer, U., Yamada, K., Kanno, I., and Grinvald, A. (1997). Vascular imprints of neuronal activity: relationships between the dynamics of cortical blood flow, oxygenation, and volume changes following sensory stimulation. Proc. Natl. Acad. Sci. U.S.A. 94, 14826-14831.

Masamoto, K., Vazquez, A., Wang, P., Kim, S. G., 2009. Brain tissue oxygen consumption and supply induced by neural activation: determined under suppressed hemodynamic response conditions in the anesthetized rat cerebral cortex. Adv. Exp. Med. Biol. 645, 287-292.

Matsugi, T., Chen, Q., Anderson, D. R., 1997. Suppression of CO2-induced relaxation of bovine retinal pericytes by angiotensin II. Invest. Ophthalmol. Vis. Sci. 38, 652-657.

Mazzoni, M. C., Schmid-Schonbein, G. W., 1996. Mechanisms and consequences of cell activation in the microcirculation. Cardiovasc. Res. 32, 709-719.

McCuskey, P. A., McCuskey, R. S., 1984. In vivo and electron microscopic study of the development of cerebral diabetic microangiography. Microcirc. Endothelium Lymphatics. 1, 221-244.

Melzer, K., Schutz, Y., Boulvain, M. & Kayser, B.; Physical activity and pregnancy: Cardiovascular adaptations, Recommendations and pregnancy outcomes; Sports Med 2010: 40 (6): 493-507.

Mintun, M. A., Lundstrom, B. N., Snyder, A. Z., Vlassenko, A. G., Shulman, G. L., and Raichle, M. E. (2001). Blood flow and oxygen delivery to human brain during functional activity: theoretical modeling and experimental data. Proc. Natl. Acad. Sci. U.S.A. 98, 6859-6864.

Mouridsen, K., Christensen, S., Gyldensted, L., and Ostergaard, L. (2006a). Automatic selection of arterial input function using cluster analysis. Magn. Reson. Med. 55, 524-531.

Mouridsen, K., Friston, K., Hjort, N., Gyldensted, L., Ostergaard, L., and Kiebel, S. (2006b). Bayesian estimation of cerebral perfusion using a physiological model of microvasculature. Neuroimage 33, 570-579.

Mouridsen, K., Østergaard, L., Christensen, S., Jespersen, S. N., 2011. Reliable Estimation of Capillary Transit Time Distributions at Voxel-Level using DSC-MRI. Proceedings of the International Society for Magnetic Resonance in Medicines 19th Annual Meeting and Exhibition, 3915.

Niwa, K., Porter, V. A., Kazama, K., Cornfield, D., Carlson, G. A., Iadecola, C., 2001. A beta-peptides enhance vasoconstriction in cerebral circulation. Am. J. Physiol. Heart Circ. Physiol. 281, H2417-24.

Nader, G. A. & Esser, K. A.; Intracellular signalling specificity in skeletal muscle in response to different modes in exercise; J Appl Physiol 90: 1936-1942, 2001.

Ndubuizu, O., and LaManna, J. C. (2007). Brain tissue oxygen concentration measurements. Antioxid. Redox Signal. 9, 1207-1219.

Nunomura, A., Perry, G., Aliev, G., Hirai, K., Takeda, A., Balraj, E. K., Jones, P. K., Ghanbari, H., Wataya, T., Shimohama, S., Chiba, S., Atwood, C. S., Petersen, R. B., Smith, M. A., 2001. Oxidative damage is the earliest event in Alzheimer disease. J. Neuropathol. Exp. Neurol. 60, 759-767.

Ostergaard, L., Chesler, D. A., Weisskoff, R. M., Sorensen, A. G., Rosen, B. R., 1999. Modeling cerebral blood flow and flow heterogeneity from magnetic resonance residue data. J. Cereb. Blood Flow Metab. 19, 690-699.

Østergaard, L., Sorensen, A. G., Chesler, D. A., Weisskoff, R. M., Koroshetz, W. J., Wu, O., Gyldensted, C., Rosen, B. R., 2000. Combined diffusion-weighted and perfusion-weighted flow heterogeneity magnetic resonance imaging in acute stroke. Stroke. 31, 1097-1103.

Østergaard, L., Chesler, D. A., Weisskoff, R. M., Sorensen, A. G., and Rosen, B. R. (1999). Modeling cerebral blood flow and flow heterogeneity from magnetic resonance residue data. J. Cereb. Blood Flow Metab. 19, 690-699.

Park, L., Wang, G., Zhou, P., Zhou, J., Pitstick, R., Previti, M. L., Younkin, L., Younkin, S. G., Van Nostrand, W. E., Cho, S., Anrather, J., Carlson, G. A., Iadecola, C., 2011. Scavenger receptor CD36 is essential for the cerebrovascular oxidative stress and neurovascular dysfunction induced by amyloid-beta. Proc. Natl. Acad. Sci. U.S.A. 108, 5063-5068.

Paulson, O. B., Hasselbalch, S. G., Rostrup, E., Knudsen, G. M., and Pelligrino, D. (2010). Cerebral blood flow response to functional activation. J. Cereb. Blood Flow Metab. 30, 2-14.

Pawlik, G., Rackl, A., Bing, R. J., 1981. Quantitative capillary topography and blood flow in the cerebral cortex of cats: an in vivo microscopic study. Brain Res. 208, 35-58.

Peppiatt, C. M., Howarth, C., Mobbs, P., and Attwell, D. (2006). Bidirectional control of CNS capillary diameter by pericytes. Nature 443, 700-704.

Perlmutter, L. S., Chui, H. C., 1990. Microangiopathy, the vascular basement membrane and Alzheimer's disease: a review. Brain Res. Bull. 24, 677-686.

Pittman, R. N. (2011). Oxygen gradients in the microcirculation. Acta Physiol. (Oxf)

Poole, D. C., Musch, T. I. & Kindig, C. A.; In vivo microvascular structural and functional consequences of muscle length changes; Am. J. Physiol. Heart Circ. Physiol. 272: H2107-H2114, 1997.

Porte, D. Jr. & Kahn, S. E.; β-cell dysfunction and failure in type 2 diabetes: potential mechanism. Diabetes, 2001; 50 suppl 1: S160-163.

Power, M. L. & Schulkin, J.; Maternal obesity, metabolic disease, and allostatic load; Physiol Behav. 2011.

Raichle, M. E., and Mintun, M. A. (2006). Brain work and brain imaging. Annu. Rev. Neurosci. 29, 449-476.

Rattigan, S., Wheatley, C., Richards, S. M., Barrett, E. J. & Clark, M. G.; Exercise and Insulin-Mediated Capillary Recruitment in Muscle; Exerc. Sport Sci. Rev., Vol. 33, No. 1, pp. 43-48, 2005.

Reiman, E. M., Chen, K., Alexander, G. E., Caselli, R. J., Bandy, D., Osborne, D., Saunders, A. M., Hardy, J., 2004. Functional brain abnormalities in young adults at genetic risk for late-onset Alzheimer's dementia. Proc. Natl. Acad. Sci. U.S.A. 101, 284-289.

Reisberg, B., Doody, R., Stoffler, A., Schmitt, F., Ferris, S., Mobius, H. J., Memantine Study Group, 2003. Memantine in moderate-to-severe Alzheimer's disease. N. Engl. J. Med. 348, 1333-1341.

Renkin, E. M., 1985. B. W. Zweifach Award lecture. Regulation of the microcirculation. Microvasc. Res. 30, 251-263.

Rhodes, C. J.; Type 2 diabetes—a matter of β-cell life and death? Science, 2005; 307: 380-384.

Ringman, J. M., Medina, L. D., Braskie, M., Rodriguez-Agudelo, Y., Geschwind, D. H., Macias-Islas, M. A., Cummings, J. L., Bookheimer, S., 2011. Effects of risk genes on BOLD activation in presymptomatic carriers of familial Alzheimer's disease mutations during a novelty encoding task. Cereb. Cortex. 21, 877-883.

Roy, C. S., and Sherrington, C. S. (1890). On the Regulation of the Blood-supply of the Brain. J. Physiol. 11, 85-158.17.

Ruitenberg, A., den Heijer, T., Bakker, S. L., van Swieten, J. C., Koudstaal, P. J., Hofman, A., Breteler, M. M., 2005. Cerebral hypoperfusion and clinical onset of dementia: the Rotterdam Study. Ann. Neurol. 57, 789-794. Scarmeas, N., Habeck, C. G., Hilton, J., Anderson, K. E., Flynn, J., Park, A., Stern, Y., 2005. APOE related alterations in cerebral activation even at college age. J. Neurol. Neurosurg. Psychiatry. 76, 1440-1444.

Scarmeas, N., Habeck, C. G., Stern, Y., Anderson, K. E., 2003. APOE genotype and cerebral blood flow in healthy young individuals. JAMA. 290, 1581-1582.

Scarmeas, N., Stern, Y., 2006. Imaging studies and APOE genotype in persons at risk for Alzheimer's disease. Curr. Psychiatry Rep. 8, 11-17.

Scheibel, A. B., Duong, T. H., Tomiyasu, U., 1987. Denervation microangiopathy in senile dementia, Alzheimer type. Alzheimer Dis. Assoc. Disord. 1, 19-37.

Schulte, M. L., Wood, J. D., and Hudetz, A. G. (2003). Cortical electrical stimulation alters erythrocyte perfusion pattern in the cerebral capillary network of the rat. Brain Res. 963, 81-92.

Shah, K., Qureshi, S. U., Johnson, M., Parikh, N., Schulz, P. E., Kunik, M. E., 2009. Does use of antihypertensive drugs affect the incidence or progression of dementia? A systematic review. Am. J. Geriatr. Pharmacother. 7, 250-261.

Small, G. W., Kepe, V., Ercoli, L. M., Siddarth, P., Bookheimer, S. Y., Miller, K. J., Lavretsky, H., Burggren, A. C., Cole, G. M., Vinters, H. V., Thompson, P. M., Huang, S. C., Satyamurthy, N., Phelps, M. E., Barrio, J. R., 2006. PET of brain amyloid and tau in mild cognitive impairment. N. Engl. J. Med. 355, 2652-2663.

Sorce, S., Krause, K. H., 2009. NOX enzymes in the central nervous system: from signaling to disease. Antioxid. Redox Signal. 11, 2481-2504.

Stefanovic, B., Hutchinson, E., Yakovleva, V., Schram, V., Russell, J. T., Belluscio, L., Koretsky, A. P., Silva, A. C., 2008. Functional reactivity of cerebral capillaries. J. Cereb. Blood Flow Metab. 28, 961-972.

Stefanovic, B., Hutchinson, E., Yakovleva, V., Schram, V., Russell, J. T., Belluscio, L., Koretsky, A. P., and Silva, A. C. (2008). Functional reactivity of cerebral capillaries. J. Cereb. Blood Flow Metab. 28, 961-972.

Stewart, G. N. (1894). Researches on the circulation time in organs and on the influences which affect it. Parts I.-III. J. Physiol. 15, 1-89.

Sun, X., He, G., Qing, H., Zhou, W., Dobie, F., Cai, F., Staufenbiel, M., Huang, L. E., Song, W., 2006. Hypoxia facilitates Alzheimer's disease pathogenesis by up-regulating BACE1 gene expression. Proc. Natl. Acad. Sci. U.S.A. 103, 18727-18732.

Tagami, M., Nara, Y., Kubota, A., Fujino, H., Yamori, Y., 1990. Ultrastructural changes in cerebral pericytes and astrocytes of stroke-prone spontaneously hypertensive rats. Stroke. 21, 1064-1071.

Takeda, S., Sato, N., Takeuchi, D., Kurinami, H., Shinohara, M., Niisato, K., Kano, M., Ogihara, T., Rakugi, H., Morishita, R., 2009. Angiotensin receptor blocker prevented beta-amyloid-induced cognitive impairment associated with recovery of neurovascular coupling. Hypertension. 54, 1345-1352.

Thomas, T., Thomas, G., McLendon, C., Sutton, T., Mullan, M., 1996. beta-Amyloid-mediated vasoactivity and vascular endothelial damage. Nature. 380, 168-171.

Thomas, W. E., 1999. Brain macrophages: on the role of pericytes and perivascular cells. Brain Res. Brain Res. Rev. 31, 42-57.

Tomita, Y., Tomita, M., Schiszler, I., Amano, T., Tanahashi, N., Kobari, M.,

Takeda, H., Ohtomo, M. & Fukuuchi, Y.; Moment Analysis of Microflow histogram in Focal Ischemic Lesion to Evaluate Microvascular Derangement After Small Pial Arterial Occlusion in Rats; Journal of Cerebral Blood Flow Metabolism 22: 663-669, 2002.

Tyml, K.; Capillary recruitment and heterogeneity of microvascular flow in skeletal muscle before and after contraction; Microvascular Research 32, 84-98 (1986).

Vafaee, M. S., and Gjedde, A. (2000). Model of blood-brain transfer of oxygen explains nonlinear flow-metabolism coupling during stimulation of visual cortex. J. Cereb. Blood Flow Metab. 20, 747-754.

Villringer, A., Them, A., Lindauer, U., Einhaupl, K., and Dirnagl, U. (1994). Capillary perfusion of the rat brain cortex. An in vivo confocal microscopy study. Circ. Res. 75, 55-62.

Vogel, J., Abounader, R., Schrock, H., Zeller, K., Duelli, R., and Kuschinsky, W. (1996). Parallel changes of blood flow and heterogeneity of capillary plasma perfusion in rat brains during hypocapnia. Am. J. Physiol. 270, H1441-5.

Vogel, J., and Kuschinsky, W. (1996). Decreased heterogeneity of capillary plasma flow in the rat whisker-barrel cortex during functional hyperemia. J. Cereb. Blood Flow Metab. 16, 1300-1306.

Vogel, J., Waschke, K. F., and Kuschinsky, W. (1997). Flow-independent heterogeneity of brain capillary plasma perfusion after blood exchange with a Newtonian fluid. Am. J. Physiol. 272, H1833-7.

Verbeek, M. M., de Waal, R. M., Schipper, J. J., Van Nostrand, W. E., 1997. Rapid degeneration of cultured human brain pericytes by amyloid beta protein. J. Neurochem. 68, 1135-1141.

Villringer, A., Them, A., Lindauer, U., Einhaupl, K., Dirnagl, U., 1994. Capillary perfusion of the rat brain cortex. An in vivo confocal microscopy study. Circ. Res. 75, 55-62.

Weber, M.-A., Krakowski-Roosen, H., Delonne, S., Renk, H., Krix, M., Millies, J., Kinscherf, R., Künkele, A., Kauczor, H.-U. & Hildebrandt, W.; Relationship of skeletal muscle perfusion measured by contrast-enhanced ultrasonography to histological microvascular density; J Ultrasound Med 2006; 25: 583-591.

Weller, R. O., Subash, M., Preston, S. D., Mazanti, I., Carare, R. O., 2008. Perivascular drainage of amyloid-beta peptides from the brain and its failure in cerebral amyloid angiopathy and Alzheimer's disease. Brain Pathol. 18, 253-266.

Wilhelmus, M. M. M., Otte-Holler, I., van Triel, Veerhuis, R., Maat-Schieman, M. L. C., Bu, G., de Waal, R. M. W., Verbeek, M. M., 2007. Lipoprotein Receptor-Related Protein-1 Mediates Amyloid-β-Mediated Cell Death of Cerebrovascular Cells. Am. J. Pathol. 171, 1989-1999.

Winkler, E. A., Bell, R. D., Zlokovic, B. V., 2011. Central nervous system pericytes in health and disease. Nat. Neurosci. 14, 1398-1405.

Womack, L., Peters, D., Barrett, E. J., Kaul, S., Price, W. & Lindner, J. R.; Abnormal Skeletal Muscle Capillary Recruitment During Exercise in Patients With Type 2 Diabetes Mellitus and Microvascular Complications; Journal of the American College of Cardiology Vol. 53, No. 23, 2009.

Wu, O., Ostergaard, L., Weisskoff, R. M., Benner, T., Rosen, B. R., and Sorensen, A. G. (2003). Tracer arrival timing-insensitive technique for estimating flow in MR perfusion-weighted imaging using singular value decomposition with a block-circulant deconvolution matrix. Magn. Reson. Med. 50, 164-174.

Yamanishi, S., Katsumura, K., Kobayashi, T., Puro, D. G., 2006. Extracellular lactate as a dynamic vasoactive signal in the rat retinal microvasculature. Am. J. Physiol. Heart Circ. Physiol. 290, H925-34.

Yemisci, M., Gursoy-Ozdemir, Y., Vural, A., Can, A., Topalkara, K., Dalkara, T., 2009. Pericyte contraction induced by oxidative-nitrative stress impairs capillary reflow despite successful opening of an occluded cerebral artery. Nat. Med. 15, 1031-1037.

Yuan, G., Khan, S. A., Luo, W., Nanduri, J., Semenza, G. L., Prabhakar, N. R., 2011. Hypoxia-inducible factor 1 mediates increased expression of NADPH oxidase-2 in response to intermittent hypoxia. J. Cell. Physiol. 226, 2925-2933.

Zhang, X., Le, W., 2010. Pathological role of hypoxia in Alzheimer's disease. Exp. Neurol. 223, 299-303.

Zlokovic, B. V., 2011. Neurovascular pathways to neurodegeneration in Alzheimer's disease and other disorders. Nat. Rev. Neurosci. 12, 723-738.

Zlokovic, B. V., 2010. Neurodegeneration and the neurovascular unit. Nat. Med. 16, 1370-1371.

Zschauer, A. O., Davis, E. B., Anderson, D. R., 1996. Glaucoma, capillaries and pericytes. 4. Beta-adrenergic activation of cultured retinal pericytes. Ophthalmologica. 210, 276-279.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A system for measuring a micro-vascular flow distribution of a tissue portion of a mammal, the system comprises:
   a measuring unit for measuring a first indicator of blood flow through a capillary bed;
   a measuring unit for measuring a second indicator of heterogeneity of the blood flow in said capillary bed;
   a first processor operatively connected to the measuring unit for measuring the first indicator, wherein the first processor is arranged for using the measured first and the measured second indicators to estimate an extraction capacity (EC) of a substance from blood in said capillary bed, wherein the estimate includes uptake and diffusion of the substance that is relevant for metabolism;
   wherein the first processor applies a model connecting the measured first and the measured second indicators to the extraction capacity (EC) of the substance from the blood in said capillary bed, the model comprising a transfer rate of total substance concentration (CT) across the capillaries being linearly dependent on a plasma concentration of the substance (CP), the model further comprising a non-vanishing back flow of the substance from tissue into capillaries, wherein the first processor is configured to detect a previously undiagnosed disease based on the heterogeneity of the blood;
   a display operatively connected to the first processor, wherein the display is configured to display images related to the blood flow;
   wherein the measured first indicator is a mean transit time (MTT) of the blood flow, and the measured second indicator is a standard deviation ($\sigma$) of the mean transit time of the blood flow;
   wherein the substance is oxygen and an extraction capacity is the oxygen extraction capacity (OEC);
   wherein the first processor is further arranged for assessing one, or more, of the first indicator, the second indicator, or the extraction capacity with a database comprising reference values thereof; and
   wherein the reference values in the database include threshold values for the first indicator and the second indicator that classify whether the mammal likely has the previously undiagnosed disease.

2. The system according to claim 1, wherein the model is based on at least one rate constant, k, related to a permeability of a capillary wall to the substance.

3. The system according to claim 1, wherein the model applies a variable shift to a rate constant for diffusion of the substance across the capillary (k), the mean transit time (r), and a fractional distance of the capillary (x) to enable an averaging over a transit time distribution to be performed from one capillary.

4. The system according to claim 1, wherein the model further comprises the substance cooperativity due to a non-linear binding of the substance with a protein in blood.

5. The system according to claim 4, wherein the model comprises the oxygen cooperativity due to the non-linear binding of the oxygen with haemoglobin.

6. The system according to claim 1, wherein a first measuring unit for measuring the first indicator for the blood flow through a capillary bed and/or for measuring the second indicator of the heterogeneity of the blood flow in said capillary bed are measurement units based on direct in vivo measurement of a distribution of particle velocities, particle flux, and/or particle transit times.

7. The system according to claim 1, wherein the measuring unit for measuring the first indicator for the blood flow through a capillary bed and/or for measuring the second indicator of the heterogeneity of the blood flow in said capillary bed are measurement units configured for indirect in vivo measurement of distribution of particle velocities, particle flux, and/or particle transit times.

8. The system according to claim 1, wherein the system further comprises the database with reference levels of one, or more, of the first indicator, the second indicator or the extraction capacity for one or more subjects having shock, circulatory shock, septic shock, stroke, hypoxia, ischemia, myocardial ischemia, renal ischemia, reperfusion injury of an organ, an hypoperfusional state, Sickle cell disease, hypotension, hemorrhagic hypotension, cancer, a malignant tumour, diabetes, obesity, hypertension, a systemic autoimmune disease, a systemic sclerosis, a viral encephalopathy, a psychiatric disorder associated with chronic inflammation, depression, schizophrenia, ADHD, autism, aging, a neurodegenerative disease, Alzheimer's disease, dementia, Parkinson's disease, Huntington's Disease, or multiple sclerosis.

9. The system according to claim 1, wherein the threshold values are determined through receiver operating characteristic (ROC) curve analysis.

* * * * *